United States Patent
Pate et al.

(10) Patent No.: US 8,568,113 B2
(45) Date of Patent: Oct. 29, 2013

(54) POSITIVE DISPLACEMENT PUMP SYSTEM AND METHOD

(75) Inventors: Thomas D. Pate, Austin, TX (US); Raul G. Longoria, Austin, TX (US); Richard Smalling, Houston, TX (US); Jeffrey R. Gohean, Austin, TX (US)

(73) Assignee: The Board of Regents of the University of Texas Systems, Austin, TX (US)

( * ) Notice: Subject to any disclaimer, the term of this patent is extended or adjusted under 35 U.S.C. 154(b) by 124 days.

(21) Appl. No.: 12/985,715

(22) Filed: Jan. 6, 2011

(65) Prior Publication Data

US 2011/0160788 A1 Jun. 30, 2011

Related U.S. Application Data

(63) Continuation of application No. 11/773,740, filed on Jul. 5, 2007, now abandoned.

(60) Provisional application No. 60/806,667, filed on Jul. 6, 2006.

(51) Int. Cl.
*F04B 17/00* (2006.01)
*F04B 35/04* (2006.01)

(52) U.S. Cl.
USPC ............... 417/420; 417/410.3; 417/410.1

(58) Field of Classification Search
USPC ............................... 417/420, 410.3
See application file for complete search history.

(56) References Cited

U.S. PATENT DOCUMENTS

| | | | |
|---|---|---|---|
| 1,307,210 A * | 6/1919 | Newcomb | 417/244 |
| 3,144,007 A * | 8/1964 | Kauertz | 418/36 |
| 3,927,329 A | 12/1975 | Fawcett et al. | 290/1 |
| 4,453,537 A * | 6/1984 | Spitzer | 623/3.12 |
| 4,459,087 A * | 7/1984 | Barge | 417/356 |
| 4,563,622 A * | 1/1986 | Deavers et al. | 318/400.26 |
| 4,621,617 A | 11/1986 | Sharma | 128/1 |
| 4,949,022 A * | 8/1990 | Lipman | 318/400.08 |
| 5,044,897 A * | 9/1991 | Dorman | 417/423.7 |
| 5,080,562 A | 1/1992 | Barrows et al. | 417/353 |
| 5,089,016 A | 2/1992 | Millner et al. | 623/3.21 |
| 5,089,017 A * | 2/1992 | Young et al. | 623/3.11 |
| 5,192,201 A * | 3/1993 | Beben | 418/38 |
| 5,286,176 A * | 2/1994 | Bonin | 417/413.1 |
| 5,344,443 A | 9/1994 | Palma et al. | 623/3.14 |
| 5,695,471 A | 12/1997 | Wampler | 604/131 |

(Continued)

FOREIGN PATENT DOCUMENTS

DE 198 16 120 6/1999
DE 198 57 599 6/2000

OTHER PUBLICATIONS

Chung et al., "Impeller Behavior and Displacement of the VentrAssist Implantable Rotary Blood Pump," *Artificial Organs*, 28(3):287-297, 2004.

(Continued)

*Primary Examiner* — Charles Freay
*Assistant Examiner* — Alexander Comley
(74) *Attorney, Agent, or Firm* — Streets & Steele

(57) ABSTRACT

Systems and methods including a motor or electromagnets to control the movement of one or more pistons in a pumping chamber. The pumping chamber may include a pump inlet and a pump outlet in fluid communication with the pumping chamber. Surfaces on a piston or pumping chamber may include hydrodynamic bearing surfaces.

10 Claims, 42 Drawing Sheets

(56) References Cited

U.S. PATENT DOCUMENTS

| | | | |
|---|---|---|---|
| 5,800,138 A * | 9/1998 | Merce Vives | 417/374 |
| 5,829,338 A | 11/1998 | Chrestoff et al. | 92/12.2 |
| 5,840,070 A | 11/1998 | Wampler | 604/131 |
| 5,895,421 A | 4/1999 | Nakhmanson | 604/131 |
| 5,924,975 A | 7/1999 | Goldowsky | 600/16 |
| 5,967,749 A * | 10/1999 | Eaves et al. | 416/3 |
| 6,080,133 A | 6/2000 | Wampler | 604/131 |
| 6,194,798 B1 * | 2/2001 | Lopatinsky | 310/63 |
| 6,227,817 B1 * | 5/2001 | Paden | 417/356 |
| 6,342,071 B1 | 1/2002 | Pless | 623/3.1 |
| 6,576,010 B2 * | 6/2003 | Ulert et al. | 623/3.1 |
| 6,641,378 B2 * | 11/2003 | Davis et al. | 417/423.7 |
| 6,841,910 B2 * | 1/2005 | Gery | 310/103 |
| 6,846,168 B2 | 1/2005 | Davis et al. | 417/423.7 |
| 7,238,165 B2 | 7/2007 | Vincent et al. | 604/6.11 |
| 7,371,223 B2 | 5/2008 | Couvillon et al. | 604/9 |
| 7,462,019 B1 | 12/2008 | Allarie et al. | 417/423.12 |
| 2002/0019666 A1 * | 2/2002 | Ulert et al. | 623/3.1 |
| 2004/0015042 A1 * | 1/2004 | Vincent et al. | 600/17 |
| 2004/0066107 A1 * | 4/2004 | Gery | 310/103 |
| 2005/0043766 A1 | 2/2005 | Soykan et al. | 607/9 |
| 2005/0196293 A1 | 9/2005 | Ayre et al. | 417/353 |
| 2005/0281685 A1 * | 12/2005 | Woodard et al. | 417/365 |
| 2007/0265703 A1 | 11/2007 | Sutton et al. | 623/3.1 |
| 2008/0008609 A1 | 1/2008 | Pate et al. | 417/415 |

OTHER PUBLICATIONS

Office Action issued in European Application No. 07 812 644.8, mailed Oct. 29, 2010.

Office Action issued in U.S. Appl. No. 11/773,740, mailed Aug. 6, 2010.

Office Action issued in U.S. Appl. No. 11/773,740, mailed Jan. 25, 2010.

Office Action issued in U.S. Appl. No. 11/773,740, mailed Jul. 29, 2009.

Office Action issued in U.S. Appl. No. 11/773,740, mailed Mar. 13, 2009.

PCT International Preliminary Report on Patentability issued in International Application No. PCT/US2007/072872, mailed Jan. 15, 2009.

PCT International Search Report and Written Opinion issued in International Application No. PCT/US2007/072872, mailed Jan. 16, 2008.

* cited by examiner

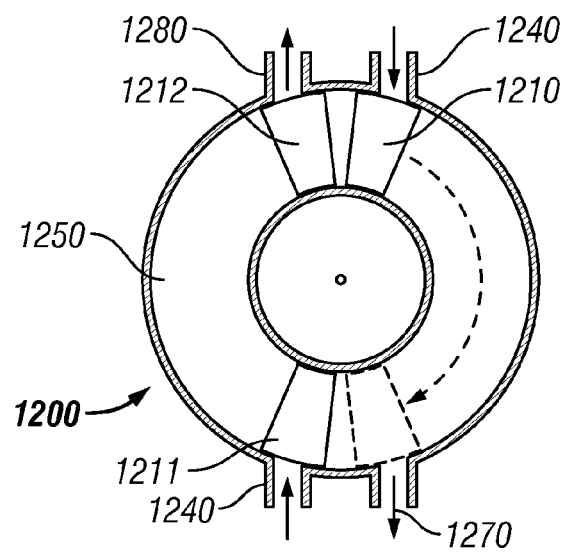
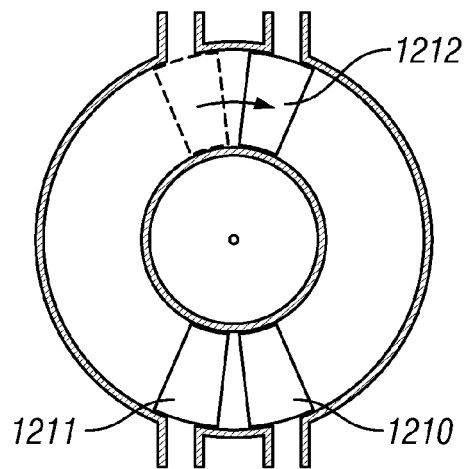
FIG. 34A  FIG. 34B
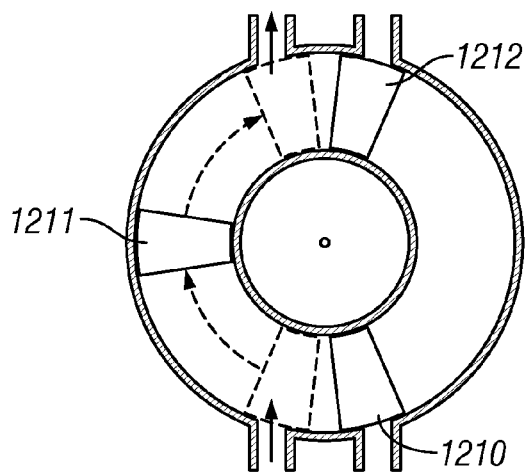
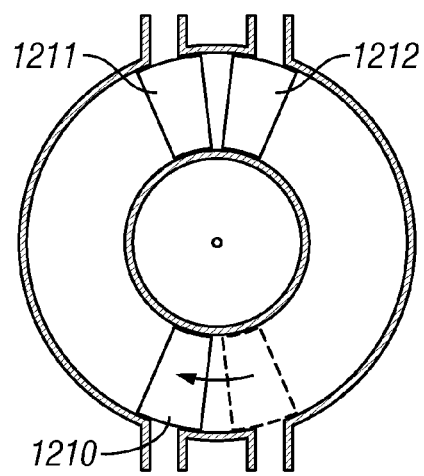
FIG. 34C  FIG. 34D

POSITIVE DISPLACEMENT PUMP SYSTEM AND METHOD

CROSS-REFERENCE TO RELATED APPLICATIONS

This application is a continuation of currently pending U.S. patent application Ser. No. 11/773,740 filed Jul. 5, 2007, which claims priority to U.S. Provisional Patent Application No. 60/806,667 filed on Jul. 6, 2006. The entire text of each of the above-referenced disclosures is specifically incorporated herein by reference without disclaimer.

BACKGROUND OF THE INVENTION

1. Field of the Invention

Embodiments of the present invention generally relate to pumps. More specifically, and not by way of limitation, embodiments of the present invention relate to positive displacement pumps for the circulation of fluids.

2. Description of Related Art

Many natural and manmade fluids contain molecules that can be damaged or destroyed by excessive shearing strains or stagnation that can occur in devices that attempt to pump these fluids. Fluids containing molecules with high molecular weights such as proteins, long stranded synthetic polymers, DNA, RNA, or fluids such as blood, which contain concentrations of delicate cells, are especially susceptible to being compromised by many conventional pumping techniques.

Typical axial flow and centrifugal pumps operate by rotating an impeller at very high speeds, often exceeding 12,000 RPM. The shearing stresses that can arise at these velocities can strain larger fluid molecules until they break, leading to destruction or undesirable alteration of the pumping medium. For instance, it is well documented that the pumping of blood using centrifugal and axial flow pumps shears the phospholipid bilayer of erythrocytes and platelets to the point of lysing the cells and releasing their cytosolic proteins and organelles into the blood stream. This phenomenon, known as hemolysis, is an issue in the field of artificial blood circulation because the releasing of hemoglobin into the blood stream can cause kidney failure in patients who receive this blood. Thus, there is useful need for pump designs that can provide fluid circulation without damaging a delicate pumping medium such as blood.

Further objects and advantages of this system and method will become apparent from a consideration of the drawings and ensuing description.

SUMMARY OF THE INVENTION

Embodiments of the present disclosure provide systems and methods for pumping fluids. While certain embodiments may be particularly suited for pumping delicate fluids with low shearing strains, it is understood that embodiments of the present disclosure are not limited to pumping such fluids. Other embodiments may be used to pump fluids that are not delicate or do not have low shearing strains.

Certain embodiments comprise: a pumping chamber forming a loop; a pump inlet in fluid communication with the pumping chamber; a pump outlet in fluid communication with the pumping chamber; a first piston disposed within the pumping chamber; a second piston disposed within the pumping chamber; an electric motor; and an electromagnet, wherein the system is configured such that during operation: the electromagnet is initially coupled to the first piston; the electric motor is initially coupled to the second piston; the electromagnet is subsequently coupled to the second piston; and the electric motor is subsequently coupled to the first piston. In certain embodiments, the electromagnet is coupled to either the first or second piston when the electromagnet is energized and the electromagnet is not coupled to either the first or second piston when the electromagnet is de-energized. Certain embodiments further comprise a magnetic ring, and are configured such that during operation: the electric motor exerts a first magnetic force on the first piston; the magnetic ring exerts a second magnetic force on the first piston; and the first magnetic force opposes the second magnetic force. In certain embodiments, the magnetic ring and/or the pistons comprise a permanent magnet or Halbach array. In certain embodiments, the system is configured such that during operation: the motor comprises a rotor with a magnetic link (which may comprise a permanent magnet or Halbach array) and the magnetic link is initially coupled to the second piston and subsequently coupled to the first piston.

Certain embodiments are configured such that during operation a portion of the magnetic link extends beyond a leading face of the piston. In certain embodiments, the system is configured such that during operation the pump inlet is inserted into a ventricle and the pump outlet is in fluid communication with the ascending aorta, the descending aorta, or a pulmonary artery. In certain embodiments, the system is configured such that: the motor comprises a rotor coupled to a linking arm; the linking arm is coupled to a first magnet, wherein the first magnet is located on a first side of the piston during operation; the linking arm is coupled to a second magnet, wherein the second magnet is located on a second side of the piston during operation; and the first side is opposed to the second side. In certain embodiments, the first piston or the second piston comprise a hydrodynamic bearing surface.

Other embodiments comprise a method of pumping a fluid, the method comprising: providing a pumping chamber, wherein the pumping chamber contains the fluid; providing a pump inlet in fluid communication with the pumping chamber; providing a pump outlet in fluid communication with the pumping chamber; providing a first piston disposed within the pumping chamber; providing a second piston disposed within the pumping chamber; providing an electric motor comprising a rotor; providing an electromagnet; coupling the electromagnet to the first piston; coupling the rotor to the second piston; holding the first piston in a first location with the electromagnet; rotating the rotor and moving the second piston closer to the first piston so that a portion of the fluid is forced out of the pump outlet; de-energizing the electromagnet and uncoupling the electromagnet from the first piston; energizing the electromagnet so that it couples to the second piston; and coupling the rotor to the first piston. Certain embodiments further comprise rotating the rotor and moving the first piston closer to the second piston so that a portion of the fluid is forced out of the pump outlet. In certain embodiments, the first location is between the pump inlet and the pump outlet.

Still other embodiments comprise: a pumping chamber comprising an inner surface forming a loop; a pump inlet in fluid communication with the pumping chamber; a pump outlet in fluid communication with the pumping chamber; a piston disposed within the pumping chamber; and a first electric motor magnetically coupled to the piston, wherein: the piston comprises a hydrodynamic bearing surface configured to repel the piston away from the inner surface as the piston moves within the pumping chamber. In certain embodiments, the loop is centered about a central axis; the piston comprises an upper surface, a lower surface, an inner surface, an outer surface, a leading face, and a trailing face; and the inner surface comprises an upper wall, a lower wall, an inner wall and an outer wall.

In certain embodiments, during operation: a first lower gap exists between the lower surface and the lower wall proximal to the leading face; a second lower gap exists between the lower surface and the lower wall proximal to the trailing face; the first lower gap is larger than the second lower gap; a first upper gap exists between the upper surface and the upper wall proximal to the leading face; a second upper gap exists between the upper surface and the upper wall proximal to the trailing face; and the first upper gap is larger than the second upper gap. In certain embodiments, a portion of the lower surface is not perpendicular to the central axis and a portion of the upper surface is not perpendicular to the central axis.

In certain embodiments, a first outer gap exists between the outer surface and the outer wall proximal to the leading face; a second outer gap exists between the outer surface and the outer wall proximal to the trailing face; and the first outer gap is larger than the second outer gap. Certain embodiments comprise a pinch valve between the pump inlet and the pump outlet. Certain embodiments also comprise a second piston disposed within the pumping chamber, and a second electric motor coupled to the second piston, wherein the second piston comprises a hydrodynamic bearing surface configured to repel the second piston away from the inner surface as the second piston moves within the pumping chamber.

Certain embodiments comprise: a power supply; a driver circuit electrically coupled to the electric motor and the power supply; a microprocessor electrically coupled to the driver circuit; and a sensor for sensing a position of the piston within the pumping chamber, wherein: the driver circuit is configured to selectively couple the power supply to the electric motor upon receiving a control signal; the sensor is electrically connected to the microprocessor; the microprocessor is configured to interpret the position from the sensor; the microprocessor is configured to output the control signal to the driver circuit. In certain embodiments, a position and a velocity of the piston are controlled to produce a predetermined waveform in an outlet flow from the pump outlet. Certain embodiments comprise a fluid within the pumping chamber and a sensor configured to measure a property of the fluid. In certain embodiments, the piston or inner surface comprise one or more of the following: a nanoparticulate surface, a microporous coating, or a fibrous flocking. In certain embodiments the nanoparticulate surface, microporous coating, or fibrous flocking are configured to facilitate endothelial or pseudoneointimal protein or cell aggregation.

Certain embodiments comprise a pacemaker and a microprocessor, wherein: the pacemaker comprises one or more electrodes electrically coupled to a heart; the pacemaker is electrically coupled to the microprocessor; the pacemaker provides a depolarization output to the one or more electrodes; and the heart is controlled to contract at a predetermined time relative to an actuation stroke of the pump. Certain embodiments comprise a sensor, wherein the sensor is configured to sense a physiological parameter and the system is configured to increase or decrease a volumetric flow rate from the pumping chamber based on the physiological parameter. In certain embodiments the sensor comprises one or more electrodes for measuring thoracic impedance, p-wave activity, renal sympathetic nerve activity, or aortic nerve activity. In other embodiments, the sensor comprises an accelerometer for sensing heart contraction, diaphragm motion, bodily inclination, or walking pace.

Certain embodiments comprise a pump for circulating fluid comprising: a pumping chamber; a pump inlet in fluid communication with the pumping chamber; a pump outlet in fluid communication with the pumping chamber; a drive piston disposed within the pumping chamber; and a hollow valve sleeve configured to recess into the pump outlet.

Other embodiments comprise: a pumping chamber forming a loop; a pump inlet in fluid communication with the pumping chamber; a pump outlet in fluid communication with the pumping chamber; a piston disposed within the pumping chamber; an electric motor comprising a rotor coupled to a shaft; a magnet coupled to an end of the shaft; a sensor proximal to the magnet; and a control system, wherein: the electric motor is magnetically coupled to the piston; the magnet produces a magnetic vector that rotates with the rotor; the sensor is configured sense the magnetic vector; and the control system is configured to determine the angular position of the rotor. In certain embodiments, the sensor is a 2-axis Hall effect sensor and the electric motor is an axial flux motor. In certain embodiments, the control system is configured to access a lookup table.

Certain embodiments comprise a pumping chamber comprising an inner surface forming a loop; a pump inlet in fluid communication with the pumping chamber; a pump outlet in fluid communication with the pumping chamber; a first piston disposed within the pumping chamber; and a series of electromagnets disposed around the pumping chamber, wherein: the series of electromagnets are configured to move the first piston around the pumping chamber; and the first piston comprises a hydrodynamic bearing surface configured to repel the first piston away from the inner surface as the first piston moves within the pumping chamber. Certain embodiments further comprise a second piston disposed within the pumping chamber, wherein: the series of electromagnets are configured to move the second piston around the pumping chamber; and the second piston comprises a hydrodynamic bearing surface configured to repel the second piston away from the inner surface as the second piston moves within the pumping chamber. Certain embodiments further comprise a pinch valve between the pump inlet and pump outlet.

As used herein, the terms "a" and "an" are defined as one or more unless this disclosure explicitly requires otherwise.

The term "substantially" and its variations are defined as being largely but not necessarily wholly what is specified as understood by one of ordinary skill in the art, and in one non-limiting embodiment the term "substantially" refers to ranges within 10%, preferably within 5%, more preferably within 1%, and most preferably within 0.5% of what is specified.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

The term "coupled," as used herein, is defined as connected, although not necessarily directly, and not necessarily mechanically.

BRIEF DESCRIPTION OF THE DRAWINGS

FIGS. 34A-34D are section views of an embodiment of the present disclosure in different stages of operation.

DETAILED DESCRIPTION OF THE INVENTION

Figure 1:
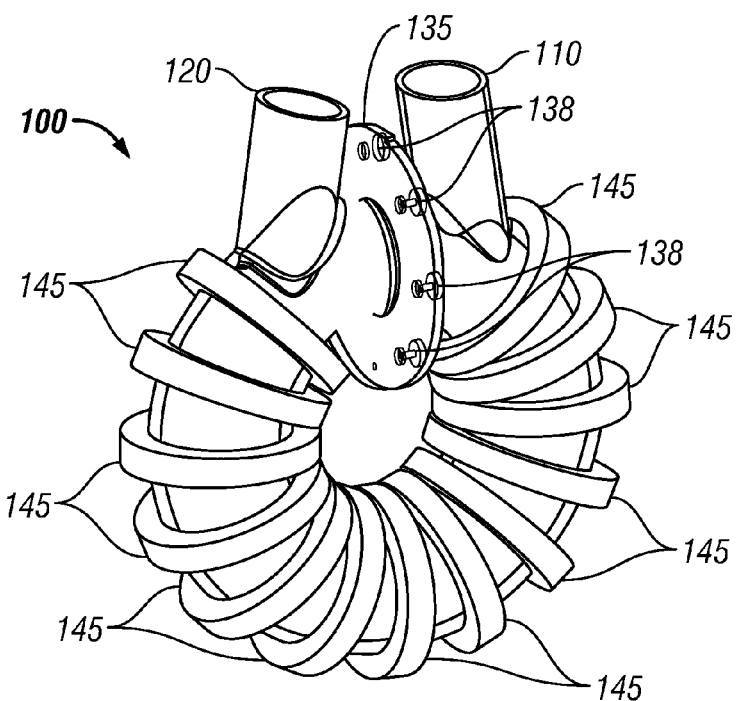
FIG. 1 is a perspective view of one embodiment of the present disclosure.
Figure 2:
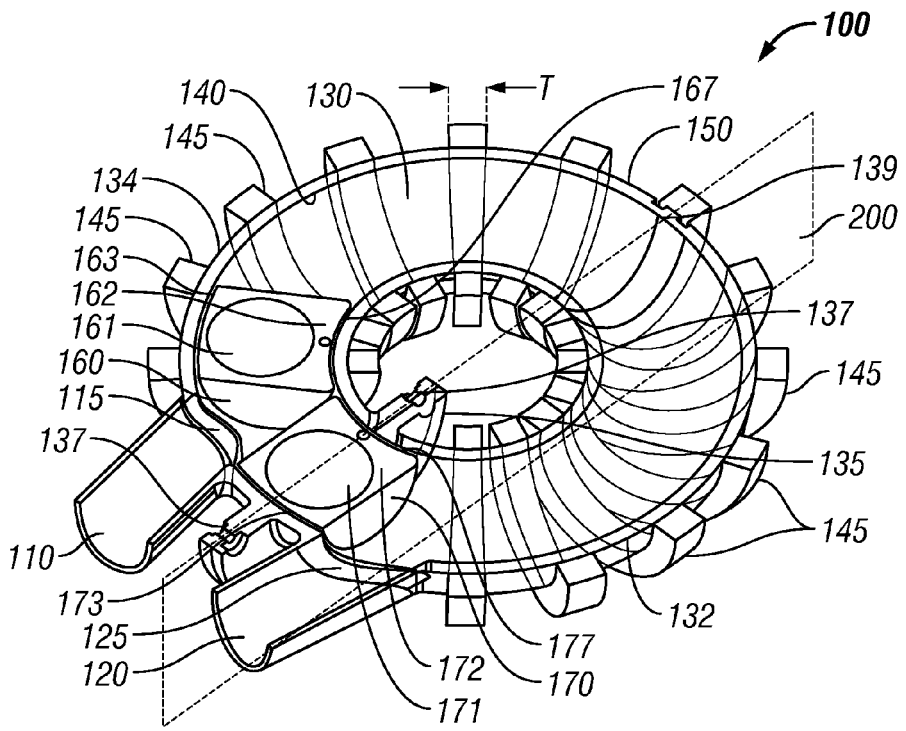
FIG. 2 is a section view of the embodiment of FIG. 1.

FIGS. 1 and 2 show a perspective and sectioned view, respectively, of a pump 100 with an inlet 110 and an outlet 120. It should be appreciated that pump 100 shown in FIGS. 1 and 2 is one exemplary embodiment, and the present invention should not be limited to the embodiment shown. The same is true for all other Figures, which are provided as examples only.

The embodiments illustrated in FIGS. 1-13 show a pumping chamber 130 forming a loop or ring comprised of an inner wall 140 and an outer wall 150 defining a lumen generated by the revolution of a two-dimensional enclosed contour, in this case a circle, about a coplanar axis lying outside the contour. It should be appreciated that many two dimensional enclosed contours can be used to define the lumen including a square, ellipse, polygon, conic, etc. It should also be appreciated that the revolution path should not be restricted to a circle. For instance, the enclosed contour may be swept around an oval, ellipse, etc. Pumping chamber 130 is comprised of a rigid plastic material such as poly ether ether ketone (PEEK) blow molded or injection molded into shape. However, pumping chamber 130 can consist of a variety of materials including plastic, titanium, stainless steel, aluminum, or a photo-reactive polymeric resin used in stereolithography. Pumping chamber 130 contains a first orifice 115 and second orifice 125 located along its outer perimeter sized so that a pair of pistons 160 and 170 residing within pumping chamber 130 cannot enter the orifices or catch along the interface where the orifice 115 meets inlet 110 or orifice 125 meets outlet 120. Inlet 110 is in fluid communication with first orifice 115 of pumping chamber 130 such that inlet 110 joins pumping chamber 130 at an angle 180. Outlet 120 is in fluid communication with second orifice 125 of pumping chamber 130 such that outlet 120 joins pumping chamber 130 at an angle 190. It should be appreciated that the position of first orifice 115 and second orifice 125 are not required to reside along the radial perimeter of pumping chamber 130, but could exist in various positions elsewhere on pumping chamber 130. It should also be appreciated that inlet 120 and outlet 130 could intercept the pumping chamber at a variety of angles. It should further be appreciated that the outer wall of the pumping chamber need not be an identically shaped offset of the inner wall of the pumping chamber. Where inner wall 140 has a direct relationship to the volume created by the revolution of the two-dimensional enclosed contour, outer wall 150 of pumping chamber 130 can adopt many different shapes to accommodate the need for mounting sensors, electromagnets, wires, etc. In the embodiment shown, pumping chamber 130 is composed of two halves 132 and 134, which separate and attach along a plane 200. Between and nearest the inflow and outflow conduits 110 and 120, a flange 135 exists on each half 132, 134 of pumping chamber 130. Flange 135 comprises counter-bored clearance holes 137 in which fasteners 138 are inserted and tightened down to create a hermetic seal. No flange exists along the second attachment surface 139 to allow for a plurality of solenoids 145 to be slid onto each half 132, 134 of pumping chamber 130. The attachment of each half 132, 134 at second attachment surface 139 is sealed by ultrasonic welding of the contact seam. It should be appreciated that many materials and methods may be used to attach the chamber halves 132, 134 together including adhesives, snap fits, press fits, fasteners, ultrasonic welding, laser welding, etc. In certain embodiments, inner wall 140 of pumping chamber 130 is coated with a hydrophilic lining (not shown) that partially absorbs fluid to enhance lubricity. The inner lining of pumping chamber 130 and/or the pistons 160, 170 may be coated in the following material types for the facilitation of protein or cellular aggregation for increasing lubricity, sealing, durability, and lowering hemolysis and thrombosis: a nano-particulate surface (carbon, silicate, or titanium based), a micro-porous ceramic, or a fibrous flocking material. It should be appreciated that many other surface coatings, such as diamond-like carbon and titanium nitride, may be used to provide increases in biocompatibility, lubricity, sealing, and durability, and decreases in thrombosis and hemolysis, and that these materials serve only as an example of several embodiments.

The present embodiment further shows two pistons 160, 170 residing within the lumen of pumping chamber 130. Each piston 160, 170 contains a rare earth magnetic sphere 161, 171 encapsulated by two halves 162, 172 of a rigid housing that joins and seals along an edge with epoxy 9 (not shown). The magnetic spheres 161, 171 are fixed at the center of pistons 160, 170 with epoxy so that the spheres 161, 171 cannot rotate within pistons 160, 170. The housing of each piston 160, 170 conforms to a great extent with the inner shape of the lumen or pumping chamber 130, the pistons 160, 170 having a toroidal curvature terminating on both ends with a planar face. In the embodiment shown, the two planar end faces of pistons 160, 170 are configured so that the end faces are parallel. However, it should be appreciated that many different piston shapes could be used including pistons whose end faces are angled and pistons with sculpted extensions to facilitate the smooth transition of fluid into and out of the pump. In certain embodiments, all edges along the piston are filleted to minimize frictional wear and a hydrophilic coating (not shown) that partially absorbs fluid surrounds each piston 160, 170, enhancing its lubricity. While residing in pumping chamber 130, small clearance gaps 163 and 167 exist between piston 160 and pumping chamber 130 allowing piston 160 to move within pumping chamber 130 without significant contact friction. Similarly, small clearance gaps 173 and 177 exist between the piston 170 and pumping chamber 130. The orientation of spherical magnet 161, 171 within each piston 160, 170 are set such that the net magnetic vector points substantially parallel to the instantaneous velocity vector of the piston as it moves in the pumping chamber 130. Pistons 160, 170 are placed within pumping chamber 130 at orientations such that pistons 160, 170 magnetically oppose one another as they reside within pumping chamber 130. Pistons 160, 170 are also sized to prevent their insertion or collision with orifices 115, 125 of pumping chamber 130.

FIGS. 1-13 further show one embodiment of a means for actuating pistons 160, 170 within pumping chamber 130. In the embodiments shown, a plurality of solenoids 145 are discretely placed along outer wall 150 of pumping chamber, each solenoid 145 consisting of a wound conductor supported by a resin to retain a self standing ring shape that extends around pumping chamber 130. Each solenoid 145 is slid onto pumping chamber 130 and mounted into place using an adhesive (not shown). It should be appreciated that the conducting wire of each solenoid 145 can be chosen from a wide variety of metals such as copper, aluminum, gold, silver, Litz wire, etc and the gauge of the wire can be varied. Each solenoid 145 conforms along its inner surface with the curvature of the outer wall 150 of pumping chamber 130. Each solenoid 145 is also tapered so that the thickness (shown as dimension "T" in FIG. 2) of the solenoid decreases as one moves radially inward from the outer edge of pump 100 towards the center, facilitating a maximal packing factor of coils onto pumping chamber 130. In the embodiments shown, solenoids 145 take the aspect ratio approximating a Brook's coil so as to maximize the force transduced between each piston 160, 170 and each solenoid 145. It should be appreciated that in other embodiments, more or less solenoids could be used and that the solenoids can be of a wide range of shapes and each need not be of identical shape.

Figure 3:
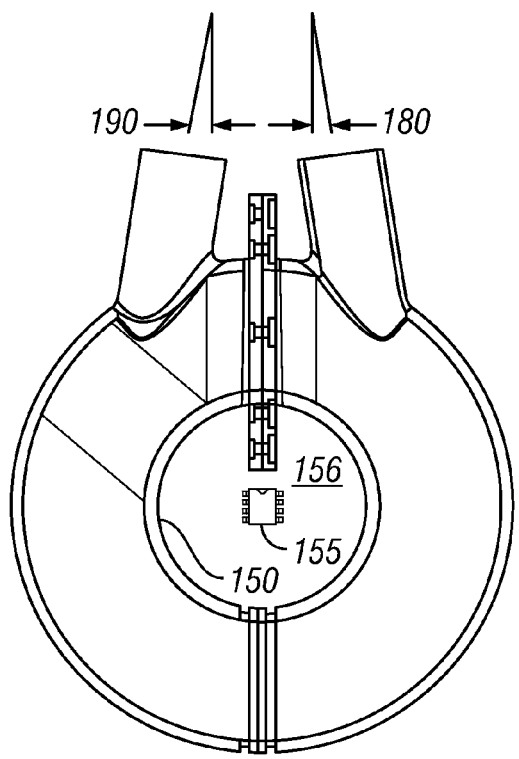
FIG. 3 is a side view of one embodiment of the present disclosure.

FIG. 3 shows one embodiment of a means for sensing the angular positions of the magnetic pistons 160, 170 using a 2-axis Hall effect sensor 155 located in the void at the center of the pump. Sensor 155 can be mounted on a variety of support structures (not shown) extending from outer wall 150 of pumping chamber 130 into void 156 at the center of pump 100. For purposes of clarity, solenoids 145 or other means for actuating pistons 160, 170 are not shown in FIG. 3.

Figure 4:
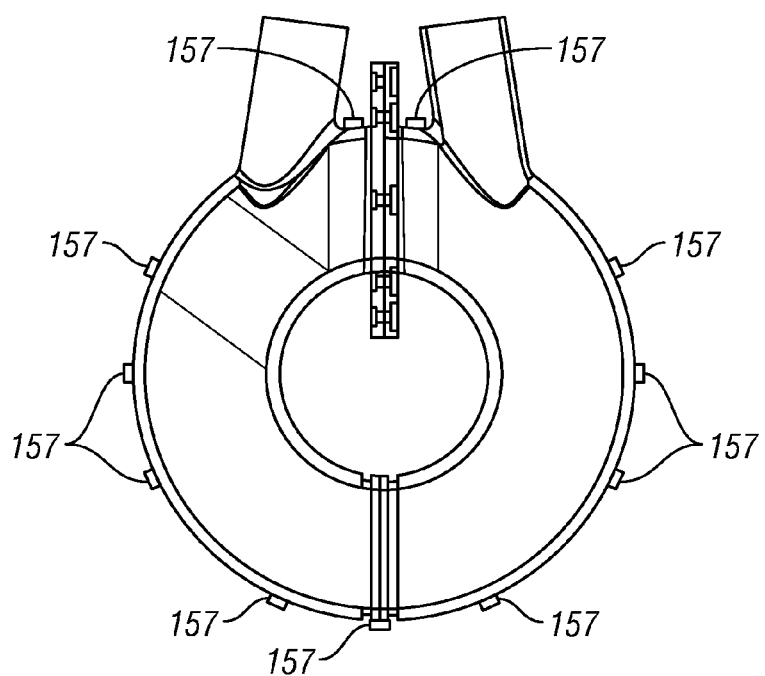
FIG. 4 is a side view of one embodiment of the present disclosure.

FIG. 4 shows another embodiment of a means for sensing the angular positions of the magnetic pistons 160, 170 using a plurality of single axis Hall effect sensors 157 positioned around the perimeter of outer wall 150 of pumping chamber 130 and mounted with an adhesive (not shown) or other suitable means. For purposes of clarity, solenoids 145 or other means for actuating pistons 160, 170 are not shown in FIG. 4.

Figure 5:
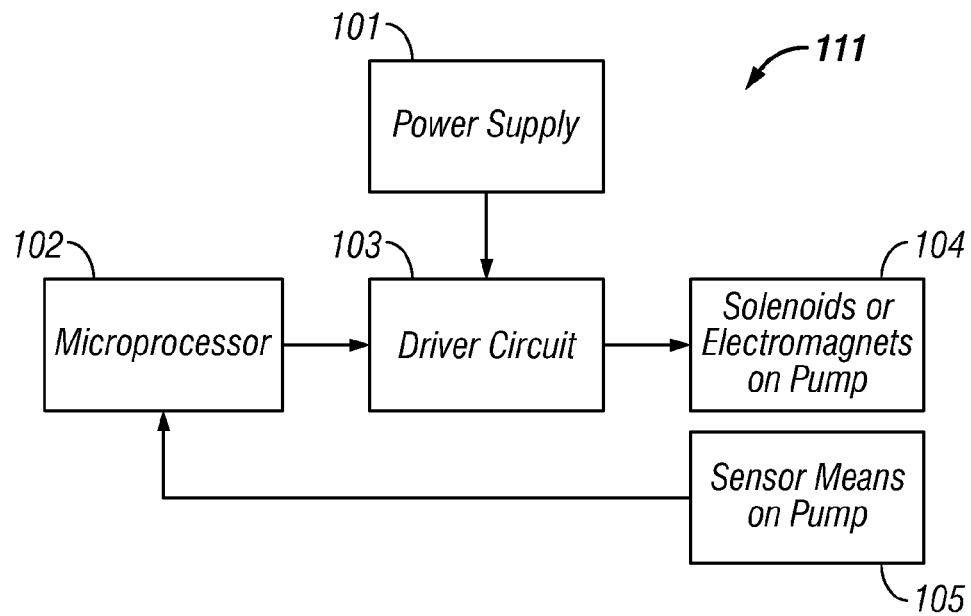
FIG. 5 is a schematic of a control system used in certain embodiments of the present disclosure.

As shown in FIG. 5, one embodiment of a control system 111 for operating pump 100 comprises a power supply 101, a microprocessor 102, a driver circuit 103, a plurality of solenoids or electromagnets 104, and a plurality of sensors 105. It should be appreciated that microprocessor 102 could take the form of a real time operating system, microcontroller, CPU, etc. Microprocessor 102 is electrically connected to a driver circuit 103 and sensors 105 located on pump 100. Driver circuit 103 is electrically connected to power supply 101 and electrically connected to solenoids or electromagnets 104 (or other means for actuating pistons 160, 170 within pumping chamber 130). It should be appreciated that power supply 101 can comprise a bench top alternating or direct voltage source, a battery, a fuel cell, a bank of capacitors, etc.

Figure 6:
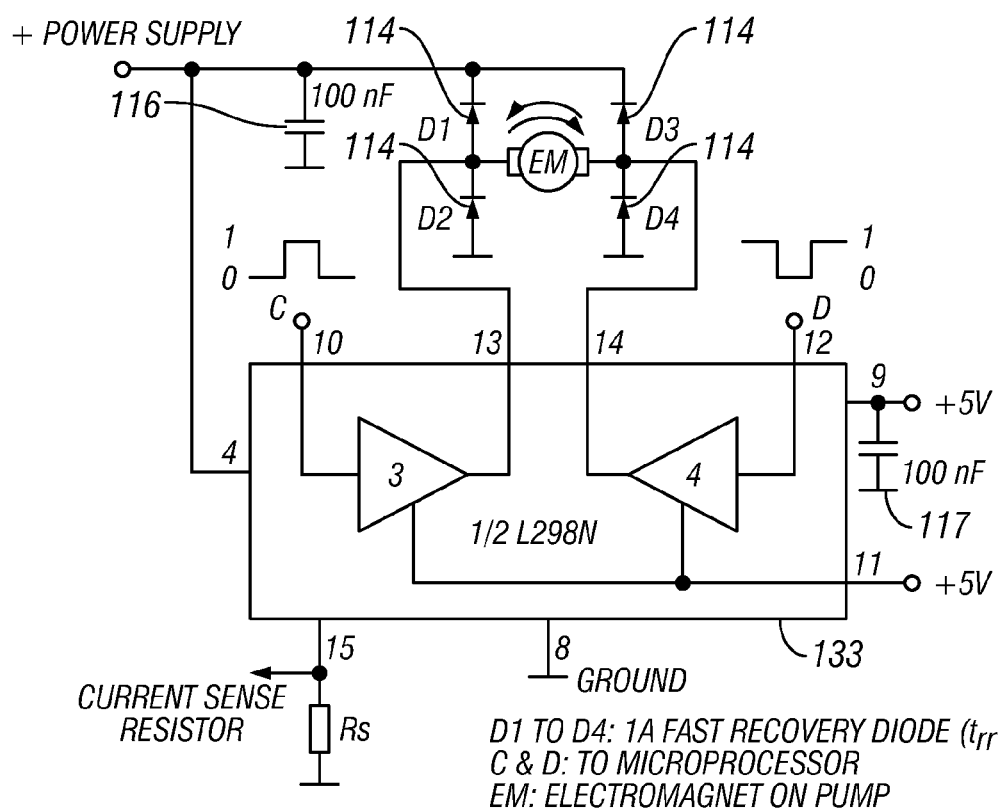
FIG. 6 is a schematic of a driver circuit diagram used in certain embodiments of the present disclosure.

As shown in FIG. 6 one embodiment of driver circuit 101 comprises a full bridge MOSFET driver 133 with pullup capacitors 116 and 117 and flyback diodes 114.

Figure 7:
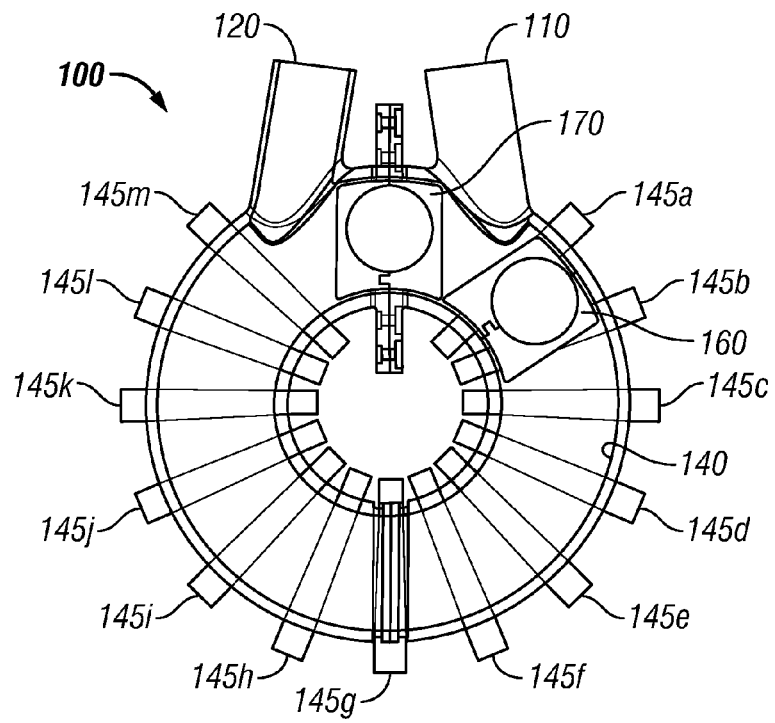
FIG. 7 is a section view of one embodiment of the present disclosure during operation.

In the embodiment shown, pump 100 circulates fluid (not shown) in two phases, a drive phase and a transition phase, which are cyclically alternated in the operation of pump 100. FIG. 7 shows piston 160 in a first position with piston 170 located substantially between inlet 110 and outlet 120 and the piston 160 residing close to piston 170 near inlet 110. This position marks the end of the transition phase and the beginning of the drive phase. In the embodiment shown, one cycle of the drive phase occurs by actuating piston 160 in a clockwise motion around the lumen of pumping chamber 130 while maintaining piston 170 in the position between inlet 110 and outlet 120. Piston 160 is actuated clockwise in the embodiment shown by delivering a current to solenoid 145b in a direction which produces an attractive force on the piston 160. It should be appreciated that the solenoids 145c and 145d may also be energized to produce additional attractive forces on the piston 160 as well, as is the case when needing a higher force to pump fluid against a higher pressure at outlet 120. It should also be appreciated that the solenoid 145a may be energized to produce a repelling force to further accelerate piston 160 in a clockwise direction. However, in the embodiment shown, first solenoid 145a remains off in this initial sequence to prevent producing an attractive force on the piston 170. Piston 170 is located close to solenoid 145a and therefore could move if solenoid 145a were energized to repel piston 160. The forces placed on piston 160 by the solenoid 145b cause it to move clockwise. As piston 160 begins to move, it pushes on the fluid that resides in the volume between its leading face and outlet 120. Due to the close clearance between the inner wall 140 and piston 160, which is enhanced by the hydrophilic coating that further facilitates a sealing effect, the fluid does not substantially leak around piston 160, but is rather forced to move with piston 160. Simultaneously, the solenoid 145m is delivered current by control system 111 (schematically shown in FIG. 5) to produce a holding force which isolates piston 170 in the position between inlet 110 and outlet 120. Piston 170, due to its geometry and hydrophilic coating, also produces a substantial occlusion to the fluid flow. It is in this fashion that the piston 160 pressurizes fluid between its leading face and piston 170, causing the fluid to exit pumping chamber 130 through outlet 120. Simultaneously, the expanding volume change induced by the motion piston 160 creates a lower pressure between its lagging face and piston 170. This low pressure forces fluid to enter into pumping chamber 130 through inlet 110. As piston 160 moves clockwise, the solenoids it approaches are delivered currents by control system 111 to further attract piston 160 and the solenoids that piston 160 has recently passed through are delivered reversed currents by control system 111 to further repel piston 160. As piston 160 crosses the midplane of each solenoid, control system 111 reverses the direction of the current supplied to that particular solenoid in order to produce a repelling force which expels piston 160 through the solenoid along the same clockwise direction. The use of solenoids to produce both an attracting force and a repelling force provides greater efficacy in the transportation of piston 160, and surpasses the performance of the prior art designs which only utilize attractive forces to propel the piston around the pumping chamber.

Figure 8:
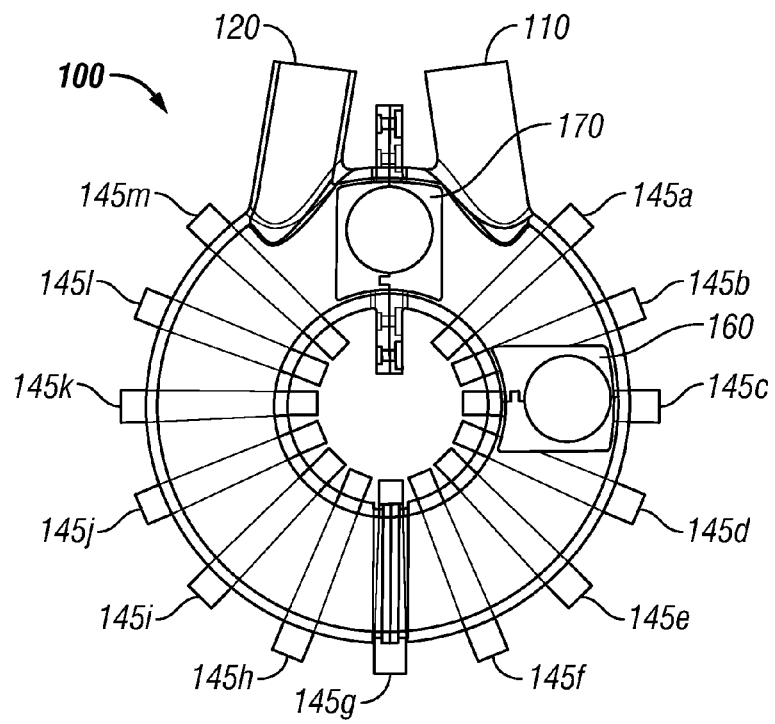
FIG. 8 is a section view of one embodiment of the present disclosure during operation.
Figure 9:
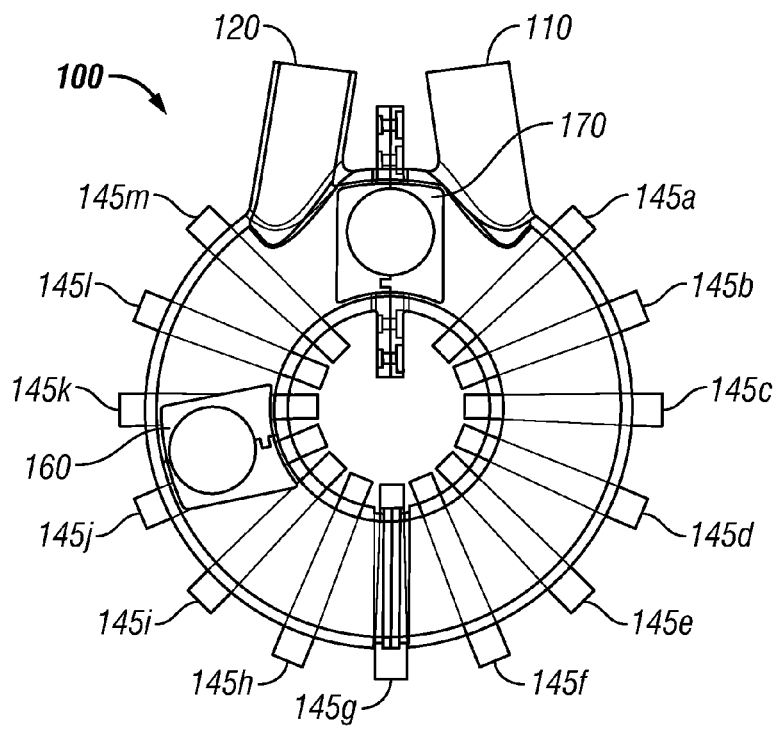
FIG. 9 is a section view of one embodiment of the present disclosure during operation.
Figure 10:
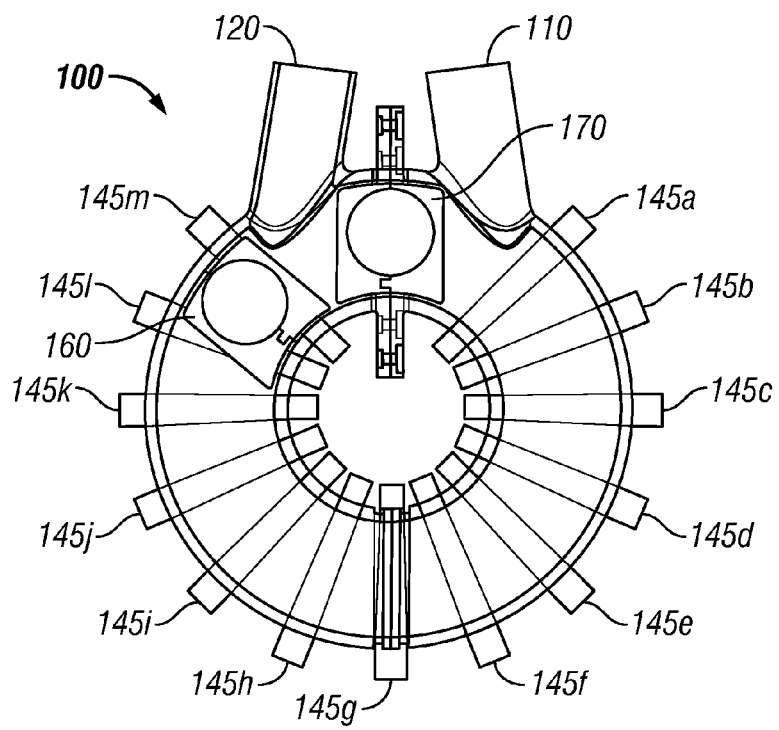
FIG. 10 is a section view of one embodiment of the present disclosure during operation.
Figure 11:
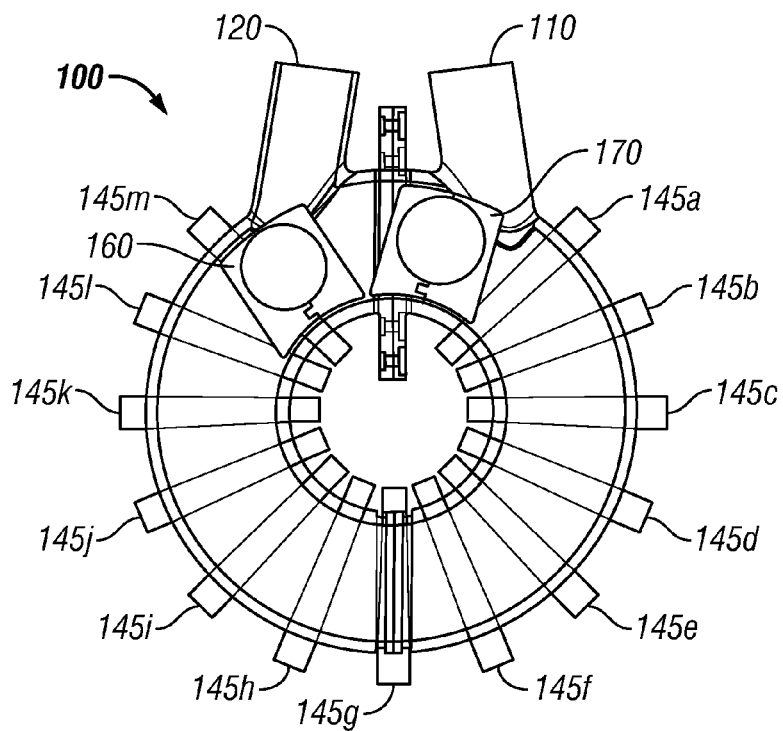
FIG. 11 is a section view of one embodiment of the present disclosure during operation.
Figure 12:
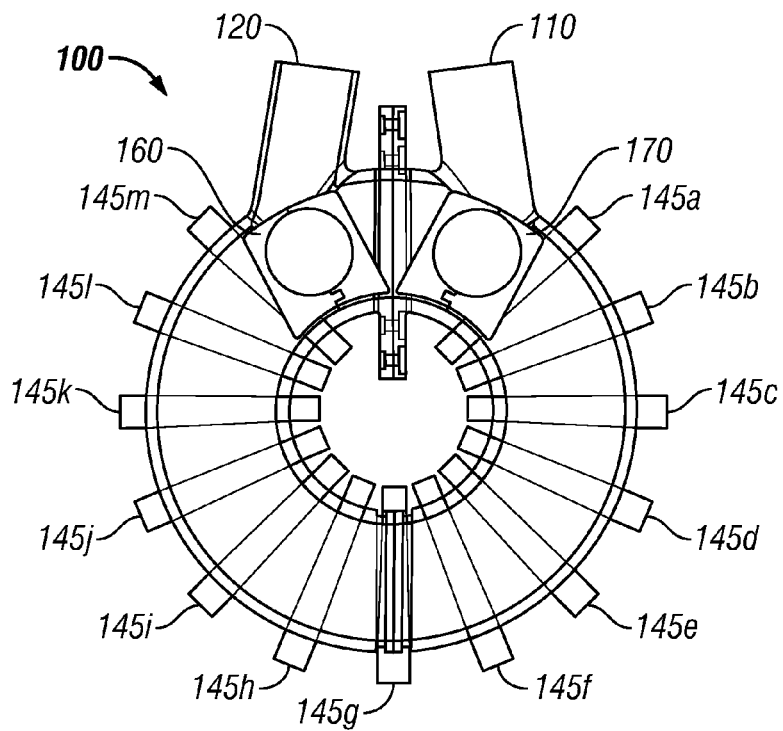
FIG. 12 is a section view of one embodiment of the present disclosure during operation.
Figure 13:
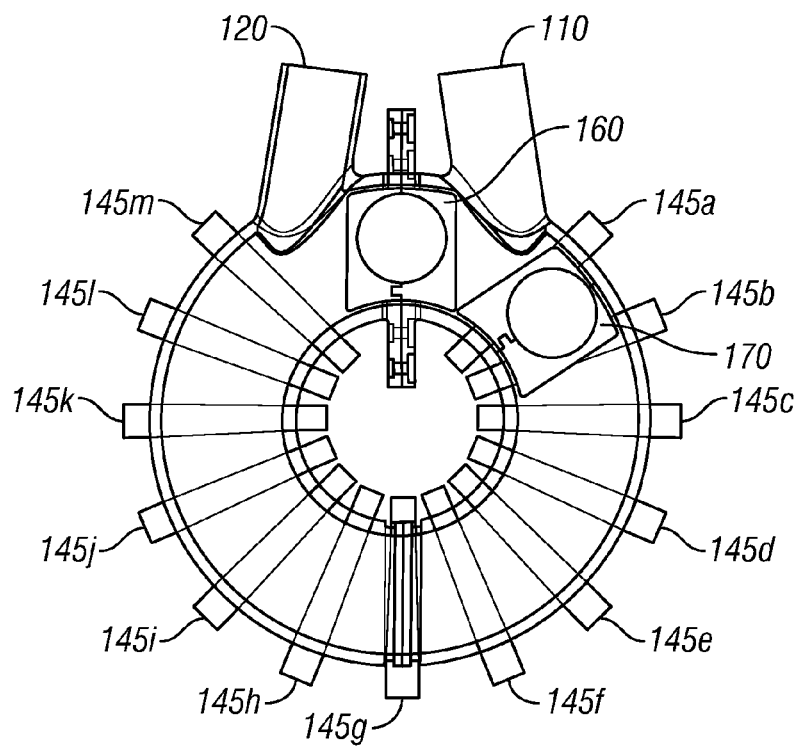
FIG. 13 is a section view of one embodiment of the present disclosure during operation.

FIGS. 8-13 show the progression of piston 160 around pumping chamber 130 during operation of pump 100. FIGS. 8-10 show the completion of the drive phase of the pump operation, in which piston 160 forces fluid to exit through outlet 120 and enter through inlet 110. FIGS. 11 and 12 show the transition phase of pump operation, in which piston 160 and piston 170 effectively switch functions. During this phase, piston 160 is transitioning from the "drive" piston to the "stationary" piston. Similarly, piston 170 is no longer stationary and is now being positioned for use as the drive piston. In FIG. 13, pump 100 has completed one cycle of operation and is ready to begin a second cycle, using piston 170 as the drive piston and piston 160 as the stationary piston. Pump 100 repeats the cycle described above during continued operation.

Referring back now to FIGS. 3-5, control system 111 uses knowledge of the instantaneous position of pistons 160, 170 and the absolute position of the coils (not shown) to make the decision of when to turn each solenoid 145 on and off and which direction to send the current while each solenoid 145 is on. The position of pistons 160, 170 is sensed by a single 2-axis Hall effect sensor 155 or a series of single axis Hall effect sensors 157 mounted around pumping chamber 130. Sensors 155, 157 sense the magnitude and direction of the magnetic field and relay this information as a voltage level to microprocessor 102 which translates this data through a conversion algorithm into the angular positions of pistons 160, 170. Following a programmed algorithm, microprocessor 102 then outputs an array of digital signals to a plurality of driver circuits 103. In a preferred embodiment, each driver circuit 103 is comprised of a full-bridge configuration of MOSFETs connected to a single solenoid and a power supply. This full-bridge MOSFET configuration can be found prefabricated on an integrated circuit chip such as the L298 produced by ST electronics. Upon receiving the appropriate digital signal from microprocessor 102, driver circuit 103 places the voltage of power supply 101 in a forward or reverse bias direction across the terminals of a solenoid 145. Driver circuit 103 can also remove the voltage from the terminals of the solenoid 145 when microprocessor 102 directs the solenoid 145 to be turned off. Microprocessor 102 can send either TTL or pulse width modulated signals to driver circuit 103 to control the direction and magnitude of the current delivered to the solenoid 145. It should be appreciated that the level of current that is delivered to the solenoid 145 can be used to control the drive piston at variable speeds. Flyback diodes are used to prevent current spikes from damaging the MOSFET chip due to the high inductance of the solenoid 145.

Referring additionally to FIGS. 7-12, while piston 160 is being driven around pumping chamber 130, piston 170 is held in place by attractive and repulsive forces created by solenoids 145a and 145m. The direction and magnitude of the currents delivered to solenoids 145a and 145m is controlled by control system 111 such that the forces the piston 170 experiences from pressure differences across its two faces are canceled by the solenoid forces, resulting in a zero net force on the 170 piston, which makes it remain stationary. A simple feedback loop is used in the microprocessor 102 to deliver the correct currents to keep it held in place. For instance, this can be accomplished in some cases by repelling the piston 170 with both solenoids 145*a* and 145*m*, effectively trapping piston 170 in position.

Solenoids 145*b* through 145L drive the piston 160 in a clockwise rotation around pumping chamber 130 while the piston 170 is held in place. In this fashion, the bolus of fluid that originally existed between the leading face of the piston 160 and the trailing face of the piston 170 is effectively ejected from the pump through outlet 120. Likewise, a fresh bolus of fluid enters the lumen through inlet 110 by means of a vacuum force that arises by the expanding volume generated between the lagging face of the piston 160 and the leading face of piston 170. In this fashion, piston 170 is isolated and acts as an isolation member or a virtual "valve" in the sense that it prevents fluid from flowing from the high pressure side to the low pressure side of pumping chamber 130. It should be appreciated that the angle of the piston faces and the angle and shape of inlet 110 and outlet 120 are designed to provide a smooth transition of the fluid into and out of pump 100 without causing turbulence, eddies, stagnation points, or shearing stresses sufficient to damage delicate fluid particles.

As the piston 160 nears the end of the drive stroke it comes into close contact with the piston 170. At this point the drive phase has ended and the transition phase begins. During the transition phase piston 160 and piston 170 move together in a clockwise direction until the piston 160 resides in the isolation position where the piston 170 previously resided, located substantially between inlet 110 and outlet 120 and the piston 170 resides in the position to begin the drive phase. Control system 111 can achieve this synchronized jog of both pistons 160, 170 in one embodiment by controlling solenoid 145*a* to attract the second piston and directing solenoid 145*m* to repel the first piston. Once pistons 160, 170 have completed this transition phase piston 170 is now in position to execute the drive stroke of the drive stage and piston 160 is positioned to be isolated between inlet 110 and outlet 120 to provide proper occlusion. It is in this way that each piston alternates being the driven piston and the isolated or stationary piston. The speed at which each of these cycles is performed, controlled by the magnitude of currents delivered to solenoids 145*a*-145*m*, dictates the flow rate of pumping. It is important to note that this is a positive displacement pump in the sense that the displacement of the drive piston is proportional to the displacement of fluid that enters and leaves the pumping chamber. In this way the pump is largely capable of delivering pulsatile outputs by ejecting discrete boluses of fluid.

In the embodiment shown, the movement of fluid was from inlet 110 to outlet 120 through the clockwise actuations of drive piston 160. However, it should be appreciated that the pumping direction is easily reversed by actuating the pistons in a counterclockwise fashion and performing a similar set of steps.

Figure 13A:
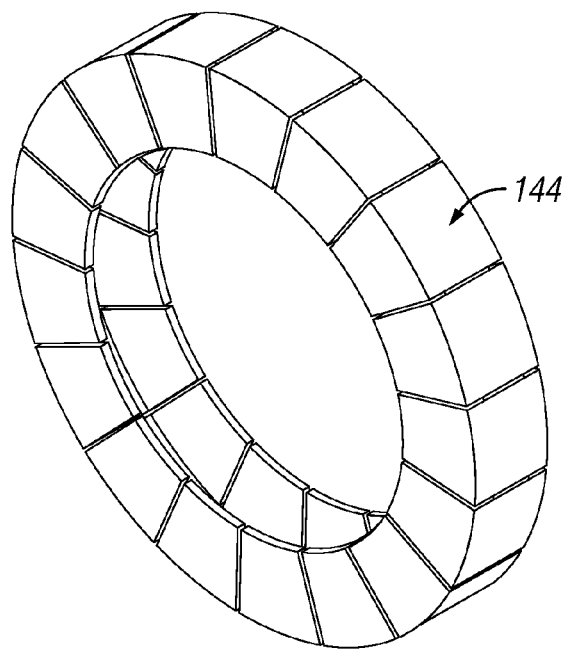
FIG. 13A is a perspective view of magnetic shielding clips used in certain embodiments of the present disclosure.
Figure 13B:
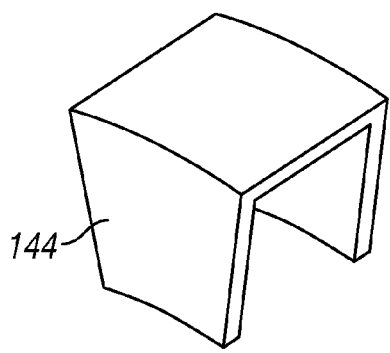
FIG. 13B is a perspective view of a magnetic shielding clip used in certain embodiments of the present disclosure.

Referring now to FIG. 13A, a plurality of magnetically permeable shrouding clips 144 are shown arranged in a circle. In certain embodiments, shrouding clips 144 are positioned around solenoids 145 (shown in FIGS. 1 and 2) for increasing and ducting magnetic flux towards pistons 160 and 170, resulting in improved force transduction and higher efficiencies. As shown in FIG. 13A, discrete spacing of shrouding clips 144 provides air gaps for the prevention of eddy current generation. FIG. 13B illustrates a detailed view of a shrouding clip 144.

Figure 14:
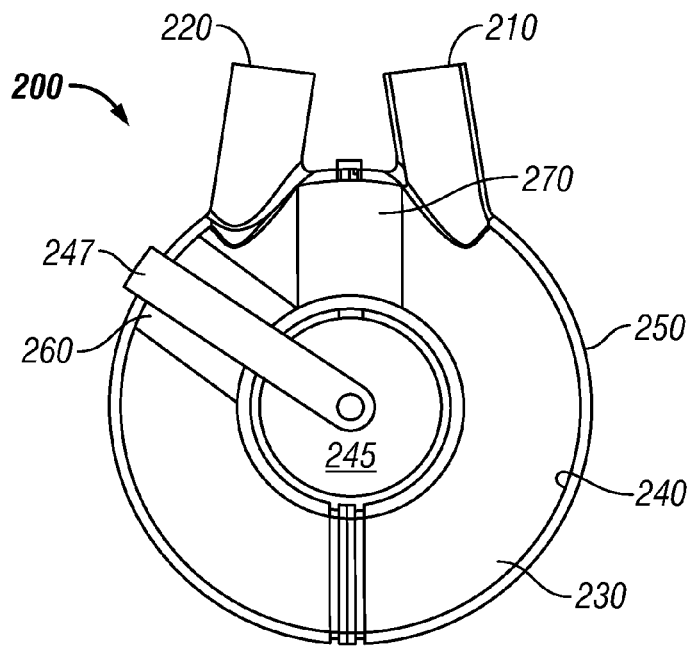
FIG. 14 is a side view of one embodiment of the present disclosure.
Figure 15:
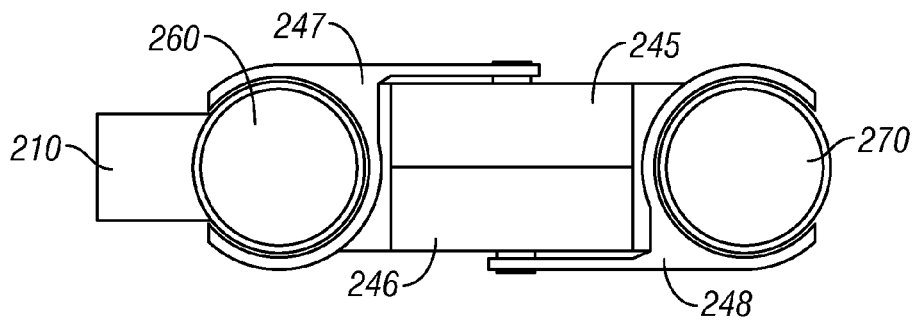
FIG. 15 is a section view of the embodiment of FIG. 14.

FIGS. 14-15 show an additional embodiment comprising an alternative means for actuating and holding the pistons within the pumping chamber. In this embodiment, a pump 200 comprises an inlet 210, an outlet 220, a pair of pistons 260, 270 and a pumping chamber 230 with an inner wall 240 and an outer wall 250. Pump 200 further comprises a pair of DC pancake torque motors 245, 246 located in the void at the center of pumping chamber 230. It should be appreciated that a variety of motor types could be used including alternating current motors, direct current motors, stepper motors, induction motors etc. Each motor 245, 246 has a cylindrical shape. Electric motor 245 is positioned above the electric motor 246 such that the two motors share a common plane. Each electric motor 245, 246 has a rotor (not shown) and an arm extending from the rotor towards outer wall 250 of pumping chamber 230. A first arm 247 is connected to the first rotor through a press fit on the shaft of the rotor and a hole on arm 247. The distal end of arm 247 takes the shape of crescent so that arm 247 wraps around a portion of outer wall 250 of pumping chamber 230 leaving space so as not to interfere with inlet 210 and outlet 220 of pumping chamber 230. The distal end of arm 247 is comprised either wholly or partially of a magnetic material so that a magnetic force is transferred between the distal portion of arm 247 and magnetic piston 260 residing within the lumen of pumping chamber 230. Second arm 248 is similarly connected to the second rotor (not shown) of second motor 246 and coupled magnetically to second piston 270. However motor 246 is oriented such that arm 248 is located on the opposite side of pump 200 from first arm 247 so that each arm 247, 248 does not interfere with the other.

In the embodiment shown in FIGS. 14-15, arms 247, 248 magnetically couple to pistons 260, 270, respectively, within the lumen of pumping chamber 230 with sufficient magnetic force such that an angular displacement of each arm 247, 248 moves its coupled piston by the same angular amount. In this way, each motor 245, 246 is able to control the precise location and motion of the internal pistons 260, 270 through the rotation of each arm 247, 248. Pumping of fluid is achieved with the similar piston motion as described in the solenoid actuated piston embodiment. In order to achieve this piston motion, each motor is controlled by a control circuit (not shown) similar to that previously described to either rotate its coupled piston or to hold it stationary. The microcontroller thus controls arms 247, 248 to perform the motion described previously to achieve the expulsion of fluid from the lumen through outlet 220 and the refilling of the lumen through inlet 110.

Figure 16:
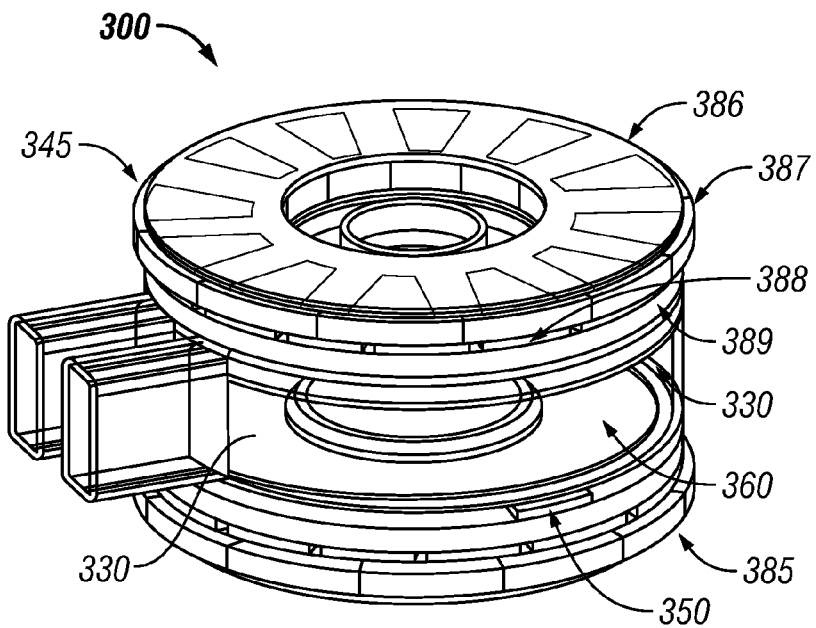
FIG. 16 is a perspective view of one embodiment of the present disclosure.
Figure 17:
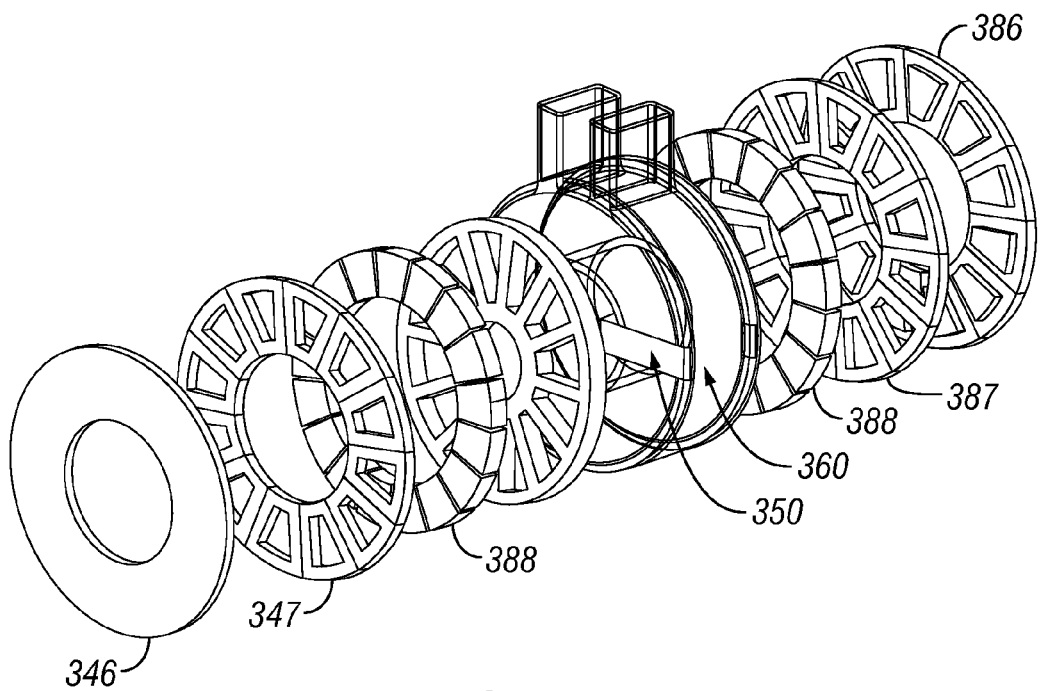
FIG. 17 is an exploded view of the embodiment of FIG. 16.

Referring now to FIGS. 16-17 another embodiment comprises a pump 300 with a pair of electric motors 345, 385 having a different configuration than motor 245, 246 of FIGS. 14-15. In this embodiment, electric motors 345, 385 are not located within the void at the center of the pumping chamber 330, but instead are adjacent to pumping chamber 330. Electric motor 345 comprises a coil core plate 346, coils 347, magnets, 348, and a magnet core plate 349. Similarly, electric motor 385 comprises a coil core plate 386, coils 387, magnets 388, and a magnet core plate 389. Linkage 350 couples either electric motor 345 or 385 with magnetic piston 360. For purposes of clarity, FIGS. 16-17 show only one piston 360; however, an additional piston can be incorporated in this embodiment so that one piston acts as a driving piston and the other piston acts as a stationary piston. The operation of this embodiment is similar to that of previously-described embodiments.

Figure 18:
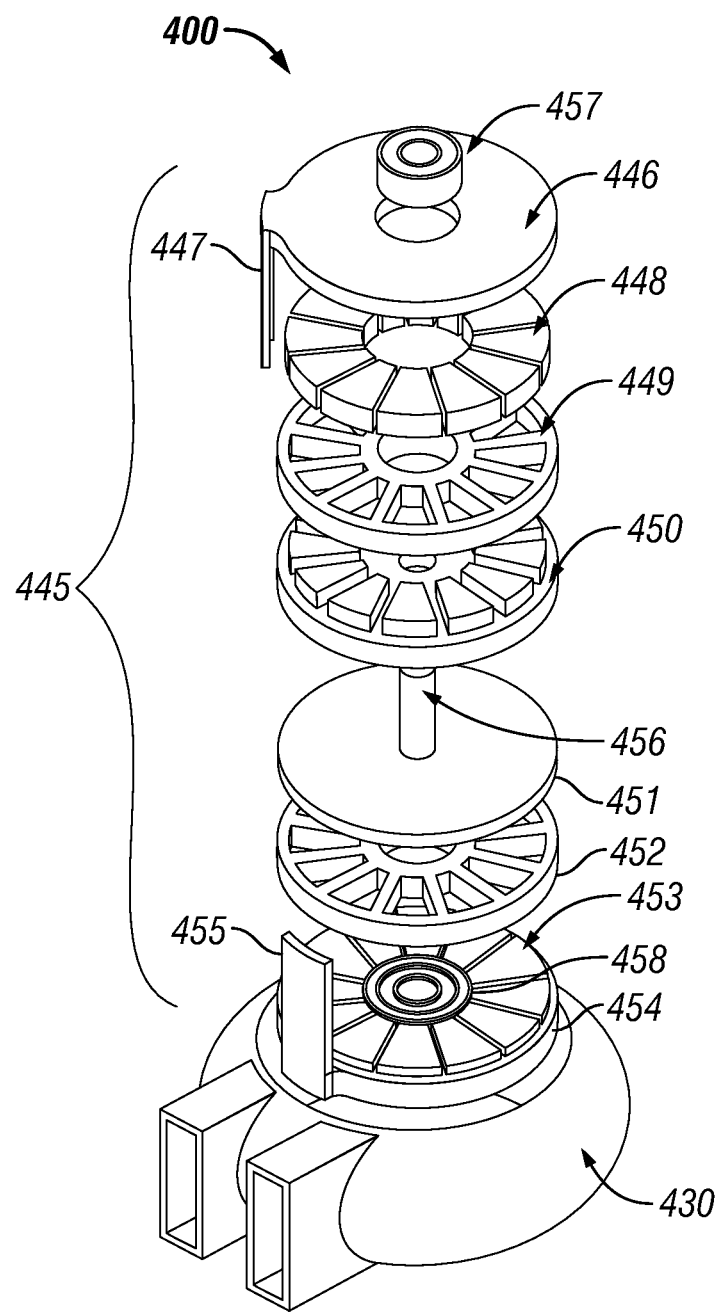
FIG. 18 is an exploded view of one embodiment of the present disclosure.

FIG. 18 shows yet another embodiment comprising a pump 400 with a pumping chamber 430, a motor 445 and a pair of pistons (not shown). In this embodiment, motor 445 comprises a first magnet core plate 446 with a first linking arm 447, a first plurality of magnets 448, a first coil 449, a first coil core plate 450, a second coil plate 451, a second coil 452, a second plurality of magnets 453, and a second magnet core plate 454 with a second linking arm 455. Motor 445 further comprises a shaft 456, a first bearing 457 and a second bearing 458. Although motor 445 is configured differently than the motors described in the discussion of previous embodiments, the embodiment of FIG. 18 operates in a manner similar to the previously-described embodiments.

Figure 19:
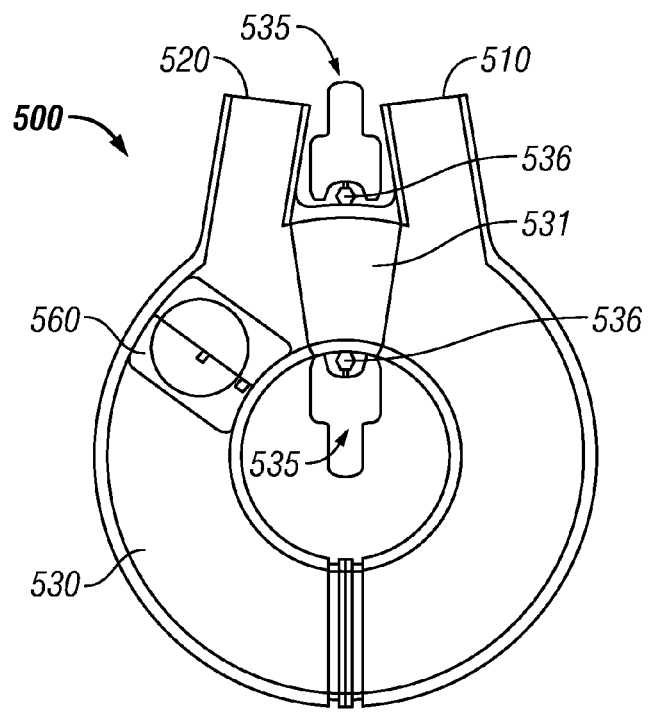
FIG. 19 is a section view of one embodiment of the present disclosure.
Figure 20:
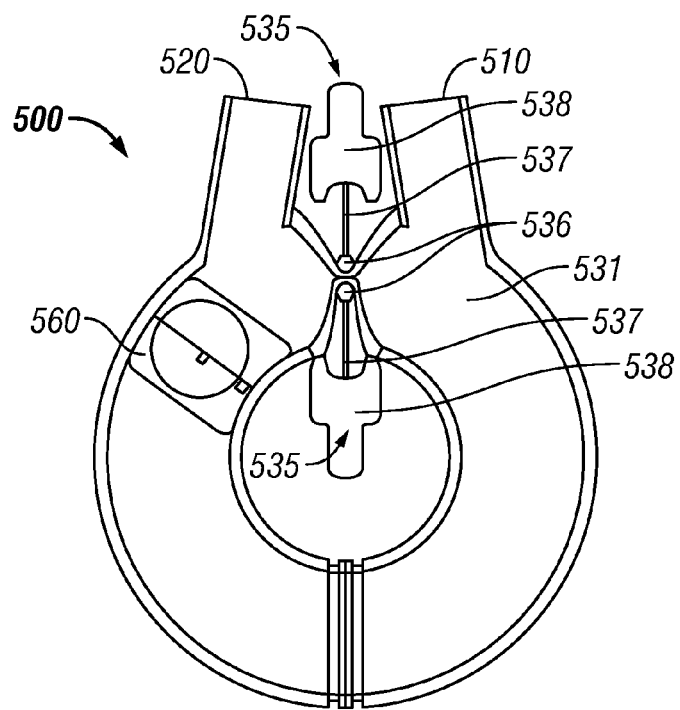
FIG. 20 is a section view of the embodiment of FIG. 19.

FIG. 19-20 shows a section view of another embodiment. In this embodiment, a pump 500 comprises a piston 560 and a pumping chamber 530 with an inlet 510 and outlet 520. Pumping chamber 530 further comprises an elastic segment 531 that extends between inlet 510 and outlet 520. A pinch valve 535 acts as an isolation member and is positioned about elastic segment 531. In this embodiment the pinch valve comprises a pair of rollers 536 positioned opposite each other with elastic segment 531 positioned in between rollers 536. Rollers 536 reside on a pair of rods 537. Rods 537 are mounted inside pinch valve housing 538, which contains an actuator for actuating and holding rods 537 at precise positions. This actuator can be electromagnetic, hydraulic, mechanical, etc.

The operation of pump 500 involves the use of pinch valve 535 to substantially occlude the fluid flow between inlet 510 and outlet 520. Pinch valve 535 eliminates the need for the stationary piston utilized in previously described embodiments. Use of pinch valve 535 further eliminates the need for the extra solenoids or an extra motor which are necessary to drive the second piston in other embodiments. In the embodiment of FIGS. 19-20, pinch valve 535 actuates elastic segment 531 of pumping chamber 530 such that the elastic segment 531 can be open or closed. When elastic segment 531 is open, drive piston 560 freely passes through elastic segment 531. When elastic segment 531 is closed, neither fluid nor piston 560 can pass through elastic segment 531. During operation, drive piston 560 is actuated in a clockwise fashion by either type of actuation means previously described (solenoids or motor) or a similar actuation means. As drive piston 560 is actuated, pinch valve 535 remains closed, clamping down on elastic segment 531 to prevent the flow of fluid through elastic segment 531. In essence, pinch valve 535 acts similar to a secondary piston suspended in the isolation position described previously. As drive piston 560 is actuated, fluid enters the pump in the expanding volume created behind its lagging face and fluid exits through outlet 520 by means of the pressure created between the leading face of drive piston 560 and pinch valve 535. The only time elastic segment 531 is actuated to open is at the completion of the drive phase when drive piston 560 passes through elastic segment 531. At all other times elastic segment 531 is pinched shut, so as to act as a valve prohibiting the flow of fluid through the segment. During the transitional phase pinch valve 531 is directed by the control system (not shown) to open. A sensor array similar to previously described embodiments is used to detect the position of the drive piston and signal when it is appropriate to open pinch valve 535. A driver circuit (not shown) then delivers current to a set of solenoids (also not shown) within pinch valve housing 538 which exert a force on rods 537 of pinch valve 535 such that they are pulled away from each other, thus opening elastic segment 531. In this embodiment, rods 537 are electromagnetically actuated, but it should be appreciated that they could also be mechanically or hydraulically actuated to cause the elastic segment 531 to expand and collapse (i.e., open and close). It should be further appreciated that elastic segment 531 is easily deformed by external forces and can be quickly pinched shut so that fluid is substantially occluded through arc segment 531. The elastic material is also sufficiently elastic to expand back into its original shape if external forces are removed. It should also be appreciated that an elastic polymer is used as the arc segment that will not deteriorate or fatigue from prolonged deformation cycles. After drive piston 260 passes through elastic segment, 531 the microprocessor (not shown) directs the drive system to actuate pinch valve 535 to close. After pinch valve 535 closes, the system is ready to perform another pumping stroke. In this fashion, pumping strokes are repetitively performed to achieve the pumping of fluid.

Figure 21:
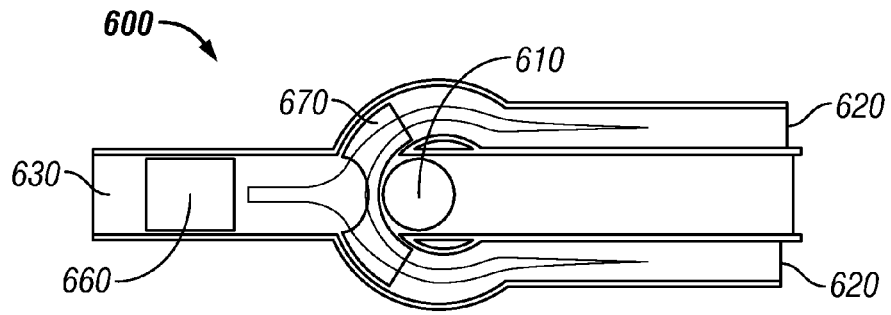
FIG. 21 is a section view of one embodiment of the present disclosure.
Figure 22:
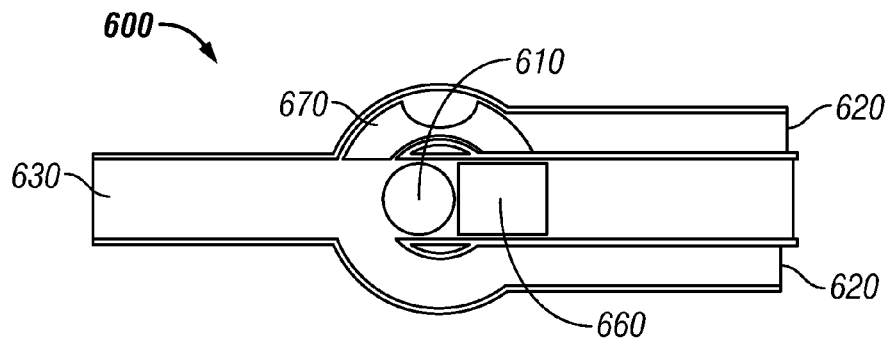
FIG. 22 is a section view of the embodiment of FIG. 21.
Figure 23:
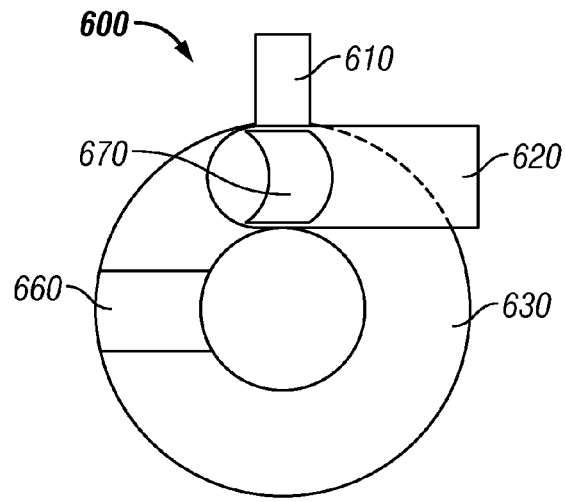
FIG. 23 is a side view of the embodiment of FIG. 21.

Referring now to FIGS. 21-23, an embodiment comprises a pump 600 with a pumping chamber 630 having an inlet 610 and an outlet 620. Pump 600 further comprises a drive piston 660 and an isolation member or isolation sleeve 670 that is hollow and curved in shape. FIGS. 21 and 22 show pump 600 from a top view, while FIG. 23 displays pump 600 from a side view. As shown in FIGS. 21 and 22, fluid enters pump 600 orthogonally to the plane of rotation of isolation sleeve 670, through inlet 110 pointing into the page. When drive piston 660 is detected, the isolation sleeve 670 is electromagnetically actuated to recess into the outlet 620 to allow piston 660 to pass, as shown in FIG. 22. Actuation is achieved by electromagnets, which are positioned external to the torus or pumping chamber 630 and generate a force on magnetic material imbedded within isolation sleeve 670. Once piston 660 passes, isolation sleeve 670 returns to the configuration shown in FIG. 21. Pump 600 is configured so that the structure of pumping chamber 630 and isolation sleeve 670 bear the load created by the fluid pressure differential across valve sleeve 670. By utilizing the pump's structure to bear the static load, pump 600 does not require electromagnetic energy to maintain isolation sleeve 670 is a fixed position.

Figure 24:
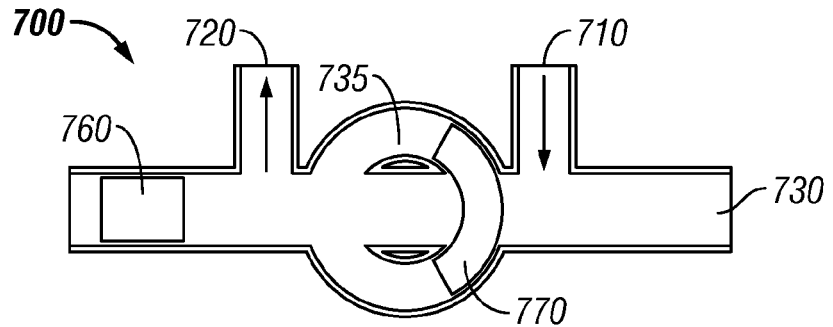
FIG. 24 is a section view of one embodiment of the present disclosure.
Figure 25:
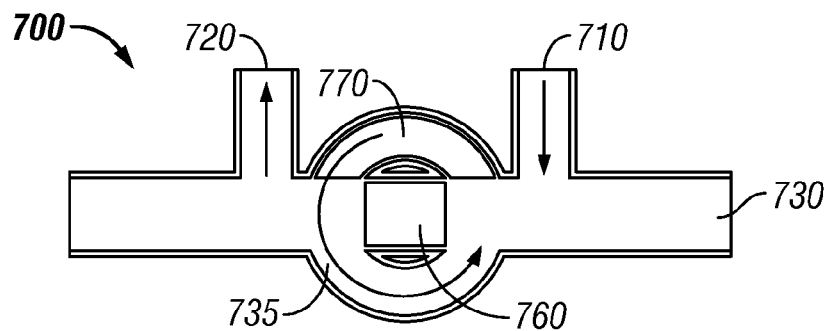
FIG. 25 is a section view of the embodiment of FIG. 25.

Another embodiment is shown in FIGS. 24-25 comprising a pump 700 with a pumping chamber 730, a recess 735, an inlet 710, and an outlet 720. Pump 700 further comprises a piston 760 and an isolation piston 770. Pump 700 operates in a manner similar to the embodiment of FIGS. 21-23 by moving isolation piston 770 into recess 735. However, unlike isolation sleeve 670 of the embodiment in FIGS. 21-23, isolation piston 770 is solid rather than hollow isolation piston 770 can then rotate completely around recess 735 to flush out any fluid that stagnates during the pumping cycle.

Figure 26:
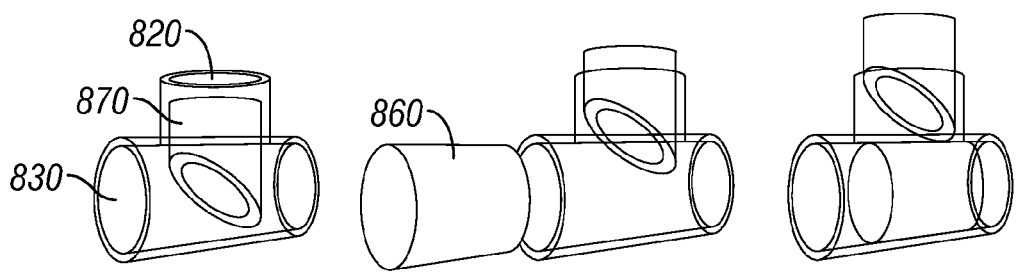
FIG. 26 is a view of one embodiment of the present disclosure in operation.

Another embodiment of an isolation mechanism is shown in FIG. 26. In this embodiment, a portion of a pumping chamber 830 is shown in fluid communication with a pump outlet 820. A drive piston 860 is propelled within pumping chamber 830 in a manner provided for in previous embodiments, such as solenoids or electric motors. In addition, a hollow isolation piston 870 is located in outlet 820. As drive piston 860 approaches outlet 820, hollow isolation piston 870 is retracted further into outlet 820 and away from pumping chamber 830. This allows drive piston to continue through pumping chamber 830 and begin a new pumping cycle. When hollow isolation piston 870 is in the position shown at the far left of FIG. 26, it allows fluid to exit outlet 820, but prevents fluid from bypassing outlet 820 and back flowing through an inlet (not shown, but connected to pumping chamber 830 downstream of outlet 820 so that drive piston 860 first passes by outlet 820 and then the inlet). In this manner, hollow isolation piston 870 functions similar to the occlusion devices described in the discussion of previous embodiments. In the embodiment shown, hollow isolation piston 870 is retracted into outlet 820 by the use of electromagnetic force. In other embodiments, the leading face of drive piston 860 can be tapered so that it engages the tapered end of hollow isolation piston 870 and forces hollow isolation piston 870 to recess into outlet 820.

Figure 27:
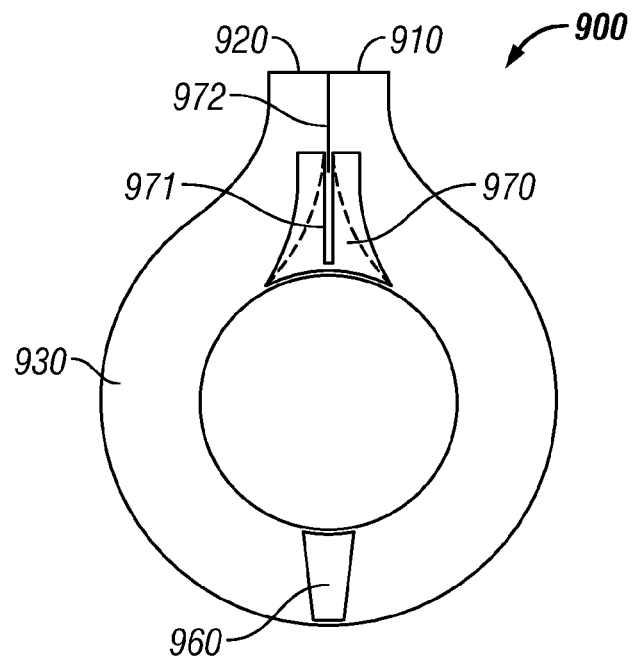
FIG. 27 is a section view of one embodiment of the present disclosure.
Figure 28:
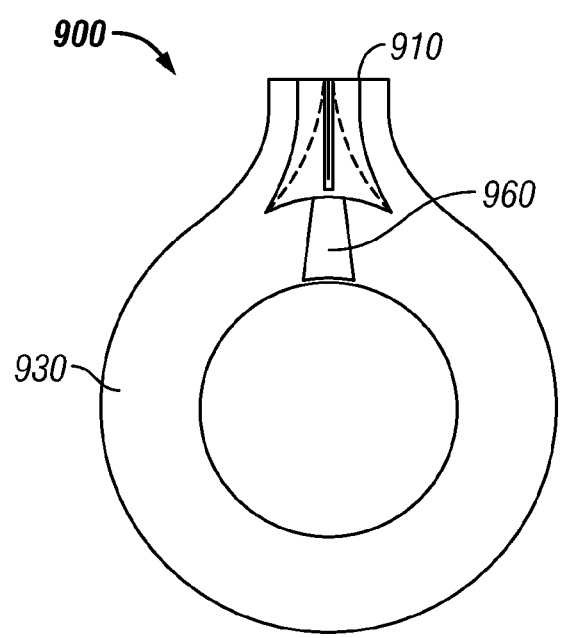
FIG. 28 is a section view of the embodiment of FIG. 28.

Another embodiment is shown in FIGS. 27-28. In this embodiment, a pump 900 comprises a pumping chamber 930, an inlet 910, an outlet 920, a drive piston 960, and an occlusion or isolation piston 970. The general principles of operation for pump 900 are similar to those of the previously described embodiments. However, in this embodiment, occlusion piston 970 comprises a slot 971 that engages a projection 972. The engagement of projection 972 and slot 971 provides for a structural load bearing mechanism to hold occlusion piston in place during the drive cycle of pump 900. As drive piston 960 approaches occlusion piston 970, occlusion piston 970 is withdrawn via electromagnetic or other suitable force, to allow drive piston 960 to pass.

Figure 29:
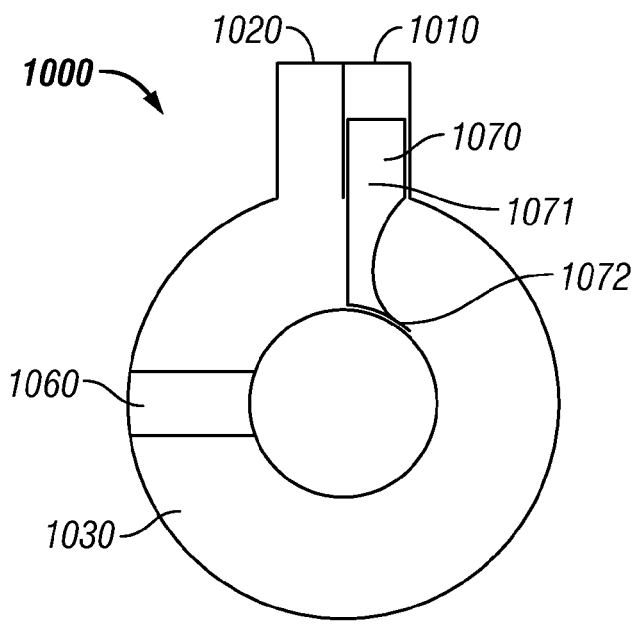
FIG. 29 is a section view of one embodiment of the present disclosure.
Figure 30:
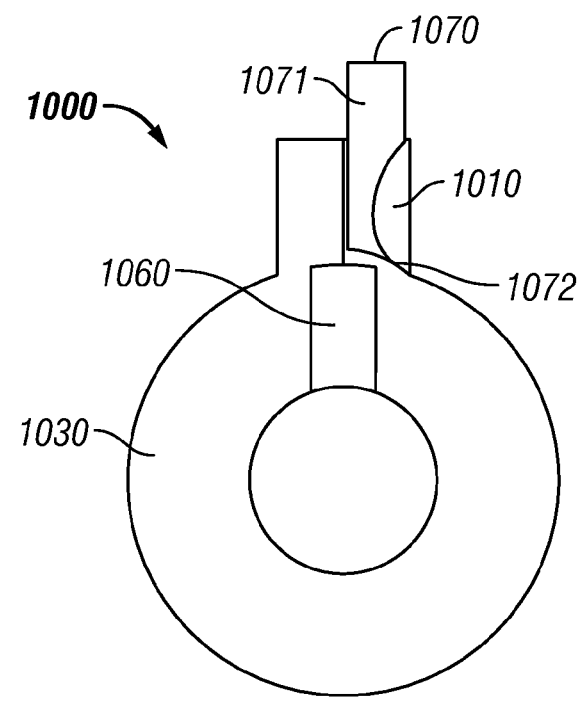
FIG. 30 is a section view of the embodiment of FIG. 29.

Another embodiment is shown in FIGS. 29-30. In this embodiment, a pump 1000 comprises an inlet 1010, an outlet 1020, a pumping chamber 1030, a drive piston 1060, and an isolation piston 1070. Pump 1000 operates in the same general manner as previously described embodiments, but incorporates isolation piston 1070 that has an upper hollow portion 1071 and a solid lower foot 1072. With this configuration, isolation piston allows fluid to enter pumping chamber 1030 when it is in the position shown in FIG. 29. In addition, solid lower portion 1072 seals off inlet 1110 when isolation piston 1070 is in the position shown in FIG. 30, thereby reducing backflow.

One advantage of recessing valve embodiments, such as those shown in FIGS. 21-29 is that each piston can be specifically designed for a single function instead of each piston having to take turns being either the drive piston or the isolation piston, thus sharing functions. By allowing for each piston to have a separate and individual function, each piston can be optimized to perform its function without making design concessions needed for the piston to serve both the drive and isolation functions. Specifically, the isolation piston can be designed to bear hydrostatic and dynamic fluid loads structurally to minimize the power consumed to occlude fluid flow. The isolation piston can also be shaped to provide smooth inflow and outflow fluid transition. The drive piston, relieved of its duty to act as an isolation piston every other cycle, can be optimized for a more continuous actuation cycle, low drag, and stability. The actuation and valving power can also be significantly reduced as compared to designs that require the control system to hold the isolation piston in place.

Figure 31:
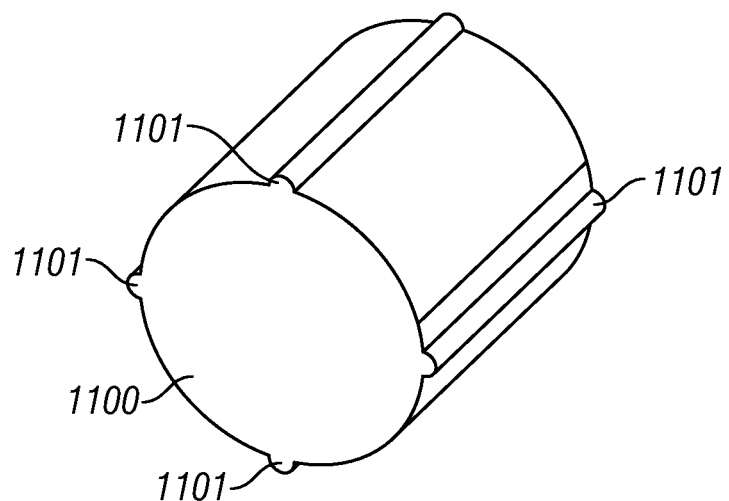
FIG. 31 is perspective view of a piston in one embodiment of the present disclosure.

Another embodiment of the present invention utilizes raised or grooved sections of the torus and/or pistons to control the position and the points where the piston contacts the inner torus wall. Referring now to FIG. 31, a piston 1100 comprise four raised ridges 1101. Ridges 1101 provide contact points with the torus wall (not shown in FIG. 31) that can be employed to minimize the contact area, decrease shearing stresses, decrease stagnation points, provide a controllable piston position, control the wear of the contact surface, and provide a lubricious sliding surface. Raised ridges 1101 may be comprised of a different material than the rest of piston 1100 and can be made of a ceramic or ultrahigh density polymer for favorable long term wear and lubricity characteristics.

Figure 32:
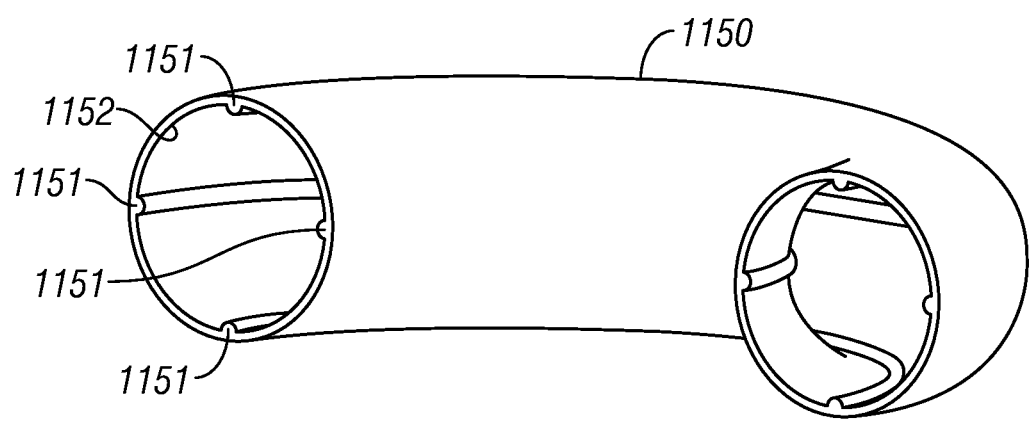
FIG. 32 is a section view of a component of one embodiment of the present disclosure.

Referring now to FIG. 32, another embodiment comprises ridges 1151 employed along an inner wall 1152 of a torus 1150. Ridges 1151 are similar to ridges 1101 in the previously described embodiment.

Figure 33:
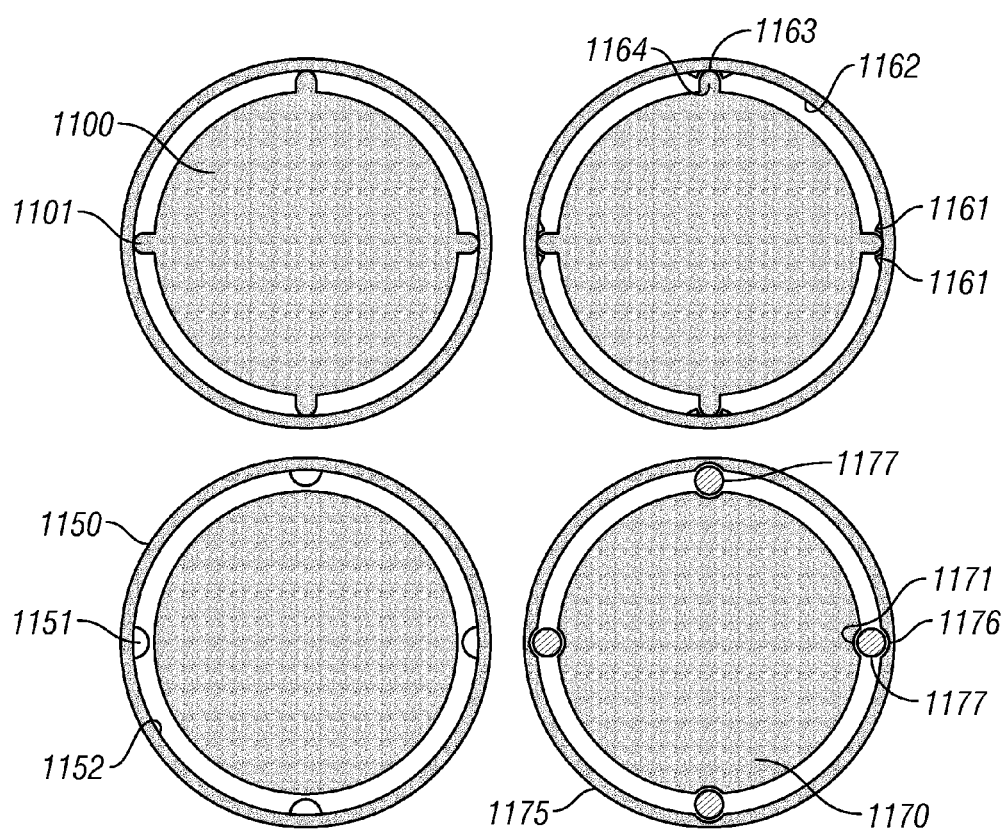
FIG. 33 is a section view of multiple embodiments of the present disclosure.

Additional embodiments shown in FIG. 33 show four configurations for piston wall contact ridges in cross section. In addition to the embodiments previously described in FIGS. 31 and 32, an embodiment comprises a torus 1160 that utilizes raised portions 1161 to create circumferential grooves 1163. In this embodiment, piston 1165 has ridges 1164 that engage grooves 1163.

Yet another embodiment comprises a piston 1170 with grooves 1171 and a torus 1175 with grooves 1176. This embodiment also includes ball bearings 1177 engaged with grooves 1171 and 1176, which provides a low friction surface contact.

Referring now to FIGS. 34A-34D, another embodiment of the present invention comprises a pump 1200 for the circulation of two independent circuits of fluid. In the embodiment shown, a toroidal pumping chamber 1250 contains three pistons 1210, 1211 and 1212 and has two inlet ports 1240, 1260 and two outlet ports 1270, 1280. The three pistons 1210-1212 are comprised of a magnetic material and can be actuated by a variety of means, including those previously described, such as a motor or electromagnets. The pumping of both chambers of fluid is performed in four steps. In the first step Piston 1212 is in a position 1 where it occludes fluid flowing through outlet port 1240. Piston 1210 is in position 2 and occludes fluid from flowing through inlet port 1240. Piston 1211 is positioned by electromagnets or other means (not shown) to reside in position 4 where it occludes fluid from flowing through inlet port 1240. The first bolus is pumped, as seen in the FIG. 34A by the actuation of piston 1210 from position 2 to position 3. During this actuation, fluid enters the chamber through inlet port 1240 and exits the chamber through port 1270, effectively pumping the chamber volume through port 1270 and refilling the chamber volume through port 1240. As seen in FIG. 34B, the next step, a transitional step, is performed by actuating piston 1212 to move from position 1 to position 2. In this position it now occludes inlet port 1240 and has opened outlet port 1280 for fluid transport. As seen now in FIG. 34C the third step in the pumping cycle is performed. In this step, the second chamber is pumped by the actuation of piston 31211 from position 4 to position 1. During this actuation the second chamber of fluid exits port 1280 and fluid refills the chamber behind piston 1212 by entering through port 4. Piston 1211 ends its actuation stroke at position 1 where it occludes port 1280. A second transitional step in FIG. 34D is then performed by actuating piston 1210 from position 3 into position 4 so that it occludes inlet port 1240. At the end of this transitional step, the pump has returned to its original state and is ready to perform the previous four steps again. In this way, two independent chambers of fluid may be pumped.

Figure 35:
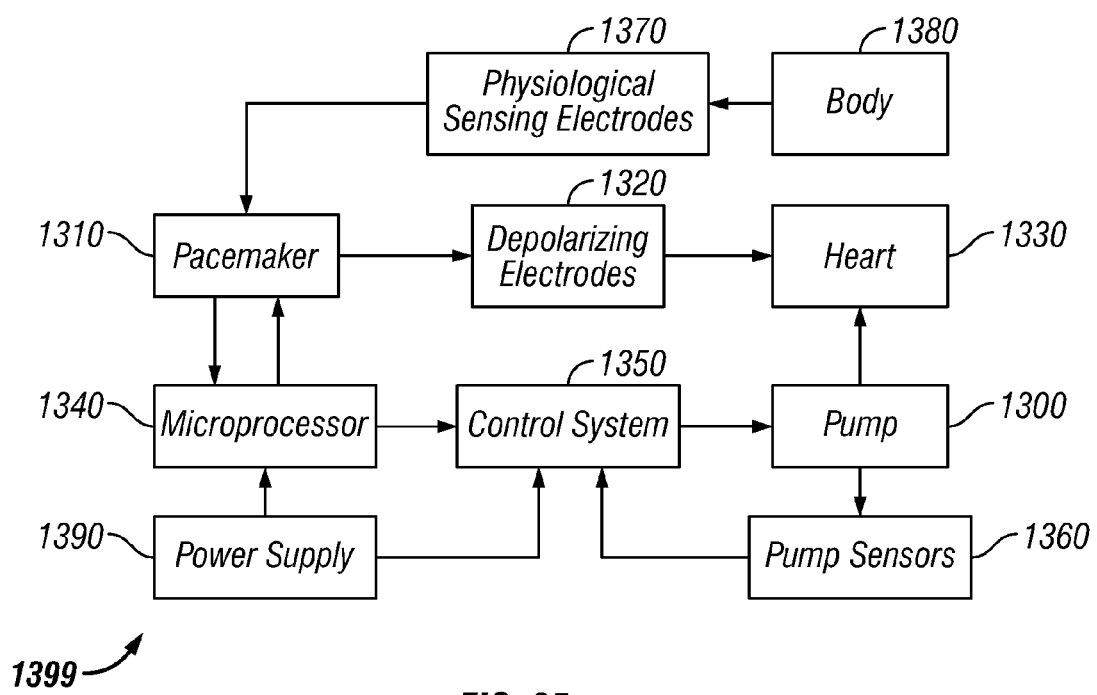
FIG. 35 is a schematic of an embodiment of the present disclosure.

The embodiment shown in FIG. 35 pertains to the use of a pacemaker 1310 connected to a pumping system 1399 in the application of ventricular assistance or biventricular cardiac pumping support. Many patients who suffer from congestive heart failure require ventricular assistance in the presence of a pacemaker. The embodiment of FIG. 35 illustrates a system that employs both a pump 1300 and the pacemaker 1310 that can control both the timing of the pump ejection and the timing of cardiac contraction. In this way the pump ejection can be timed to coincide with any particular part of the cardiac cycle. This is advantageous because synchronicity of pump ejection can greatly decrease the cardiac workload and can lead to healing of the damaged myocardium. A pacemaker is connected to a single or plurality of depolarizing electrodes 1320 that are inserted or attached to the native heart 1330. The pacemaker generates a depolarizing electric field at the electrode tip (not shown) that creates a depolarization of the myocardium resulting in contraction. The pacemaker generates these depolarizing stimuli at a periodicity that can be fixed or controlled either by pacemaker 1310 itself or by a microprocessor 1340 of pump system 1399. Pacemaker 1310 is electrically connected to microprocessor 1340 and information can flow freely between them. Microprocessor 1340 can direct pacemaker 1310 to change its periodicity of heart stimulation by means of a control signal. Likewise, the pacemaker can direct the microprocessor to cause the pump to eject by means of a control signal. Microprocessor 1310 is electrically connected to a control circuit or driver circuit 1350 which is connected to pump 1300. Pump 1300 is outfitted with one or more sensors 1360 which feedback position information to control circuit 1350 and which allows for proper actuation of the internal pistons (not shown) of pump 1300. Physiological sensing electrodes 1370 are connected to the patient's body 1380 and can be employed to measure changes in needed circulatory demand as the patient's activity level is changed. These physiological sensing electrodes 1370 can be made to measure a variety of metrics that indicate the need to increase or decrease heart rate such as the thoracic impedance, renal sympathetic nerve activity, aortic nerve activity, p-wave of the heart, acceleration of the body, or lactic acid levels. Upon receiving an input from physiological sensing electrodes 1370, pacemaker 1310 may increase or decrease its frequency of depolarization. This information may be relayed to microprocessor 1340 which could increase the rate at which the pump executes its pumping stroke in order to stay in sync with native heart 1330. Pacemaker 1310 can possess its own internal power supply such as a small battery (not shown) or can be powered by means of the same supply that drives the operation of pump 1300. Microprocessor 1340 is connected to a power supply 1390 which powers its internal circuits as well as directs power to pump 1300 when in operation.

Figure 36:
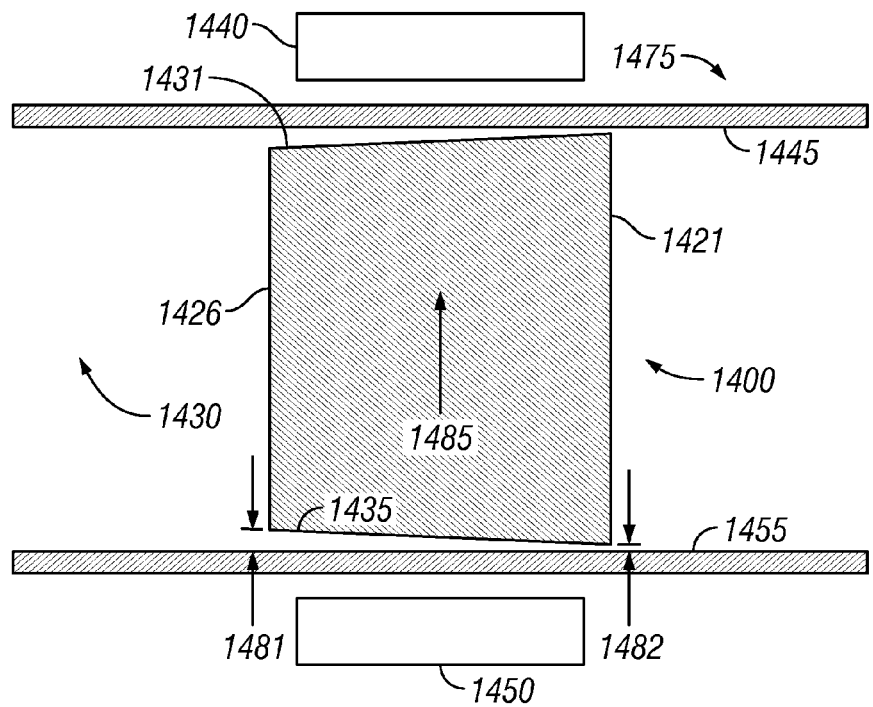
FIG. 36 is a partial side section view of an embodiment of the present disclosure.
Figure 37:
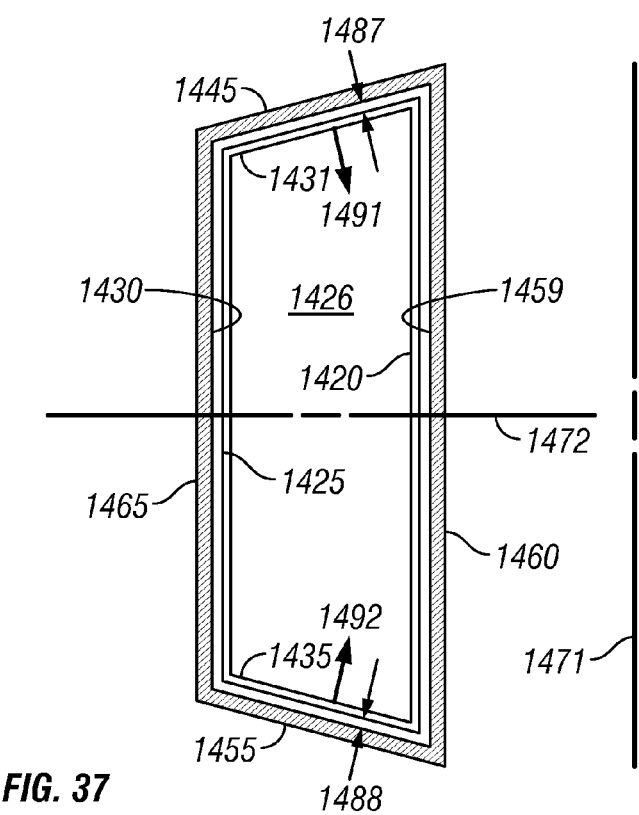
FIG. 37 is a partial end section view of the embodiment of FIG. 36.
Figure 38:
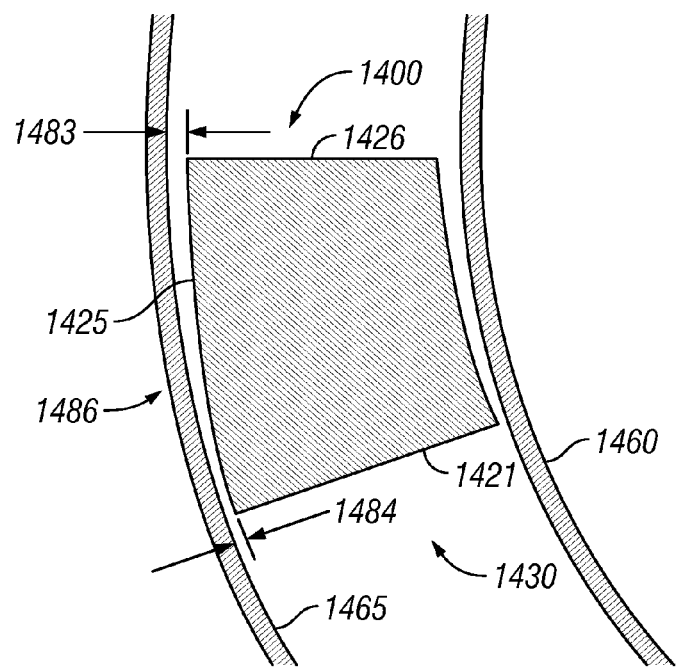
FIG. 38 is a partial top section view of the embodiment of FIG. 36.

Referring now to FIG. 36, a side section view illustrates one embodiment of a piston 1400 disposed within a pumping chamber 1430. In certain embodiments pumping chamber 1430 is configured as a torus (or any other continuous ring or loop). However, piston 1400 may be incorporated into any of the exemplary embodiments of pumps disclosed herein. In the embodiment shown, pumping chamber 1475 comprises an inner perimeter 1459 having an upper chamber wall 1445, a lower chamber wall 1455, an inner chamber wall 1460 and an outer chamber wall 1465. In the view shown in FIG. 36, piston 1400 is moving to the left within pumping chamber 1475, while in FIG. 37 piston 1400 is moving toward the viewer. Pumping chamber 1430 is centered on a central axis 1471, as shown in FIG. 37. FIG. 38 represents a top view of piston 1400, which is traveling up in this view. Piston 1400 comprises an inner surface 1420, an outer surface 1425, an upper surface 1431, a lower surface 1435, a leading face 1426 and a trailing face 1421. It is understood that the terms "upper", "lower", "inner" and "outer" are used herein as labels for convenience as shown in figures and not necessarily indicative of position during actual use. In general, inner surface 1420 is closer to central axis 1471 than is outer surface 1475. The terms "leading" and "trailing" are used to indicate the surfaces facing toward and away from the direction of piston travel, respectively. Upper surface 1431 and lower surface 1435 are adjacent to both leading and trailing faces 1426 and 1421 as well as inner and outer surfaces 1420 and 1425. In the embodiment shown, upper surface 1431 is proximal to upper chamber wall 1445, lower surface 1435 is proximal to lower chamber wall 1455, inner surface 1420 is proximal to inner chamber wall 1460, and outer surface 1425 is proximal to outer chamber wall 1465. Piston 1400 is magnetically coupled to upper magnetic linkage 1440 through upper torus wall 1445 and to lower magnetic linkage 1450 through lower chamber wall 1455.

In exemplary embodiments, one or more of inner surface 1420, outer surface 1425, upper surface 1431, and lower surface 1435 comprise a hydrodynamic bearing surface. In addition, a piston surface may comprise a hydrodynamic bearing surface which resists displacement in more than one axis. For example, as shown in the embodiment of FIGS. 36-38, upper surface 1431 and lower surface 1435 act as hydrodynamic bearings. In the primary direction of travel for piston 1400 (i.e., around pumping chamber 1475), hydrodynamic forces arise from the top and bottom surfaces which act to resist displacement of the piston towards the outer chamber wall as well as towards the upper and lower chamber walls.

Hydrodynamic bearing surfaces are incorporated on piston 1400 in order to offset forces (such as gravity, magnetic, and centrifugal forces) that would tend to bring piston 1400 into contact with pumping chamber 1475. By reducing the likelihood of contact between the piston and the chamber walls, shearing stresses can be greatly reduced and mechanical wear to the pistons and chamber walls can be prevented. Hydrodynamic bearing surfaces create "lift" (i.e. a force directing piston 1400 away from a stationary surface in a direction normal to the bearing surface) as piston 1400 moves within pumping chamber 1475. The hydrodynamic surfaces create lift by allowing a portion of fluid within pumping chamber 1475 to backflow across a surface of piston 1400 as it travels through the fluid and within pumping chamber 1475.

As shown in FIG. 36, upper and lower surfaces 1430 and 1435 are slightly angled so that the distance between upper surface 1435 and upper chamber wall 1445 decreases between leading face 1426 and trailing face 1421. It is understood that the Figures are not to scale, and that the angles of certain surfaces may be exaggerated to provide clarity. The distance between lower surface 1435 and lower chamber wall 1455 also decreases between leading face 1426 and trailing face 1421. As a result, the thickness of a fluid film between piston 1400 and lower chamber wall 1455 changes from a maximum lower film thickness 1481 to a minimum lower film thickness 1482. Under conservation of mass principles, with relative motion between lower surface 1435 and lower chamber wall 1455, the fluid between piston 1400 and lower chamber wall 1455 can create a hydrodynamic force (represented by arrow 1485) that acts on piston 1400 and directs it away from lower chamber wall 1455. As a result, friction or drag forces between piston 1400 and lower chamber wall 1455 and shearing stresses in the respective film layer are reduced. In certain embodiments, upper surface 1431 may also comprise a hydrodynamic bearing surface to produce a force directing piston 1400 away from upper chamber wall 1445. In this manner, upper and lower surfaces 1430, 1435 may be "tuned" so that piston 1400 should not contact either upper or lower chamber wall 1445, 1455 during normal operation. In still other embodiments, it may be possible to eliminate the hydrodynamic bearing surface on upper surface 1435 and allow gravity or magnetic link forces to repel upper surface 1435 from upper chamber wall 1445. However, because the ultimate orientation of a pump incorporating piston 1400 may not be known, it may be necessary to provide hydrodynamic bearing surfaces on both upper and lower surfaces 1430 and 1435.

Referring now to FIG. 38, a top view illustrates that leading face 1426 may be smaller than trailing face 1421. As a result, the distance between outer surface 1425 and outer chamber wall 1465 decreases from a maximum film thickness 1483 at leading face 1426 to a minimum film thickness 1484 at trailing face 1421. Under the same principles discussed in the description of FIG. 36, a hydrodynamic force (represented by arrow 1486) can be created to act on piston 1400 and direct it away from outer chamber wall 1465. Hydrodynamic force 1486 may be used to counteract the centrifugal force or magnetic link forces created during normal operation that tends to direct piston 1400 towards outer chamber wall 1465.

In addition, the gap between inner surface 1421 and inner chamber wall 1460 also may decrease between leading face 1426 and trailing face 1421 to create a hydrodynamic force to direct piston 1400 away from inner chamber wall 1460. However, because centrifugal force or magnetic link forces will direct piston 1400 away from inner chamber wall 1460 during operation (regardless of the orientation of the pump), it may not be necessary to include a hydrodynamic bearing surface on inner surface 1420.

Referring now to FIG. 37, an end section view of piston 1400 within pumping chamber 1475 is shown. As shown in this embodiment, upper surface 1431, lower surface 1435, upper chamber wall 1445 and lower chamber wall 1455 are not perpendicular to a plane that extends through central axis 1471 perpendicular to the page. Upper surface 1431, lower surface 1435, upper chamber wall 1445 and lower chamber wall 1455 are also angled relative to a plane extending through lateral axis 1472 perpendicular to the page. Therefore, as piston 1400 moves towards outer chamber wall 1465 (e.g., due to centrifugal force), an upper gap 1487 between upper surface 1431 and upper chamber wall 1445 (and a lower gap 1488 between lower surface 1435 and lower chamber wall 1455) will decrease. As the upper and lower gaps 1487, 1488 decrease, the pressure on a fluid between piston 1400 and upper and lower chamber walls 1445, 1455 will increase. As a result, a pair of forces (represented by arrows 1491 and 1492) acting on piston 1400 will be generated. Forces 1491 and 1491 each have a component that resists displacement of the piston 1400 towards outer wall 1465 and a component that resists displacement of piston 1400 towards the upper 1445 or lower 1455 chamber walls during operation.

While piston 1400 is illustrated in this embodiment with hydrodynamic bearing surfaces on upper surface 1431, lower surface 1435, inner surface 1420, and outer surface 1425, it is understood that other embodiments may comprise a piston with hydrodynamic bearing surfaces on fewer surfaces. For example, the hydrodynamic bearing surfaces may be eliminated on inner surface 1420 and outer surface 1425. In such embodiments, upper surface 1431 and lower surface 1435 may be configured as shown in FIGS. 36 and 37 to provide stabilization forces both laterally and vertically. As discussed in the description of FIG. 37, upper and lower surfaces 1430 and 1435 can be configured to generate forces 1491 and 1492 to balance the centrifugal and magnetic forces and therefore provide lateral stabilization. As a result it may not be necessary to provide hydrodynamic bearing surfaces on inner surface and outer surfaces 1420 and 1425. However, it may be desirable to provide hydrodynamic bearing surface on inner and outer surfaces 1420 and 1425 to provide additional forces directing piston 1400 away from inner wall 1421 and outer wall 1425. It should be understood that passive levitation of piston 1400 while it is moving can be achieved through use of hydrodynamic surfaces in this manner. Displacement of piston 1400 from its levitating position will increase hydrodynamic forces which act to resist the displacement and restore piston 1400 back to its levitating equilibrium position.

While exact dimensions will depend on numerous factors (such as the overall piston size and configuration, the fluid properties, etc.) in certain embodiments the minimum film thickness is approximately 0.00025-0.001 inches and the maximum film thickness is approximately 0.003-0.004 inches. Other factors, such as surface finish, may also affect the ability to generate hydrodynamic forces. In certain embodiments, the surface finish of piston 1400 and the interior walls of pumping chamber 1475 is between 1 and 16 microinches (as defined by the centerline average surface finish $R_a$).

Figure 39:
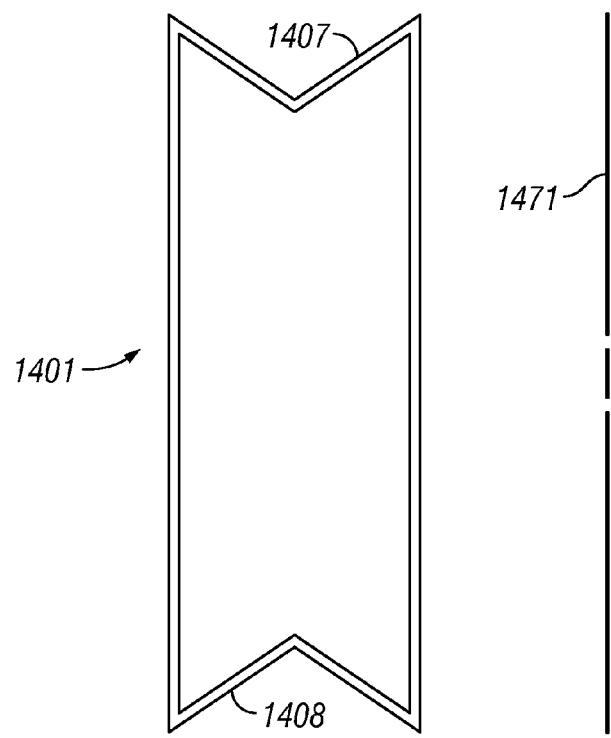
FIG. 39 is a partial end view of an embodiment of the present disclosure.
Figure 40:
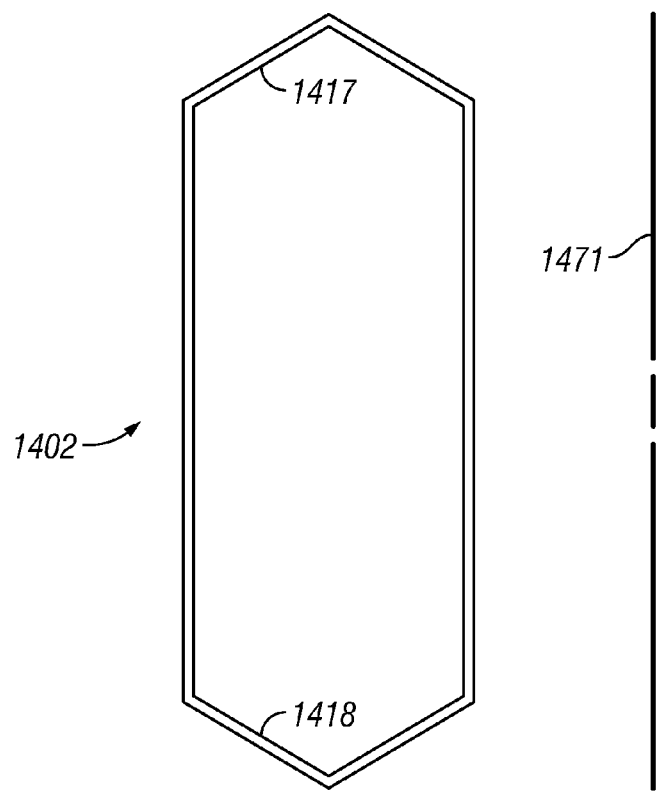
FIG. 40 is a partial end view of an embodiment of the present disclosure.
Figure 41:
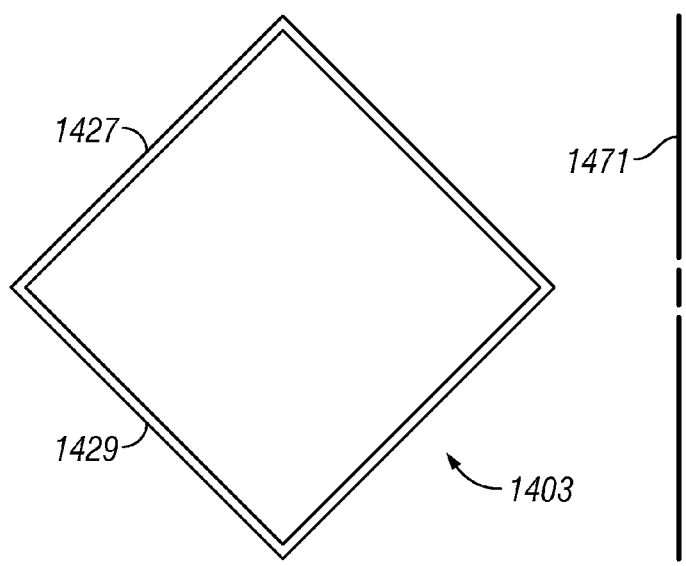
FIG. 41 is a partial end view of an embodiment of the present disclosure.
Figure 42A:
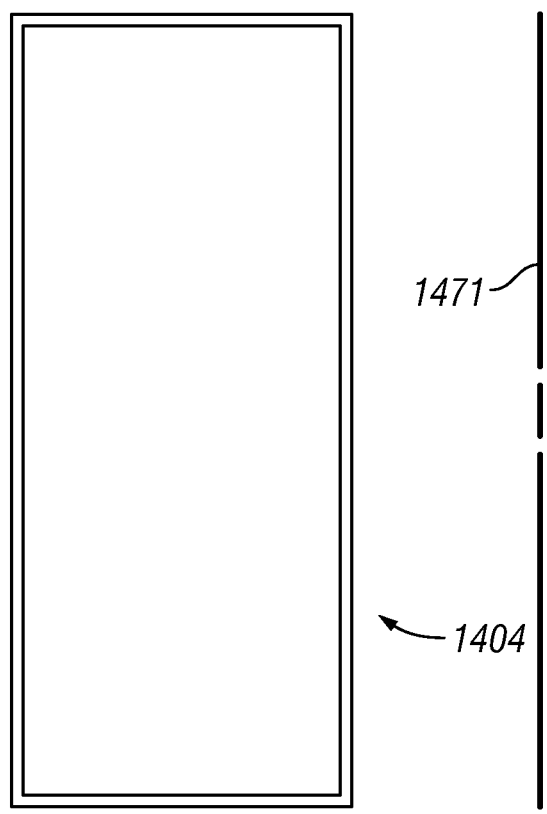
FIG. 42A is a partial end view of an embodiment of the present disclosure.

It is also understood that in certain embodiments a piston may comprise a cross-section different than piston 1400 shown in FIG. 37. Examples of various end views of exemplary pistons are provided in FIGS. 39-42A. As shown in FIG. 39, piston 1401 comprises an upper surface portion 1407 that is not perpendicular to axis 1471 and is angled down towards a lower surface portion 1408 (which is also not perpendicular to axis 1471 and is angled up towards upper portion 1407). Similarly, piston 1402 shown in FIG. 40 comprises an upper surface portion 1417 that is not perpendicular to axis 1471 and is angled down towards lower surface portion 1418 (which is not perpendicular to axis 1471 and is angled up towards upper surface portion 1417). As shown in FIG. 41, piston 1403 comprises an upper surface portion 1427 that is not perpendicular to axis 1471 and is angled down towards a lower surface portion 1428 (which is also not perpendicular to axis 1471 and is angled up towards upper portion 1427). In other embodiments, a piston may have a cross-section in which the entire upper or lower surfaces are perpendicular to the central axis of the pumping chamber. One example is shown in FIG. 42A, in which piston 1404 comprises a rectangular cross-section. Similar to the description of FIGS. 36-38, displacement of a piston 1401, 1402, 1403 or 1404 in any direction which results in a decrease in the distance between a piston surface and a chamber wall gives rise to hydrodynamic forces which resist this displacement and acts to restore the piston back to the equilibrium position. By reducing the likelihood of contact between the piston and the chamber walls, shearing stresses in the fluid are minimized.

Figure 42B:
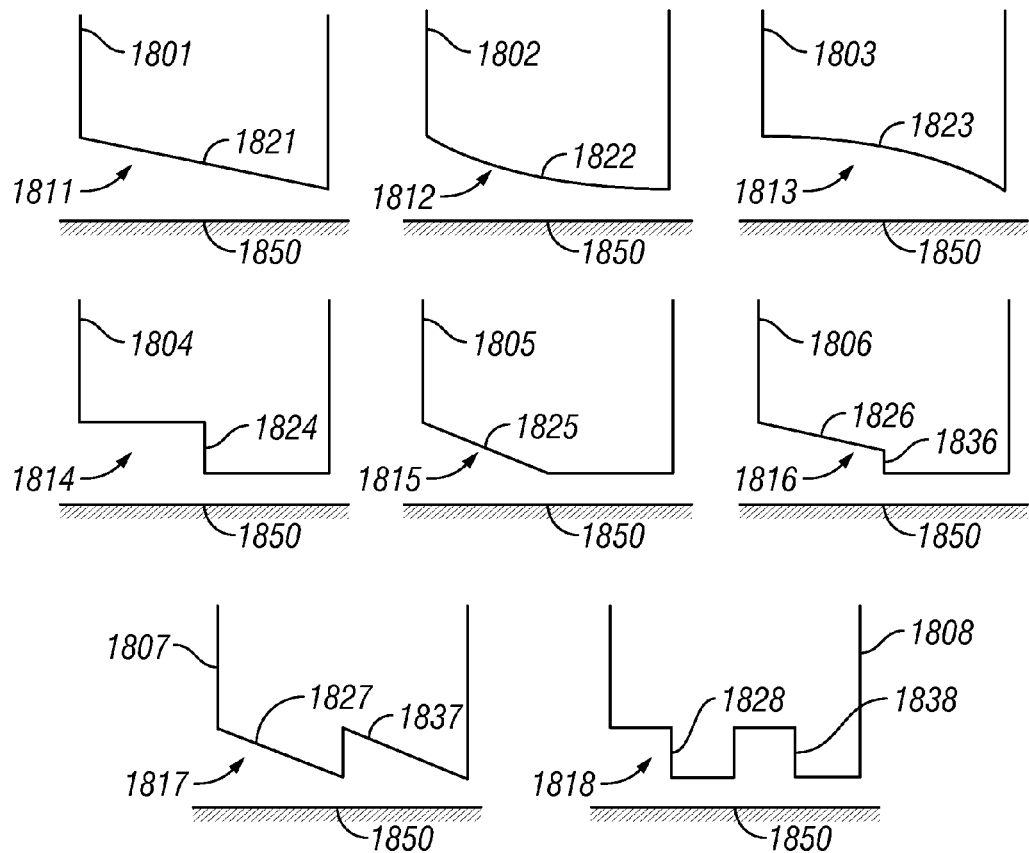
FIG. 42B is a partial side view of different embodiments of the present disclosure.

Referring now to FIG. 42B, detailed views of exemplary embodiments of hydrodynamic bearing surfaces are shown to comprise various different shapes. In the embodiments shown, a plurality of pistons 1801-1808 comprise a hydrodynamic bearing surface 1811-1818 proximal to a stationary surface 1850 (such as an inner surface of a pumping chamber). A first embodiment shows piston 1801 with hydrodynamic bearing surface 1811 comprising a tapered surface 1821 across piston 1801. In a second embodiment, piston 1802 comprises a hydrodynamic bearing surface 1812 that forms a convex curved surface 1822 across piston 1802. As shown, a third embodiment comprises piston 1803 with hydrodynamic bearing surface 1813 forming a concave curve surface 1823 across piston 1803. Referring now to piston 1804, hydrodynamic bearing surface 1814 comprises a single step 1824 proximal to stationary surface 1850. As shown on piston 1805, hydrodynamic bearing surface 1815 comprises an angled surface 1825 that extends partially across piston 1805. Piston 1806 comprises a hydrodynamic bearing surface 1816 that includes an angled surface 1826 and a step 1836. As shown on piston 1807, hydrodynamic bearing surface 1817 includes two separate angled surfaces 1827, 1837 with angled surface 1827 extending part of the way across piston 1807 and angled surface 1837 extending part of the way across piston 1807. Referring now to piston 1808, hydrodynamic bearing surface 1818 comprises a first step 1828 and a second step 1838. It is understood that each of the shapes shown in hydrodynamic bearing surfaces 1801-1808 are merely examples of a multitude of different configurations that can be used to create hydrodynamic bearing surfaces. A hydrodynamic bearing may comprise any surface configured to create "lift" by allowing fluid backflow between stationary and moving surfaces that are proximal to each other. Backflow occurs when a portion of the fluid moves against the predominant direction of fluid flow (e.g., in a direction from the trailing face towards the leading face.)

Figure 42C:
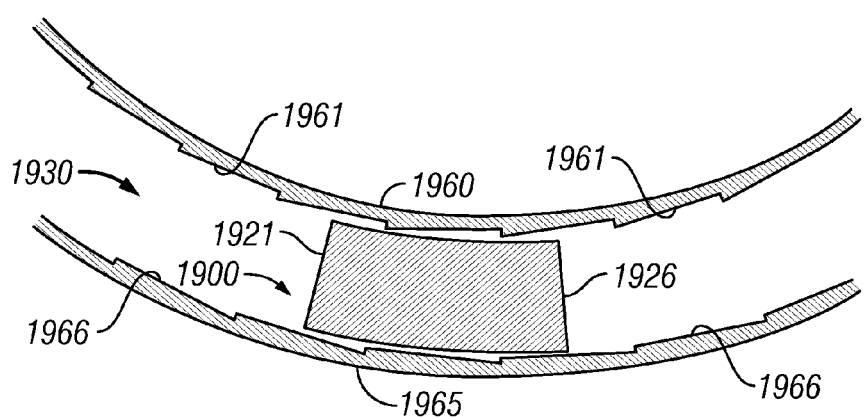
FIG. 42C is a partial top view of an embodiment of the present disclosure.

Furthermore, exemplary embodiments may comprise hydrodynamic bearing surfaces on stationary components. Referring now to FIG. 42C, one exemplary embodiment comprises a piston 1900 disposed within a pumping chamber 1930 comprising an inner wall 1960 and an outer wall 1965. In the embodiment shown, piston 1900 comprises a leading face 1926 and a trailing face 1921, as piston 1900 moves toward the right. Inner wall 1960 comprises a plurality of tapered surfaces 1961 that act as hydrodynamic bearing surfaces when piston 1900 moves relative to tapered surfaces 1961. Similarly, outer wall 1965 comprises a plurality of tapered surfaces 1966 that act as hydrodynamic bearing surfaces when piston 1900 moves relative to tapered surfaces 1966. In this embodiment, the same principles of operation used to create "lift" apply as those described in embodiments with hydrodynamic bearing surfaces placed on moving components. It is understood that while inner wall 1960 and outer wall 1965 are shown to comprise angled surfaces, other embodiments may comprise different configurations (for example, similar to those described in FIG. 42B).

Figure 43:
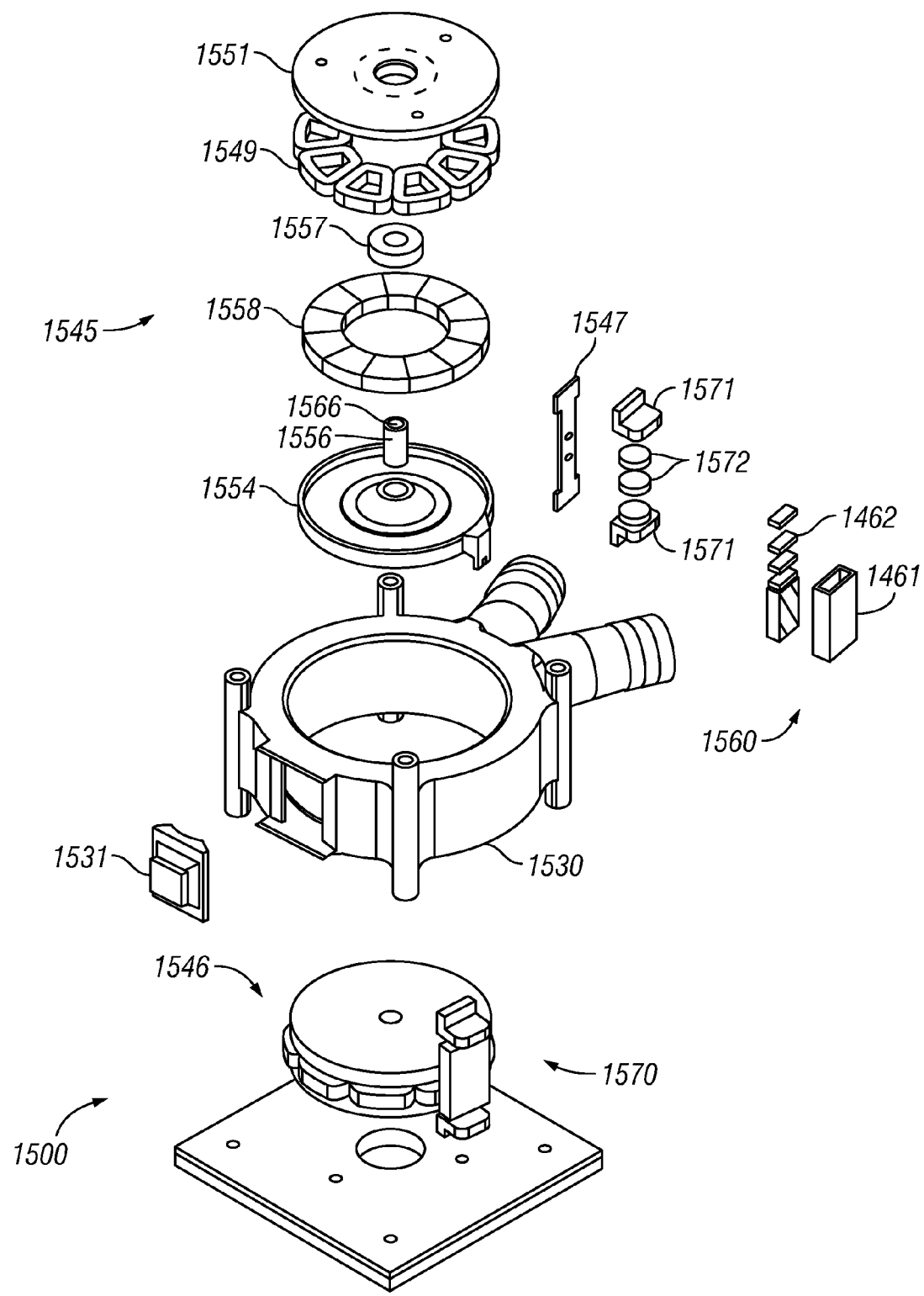
FIG. 43 is an exploded view of an embodiment of the present disclosure.
Figure 44:
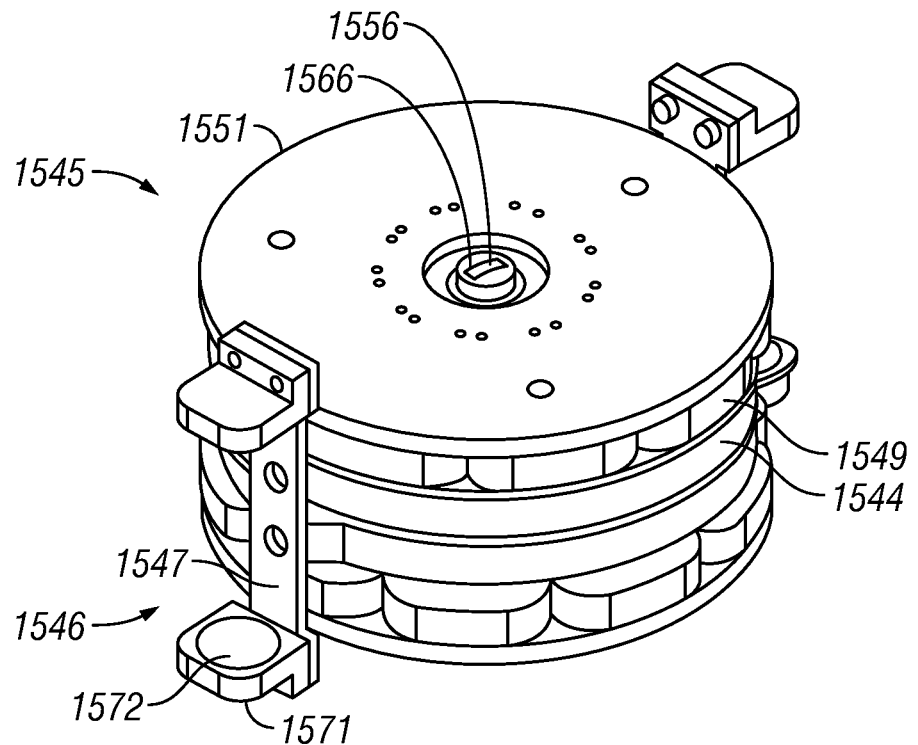
FIG. 44 is an assembled view of a portion of an embodiment of the present disclosure.

Referring now to FIGS. 43-48, another embodiment of a pumping system comprises a pair of motors 1545 and 1546 driving a pump 1500. Motors 1545 and 1546 are generally equivalent in design, and therefore only motor 1545 (shown in exploded view) will be discussed in detail. It is understood that motor 1546 comprises features equivalent to those discussed regarding motor 1545. Pump 1500 comprises a pumping chamber 1530 and a pair of pistons 1560, 1570. Pumping chamber 1530 comprises a removable cap 1531 to allow for pistons 1560, 1570 to be loaded into the pumping chamber. In this embodiment, motor 1545 comprises a rotor 1544 with a linking arm 1547 having extensions 1571 and arm magnets 1572 that are disposed on either side of piston 1560 (which comprises a casing 1561 and piston magnets 1562). Pump 1500 also comprises a plurality of rotor magnets 1548, a set of coils 1549, and a stator plate 1551. Motor 1545 further comprises a shaft 1556 and a bearing 1557. While FIG. 43 represents an exploded view of motor 1545, FIG. 44 represents an assembled view of motor 1546.

Figure 45:
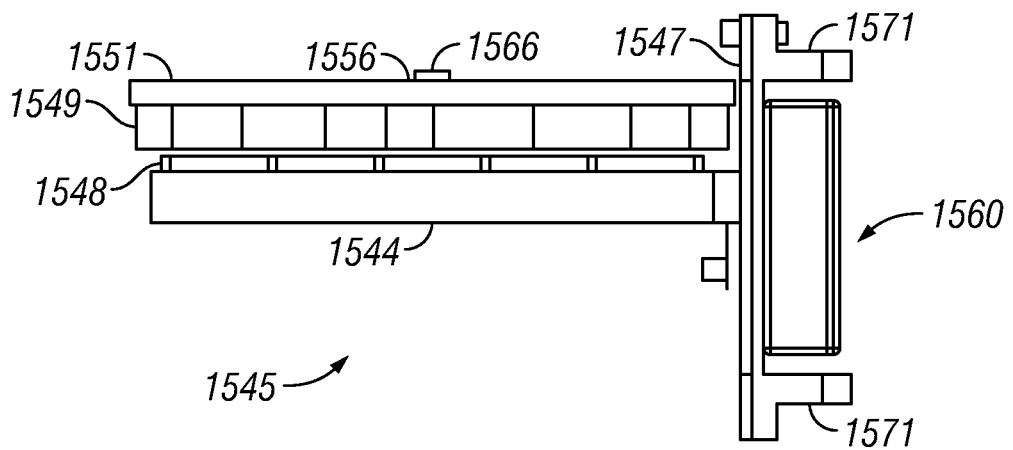
FIG. 45 is a side view of a portion of an embodiment of the present disclosure.
Figure 46:
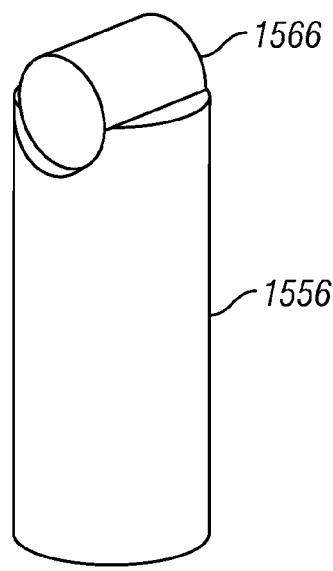
FIG. 46 is a perspective view of a portion of an embodiment of the present disclosure.
Figure 47:
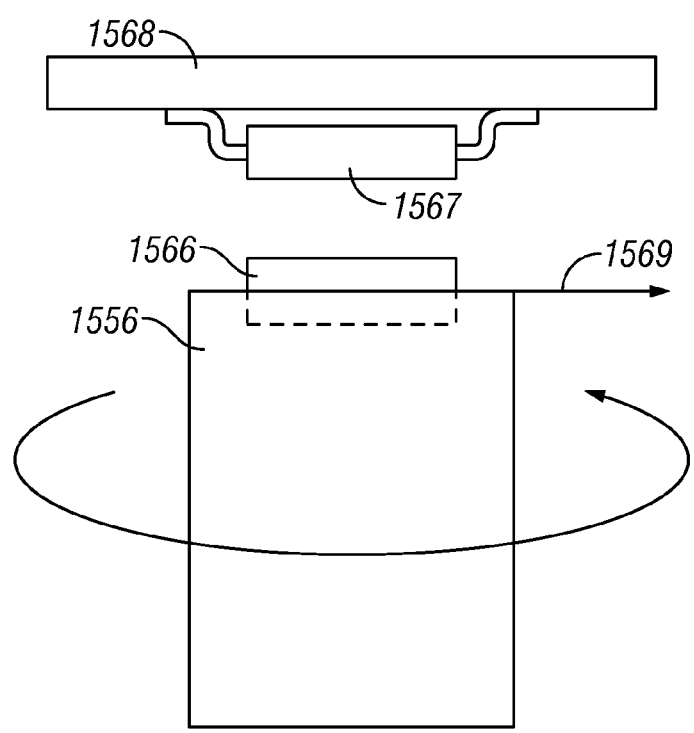
FIG. 47 is a side view of a portion of an embodiment of the present disclosure.

In this embodiment, motor 1545 is an axial flux gap motor which provides for more precise control as compared to other motor configurations. As shown in FIG. 45, there is an axial gap between coils 1549 and rotor magnets 1548. As shown in the detail views in FIGS. 46 and 47, a magnet 1566 can be coupled to the end of shaft 1556 to provide a signal that allows for the rotational position of rotor 1544 to be determined. Specifically, magnet 1566 creates a magnetization vector 1569 that will rotate with the position of the rotor 1544. In the embodiment shown in FIG. 47, a sensor 1567 (such as a 2-axis Hall effect sensor) is coupled to a printed circuit board 1568, which is coupled to a microprocessor (not shown).

Figure 48:
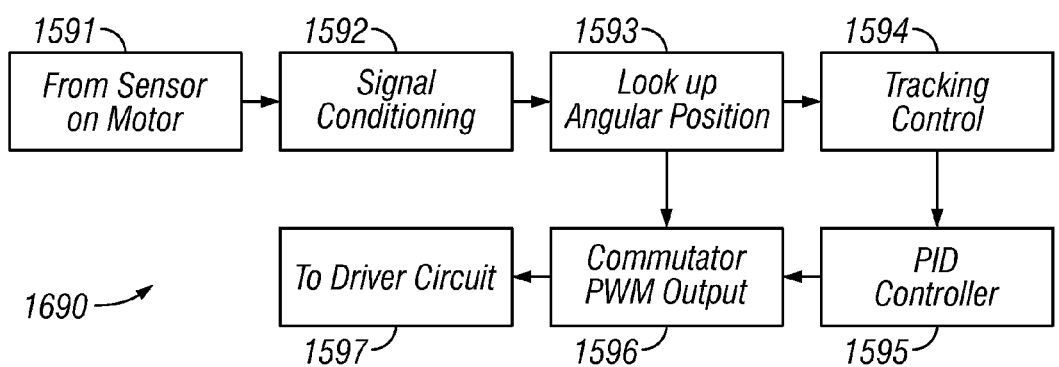
FIG. 48 is a flowchart of a control system used for an embodiment of the present disclosure.

FIG. 48 provides a flowchart illustrating the basic steps in one embodiment of a control system 1590 that can be used to control motor 1545. Other embodiments may use different control systems. In summary, the microprocessor takes information from sensor 1567, conditions it, interprets it to an angular position, compares it with a desired angular position to get an error signal, multiplies this error signal by a gain, translates the control signal to a pulse width modulated signal, and then applies this to the correct phases of motor 1545 via a commutation sequence.

In step 1591, the microprocessor receives two lines of information from each motor 1545, 1546, which are output from sensor 1567 (and the sensor for motor 1546). For purposes of clarity, only the control system for motor 1545 will be discussed in detail. It is understood that the control of motor 1546 operates under the same general principles. This information contains the Cartesian components of the net magnetization vector 1569 that exists over sensor 1567, which is directly produced by magnet 1566. When rotor 1544 and shaft 1556 rotate, so does magnet 1566. As a result, the magnetization vector 1569 rotates proximal to sensor 1567. As magnet 1566 rotates, the magnitude and direction of the x and y components change according to tan(theta)=y/x, where theta is the angular position of the magnetization vector 1569 in the plane parallel to the sensing plane of sensor 1567. Thus, contained in the x and y signal lines lies the information to deduce the angular position of rotor 1544.

The x and y signals enter the microprocessor via data acquisition hardware (not shown) that samples at a frequency (e.g. 250 kHz) sufficient to detect rapid changes in the position of rotor 1544. In certain embodiments, the samples are conditioned in step 1592 via a $4^{th}$ order Butterworth filter to remove high frequency noise. This conditioned x and y data are then passed to the next operation in step 1593.

The Look up Angular Position loop in step 1593 (operating at 1 microsecond per loop iteration in certain embodiments) takes the conditioned x and y data and, using comparison operations, selects one of four lookup tables to determine the theta position of rotor 1544 based on the x and y data. The loop first determines which variable (x or y) is most sensitive at that given point in time by comparing the values of x and y to a predetermine table. After it has been determined which variable is more sensitive, one of four lookup tables, which have been pre-calibrated with the x and y variable data for each ¼ degree angular position of the rotor to determine the rotor's position within ¼ of a degree for that point in time. The angular position is output in bits, each of which correspond to 0.25 degrees in certain embodiments.

Once the theta position of rotor 1544 has been determined, this information passes to two separate operation loops. The Tracking Control loop in step 1594 (executing at a speed controlled by the user, typically 0.1-10 msec per loop iteration) looks at the current angular position of rotor 1544. It then compares this to a desired position for rotor 1544 for that particular point in time and calculates the error by taking the difference. In certain embodiments, the Tracking Control loop in step 1594 has its own clock that starts at zero and steps through consecutive values at the loop rate specified by the user. A look-up table containing the desired position of rotor 1544 as a function of time takes the present clock value and returns the desired rotor position for that time. The desired position is then compared to the actual position of rotor 1544 and an error is computed. As the Tracking Control loop in step 1594 cycles, the clock increments and returns the next desired theta value from the lookup table. In this way, a desired position versus time profile for rotor 1544 to follow can be implemented. The internal clock of this loop is reset by a trigger that is activated when the position of second piston 1570 crosses a certain threshold. The output from this loop is the difference between the rotor position and the desired rotor position. This error signal is then sent to the PID Controller.

The PID Controller in step 1595 takes the error signal and computes a gain by multiplying the error, the integral of the error, and the derivative of the error by a proportional gain variable, integral gain variable, and derivative gain variable respectively. The values of these three variables are specified and tuned by the user. The PID controller in step 1595 then sums these errors and outputs an overall Gain which will be used to tell the rotor of the motor which direction to move and how strongly to move in this direction. This particular PID controller 1595 also uses anti-windup capability which allows for the integral gain to be reset to zero on certain events. This is used to prevent large overshoots of the desired position when rotor 1544 is told to stop at a certain position.

The gain from the PID Controller in step 1595 and the angular position information from the Look-up Angular Position loop in step 1593 are then processed by the Commutator/PWM Output loop in step 1596. In certain embodiments, this loop executes in 25 nanoseconds. This loop performs two operations and outputs the information to control the driver circuit 1597 which ultimately controls the magnitude and direction of the current that is applied to each phase of motor 1545. The Commutator portion of loop 1596 uses the current angular position of rotor 1544 to determine which phases to activate in order to actuate rotor 1544. In certain embodiments, motor 1545 is a brushless DC motor with six pole pairs and nine coils. This yields six symmetric configurations of the rotor and coils. For each of these six repeating sequences there are six commutation steps. This design follows a basic six-step commutation scheme for brushless DC motors. In certain embodiments, this scheme is as follows: 1 0 −1: phase 1 FWD, phase 2 OFF, phase 3 REV.

1 −1 0: phase 1 FWD, phase 2 REV, phase 3 OFF
0 −1 1: phase 1 OFF, phase 2 REV, phase 3 FWD
−1 0 1: phase 1 REV, phase 2 OFF, phase 3 FWD
−1 1 0: phase 1 REV, phase 2 FWD, phase 3 OFF Where FWD refers to applying a forward bias drive voltage to the phase, REV refers to applying a reverse bias drive voltage to the phase, and OFF refers to applying no voltage to the phase.

By stepping through each of these configurations in a certain order, rotor 1544 can be made to rotate by the magnetic fields produced by the phases. Thus in order to achieve a single 360 degree rotation of motor 1545, this six step commutation sequence must be stepped through six times for a total of 36 steps per rotation. Stepping through each of the 36 phase configurations is performed by the Commutator loop in step 1596 by comparing the current angular position of rotor 1544 to an array which tells which of the six steps to use for a particular range in angular position values. For instance, when rotor 1544 is between zero and ten degrees it would use one of the six commutation steps, upon crossing into the 10 to 20 degree range, it would use the next phase activation configuration and so on.

The second part of the Commutation/PWM loop in step 1596 is the translation of the gain signal into a pulse width modulated signal for the driver circuitry. In certain embodiments, each phase is driven by an h-bridge MOSFET that takes a single pulse width modulated input to control both the magnitude and direction of the voltage applied to coils 1549. In certain embodiments, when the input line to the MOSFET is at a 50% duty cycle, the bias voltage across the phase coils is zero. For a PWM duty cycle of 100% (i.e. 5V DC), the coil is forward biased with the full driving voltage (e.g. 12 V). For a PWM duty cycle of 0% (0 V DC), the phase receives the full drive voltage in the reverse bias direction. For a duty cycle of 75%, the phase receives 50% of the drive voltage in the forward biases direction, and so on.

In certain embodiments, the algorithm in the Commutation/PWM loop in step 196 generates this signal in the following way. There is a counter in the loop that increments every tick of the 40 MHz FPGA clock (25 nsec). This counter is programmed to reset every 2000 ticks (50 usec). For each phase, the loop determines how many ticks out of the 2000 tick period that the lines should be turned on. On the rising edge of each 50 usec pulse period the angular position of the motor is used to determine the commutation step to use (1, −1, or 0). The magnitude of the gain from the PID controller is then multiplied by this commutation step to generate the on-time for that particular 50 usec pulse period. The value of 1000 is added to the gain signal in order to account for the fact that an on-time of 1000 ticks is needed to produce zero voltage across a phase (1000/2000=50% duty cycle=0 Volts across phase). Finally, the sign of the gain signal is used to determine which direction to apply the voltage (forward or reverse bias). If the gain is negative, the PWM signal is inverted, thus a 75% on, 25% off PWM signal to the driver circuit which would generate a 50% forward voltage across the phase, would be switched to a 25% on, 75% off PWM signal which would create a 50% reverse voltage to be applied to the phase. This is one advantage of having the zero voltage of the driver existing at a duty cycle of 50%; inversion of the duty cycle reverses the direction but leaves the magnitude the same. For instance, a gain of 500 with a commutation step of 1, −1, 0 would tell phase 1 to turn on for 1500 (500+1000) ticks of the 2000 tick pulse period, resulting in a duty cycle of 75% to the driver circuit which would apply 50% of the drive voltage in the forward position to phase 1, 50% reverse bias for phase 2, and zero volts for phase 3. As the gain varies depending on how close the angular position is to the tracking target angle, the PWM duty cycle varies to apply more or less of voltage to the phases and to move the rotor in a clockwise or counterclockwise direction to minimize said angular error. In this fashion rotor 1544 can be controlled to follow many entered position-time profiles as well as stopping and holding on any particular angle.

By having a tracking controller in which rotor 1546 follows a particular path as it cycles, the position of the piston 1560 can be actuated to generate a variety of hydraulic output profiles. Such profiles may be used in applications requiring pulsatility. The position and velocity of the piston may also be controlled to produce a predetermined waveform in the outlet flow of fluid from the pump.

Figure 49:
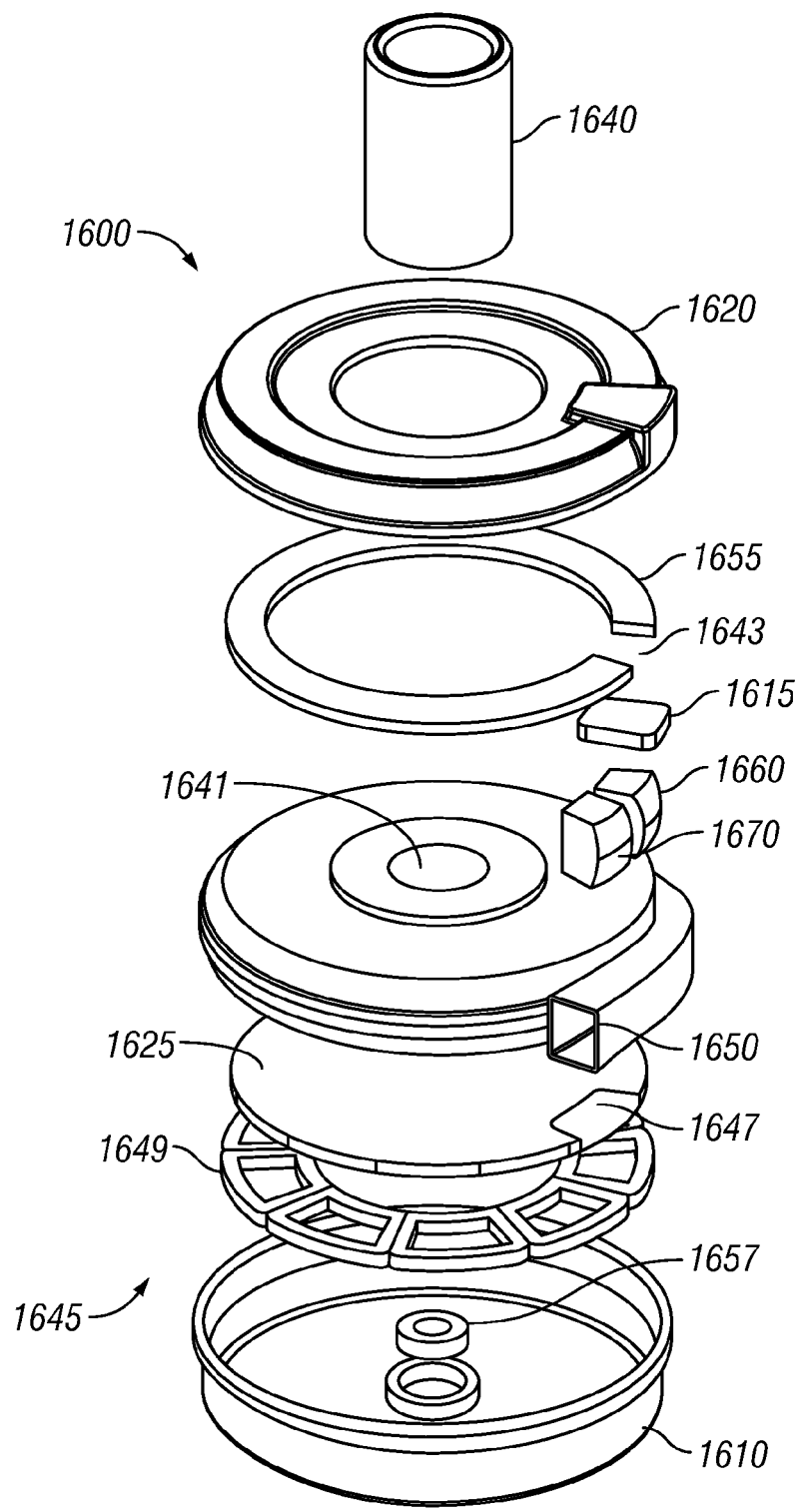
FIG. 49 is an exploded view of an embodiment of the present disclosure.
Figure 50:
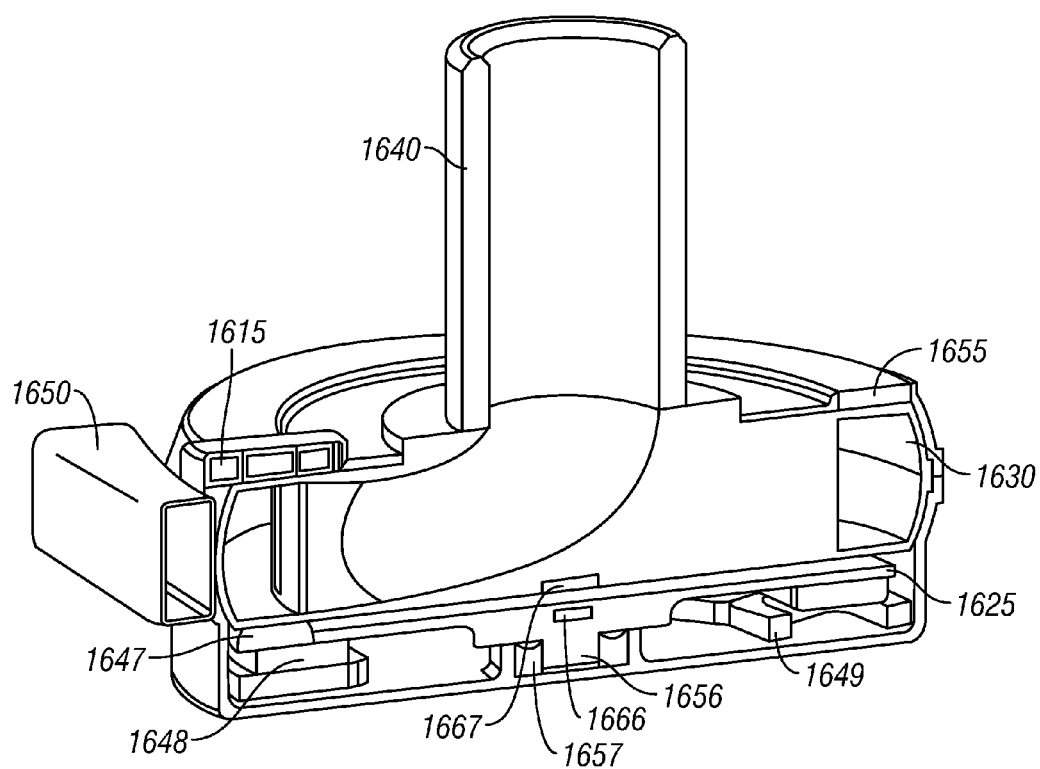
FIG. 50 is a section view of the embodiment of FIG. 49.
Figure 51:
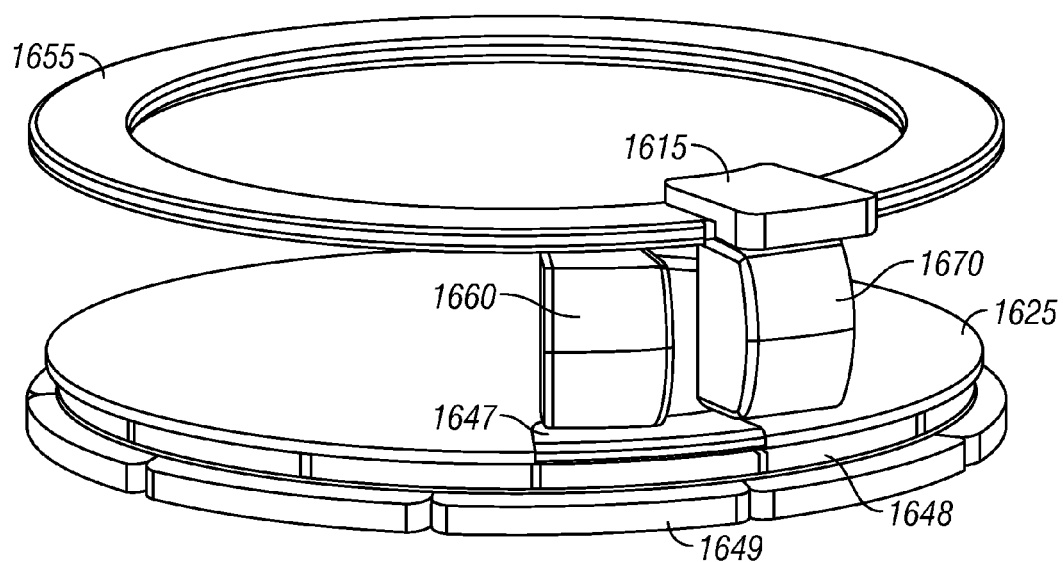
FIG. 51 is a perspective view of a portion of an embodiment of the present disclosure.

Referring now to FIGS. 49-51, another embodiment of a pump 1600 comprises a lower casing 1610, an upper casing 1620, a pumping chamber 1630, an inlet conduit 1640, and inlet port 1641 and an outlet 1650. Pump 1600 further comprises a pair of pistons 1660, 1670 driven by a motor 1645, which comprises a rotor 1625, a bearing 1657, a set of coils 1649, and magnets 1648. Pump 1600 also comprises a magnetic ring 1655 and an electromagnet 1615. It is understood that magnetic ring 1655 may not form a complete circle; for example, magnetic ring 1655 may comprise a gap 1653 in which electromagnet 1615 is positioned. Similar to previously-described embodiments, shaft 1656 may contain a magnet 1666 that is detected by a sensor 1667 to determine the rotational position of rotor 1625.

Figure 52:
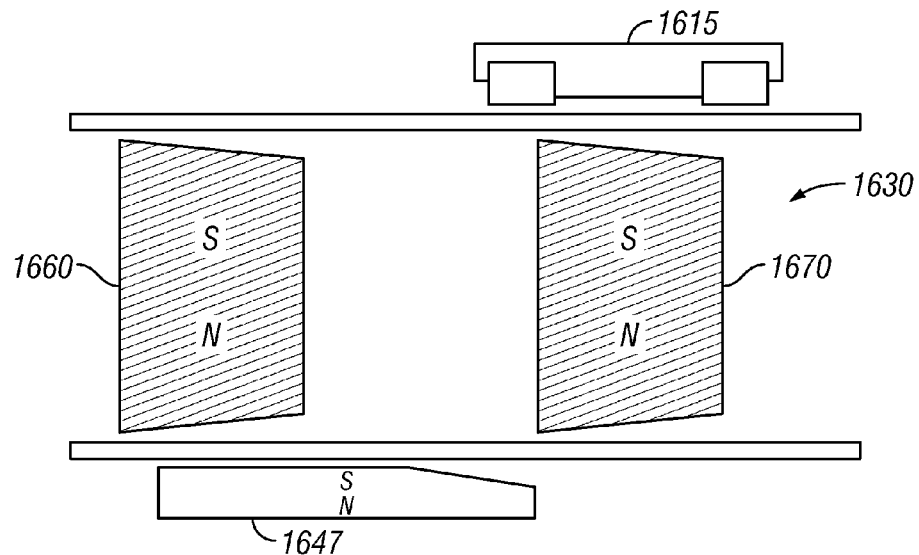
FIGS. 52-56 are section views of a portion of an embodiment of the present disclosure.
Figure 53:
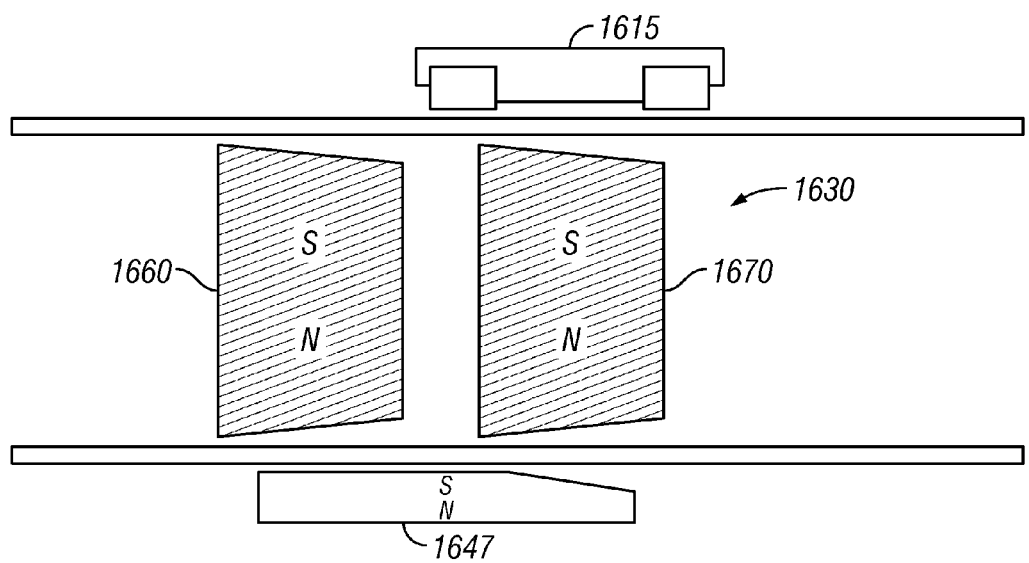
Figure 54:
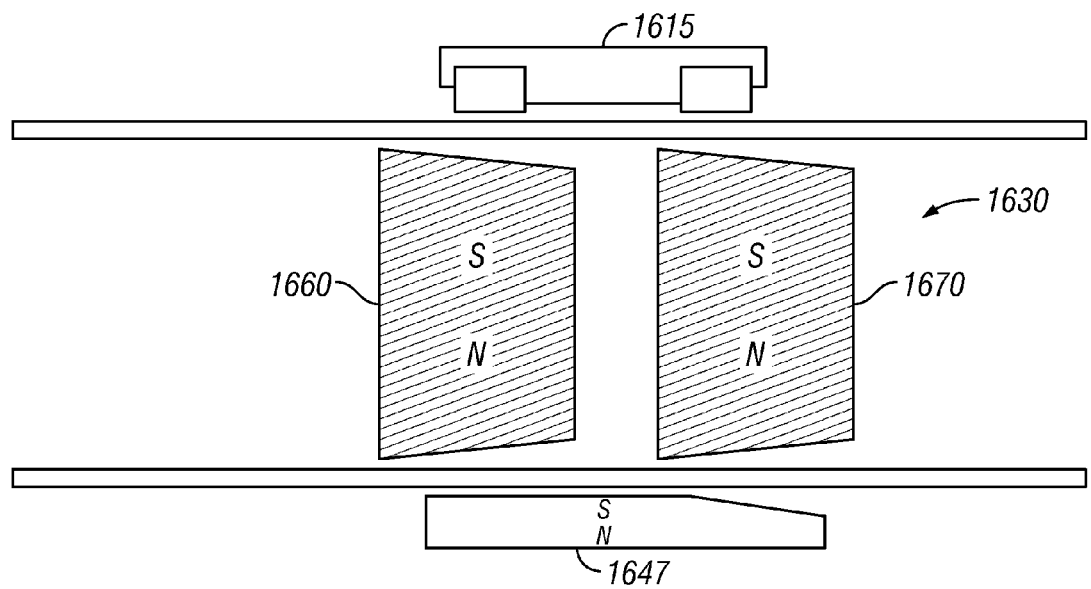
Figure 55:
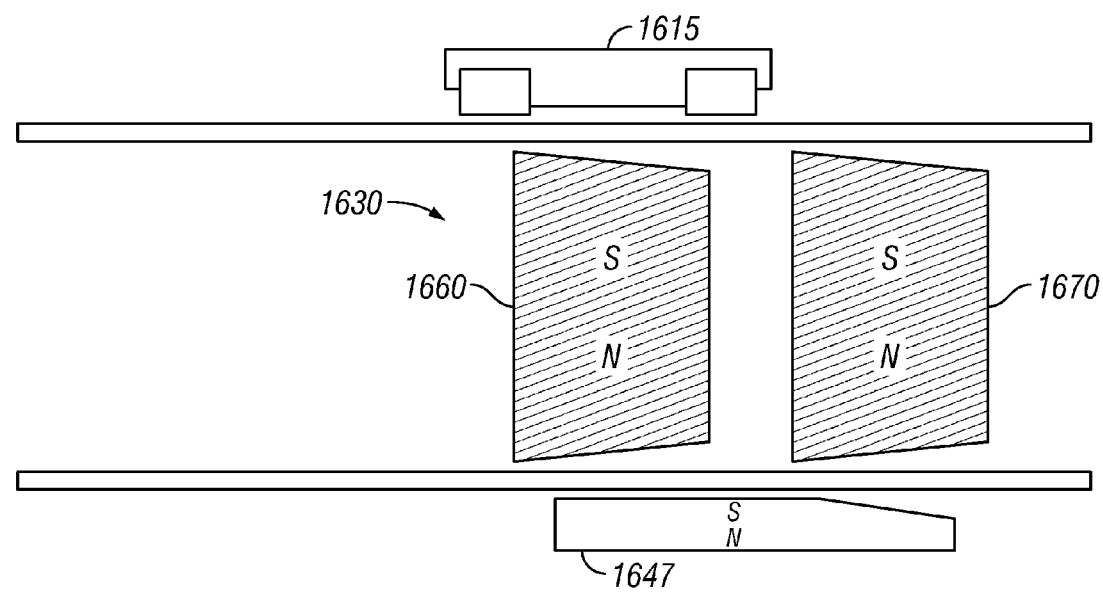
Figure 56:
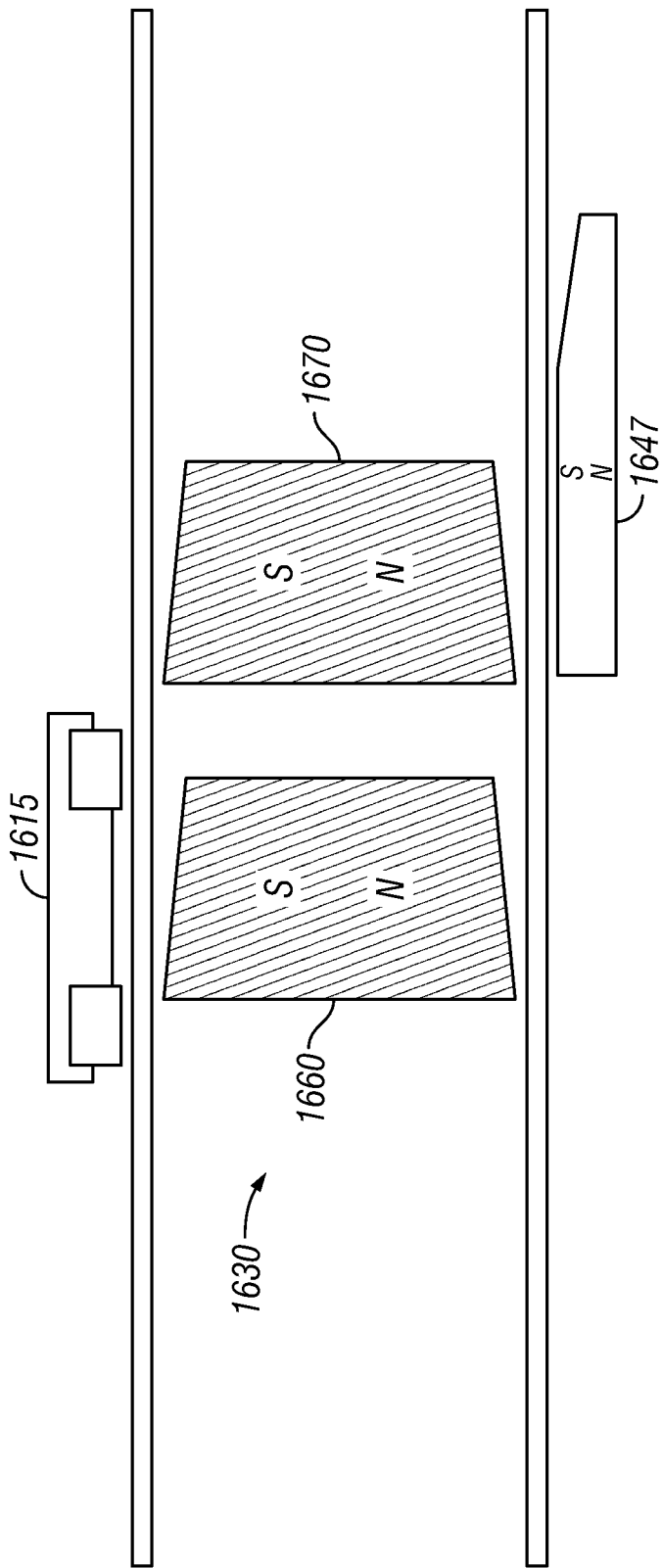

Unlike previous embodiments which require a separate motor to move each piston around the pumping chamber, pump 1600 moves both pistons 1660, 1670 with a single motor 1645. In certain embodiments, a magnetic link 1647 is coupled to a rotor 1644. Magnetic link 1647 is first coupled to piston 1660, while piston 1670 is held in place by an electromagnet 1615. FIGS. 52-56 illustrate one embodiment of how magnetic link 1647 transitions from being initially coupled to piston 1660 and being subsequently coupled to piston 1670 (while both piston 1660 and piston 1670 are located in pumping chamber 1630). The labels "N" and "S" refer to the north and south poles of the magnets, respectively. It is also understood that while pistons 1660 and 1670 are shown with tapered surfaces that can act as hydrodynamic bearing surfaces, other embodiments may not include hydrodynamic bearing surfaces. Referring initially to FIGS. 52 and 53, magnetic link 1647 is linked to piston 1660 and piston 1670 is held stationary by electromagnet 1615. As rotor 1625 rotates, piston 1660 is directed around pumping chamber 1630. With piston 1670 held in place, the movement of piston 1660 forces fluid from pumping chamber 1630 to exit through outlet 1650 (shown in FIGS. 49 and 50). As shown in FIG. 54, when piston 1660 approaches piston 1670, electromagnet 1615 is momentarily turned off so that piston 1670 is no longer held in place by electromagnet 1615. Piston 1670 is then displaced by piston 1660 (or fluid pressure between pistons 1660 and 1670). In certain embodiments, the current applied to electromagnet 1615 can be reversed to apply a repulsive force to piston 1670. As shown in FIG. 55, magnetic link 1647 then moves piston 1660 into the location previously occupied by piston 1670. At this point, electromagnet 1615 is re-energized so that it holds piston 1660 in place. Referring now to FIG. 56, magnetic link 1647 then directs piston 1670 around pumping chamber 1630 while piston 1660 is held stationary. While piston 1670 travels around pumping chamber 1630, it forces fluid to exit through outlet 1650. As piston 1670 approaches piston 1660, electromagnetic 1615 is again de-energized so that piston 1660 is no longer held in place. Piston 1670 (or fluid pressure between fluid 1660 and 1670) displaces piston 1660 from its location. Rotor 1625 and magnetic link 1647 then move piston 1670 into the location previously occupied by piston 1670. Electromagnet 1615 is re-energized so that it holds piston 1670 in place. Rotor 1625 and magnetic link 1647 then direct piston 1660 around pumping chamber 1630 and the cycle is repeated. In this manner, the movement of both pistons 1660 and 1670 is controlled by a single motor 1645.

Figure 57:
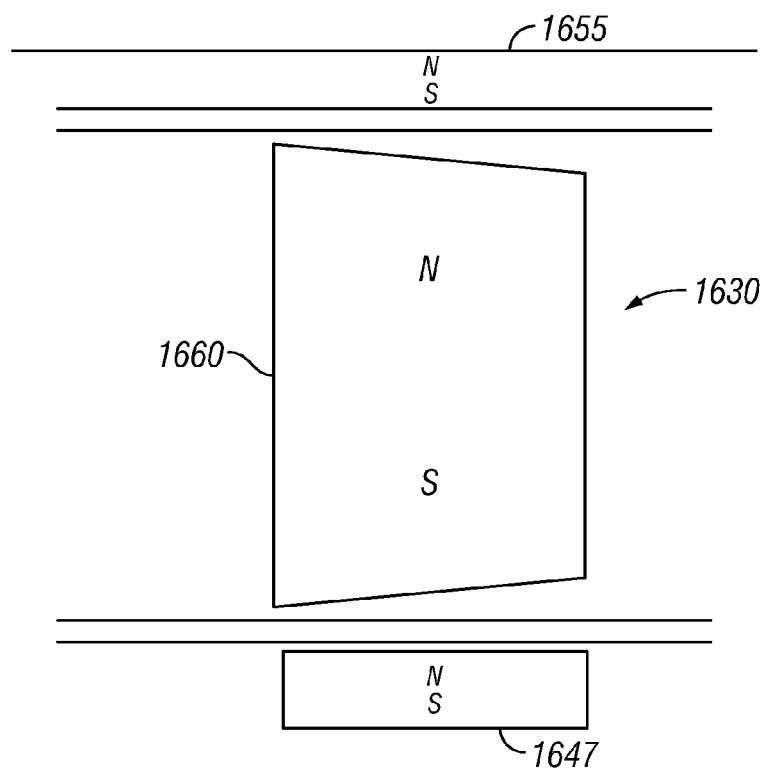
FIGS. 57-62 are section views of a portion of an embodiment of the present disclosure.
Figure 58:
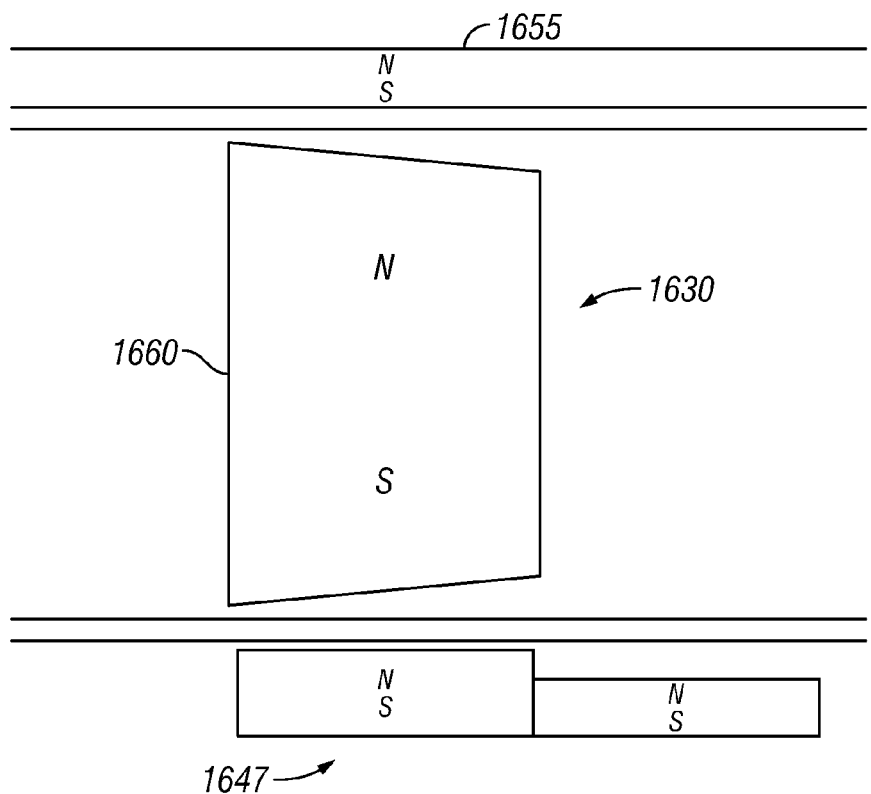
Figure 59:
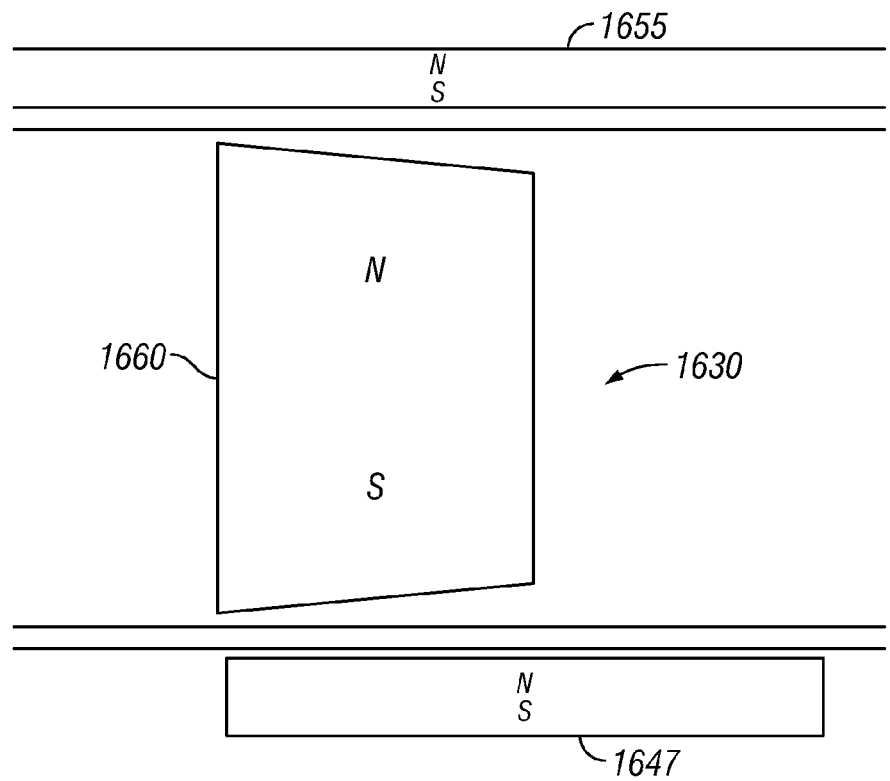
Figure 60:
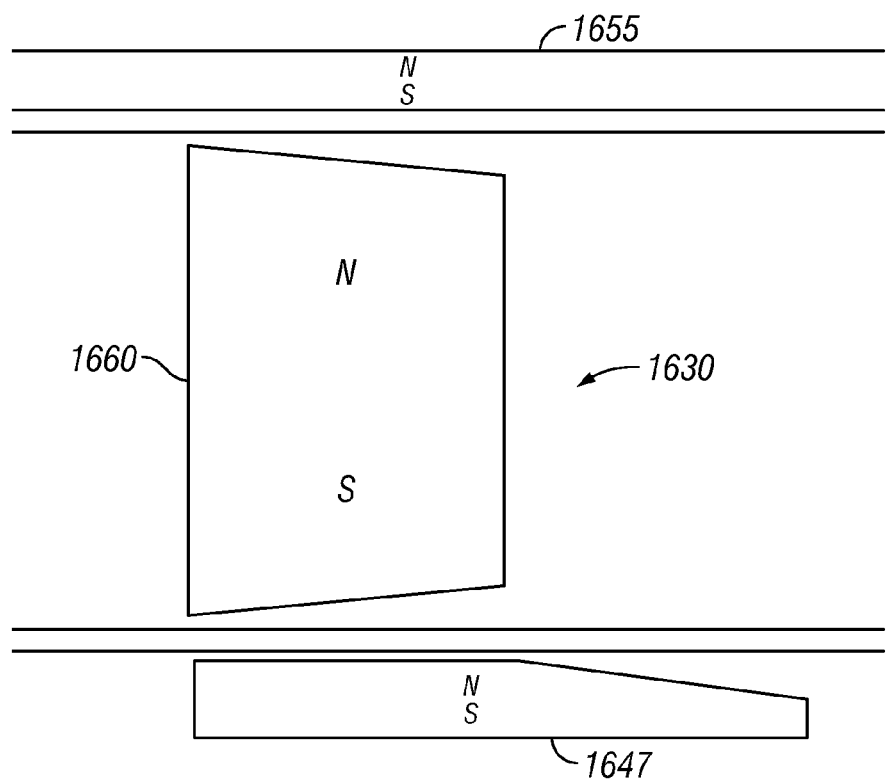
Figure 61:
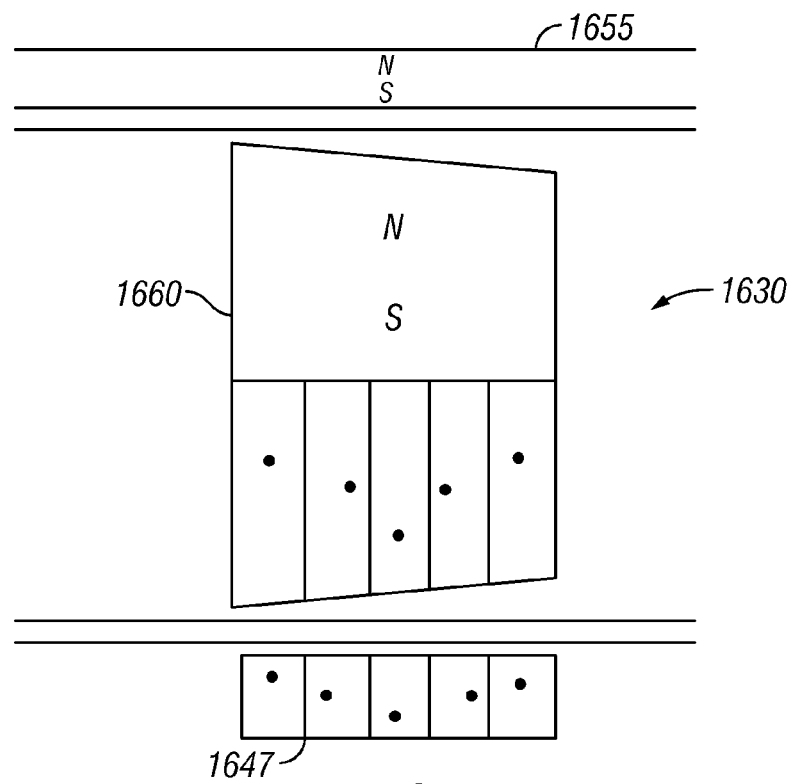
Figure 62:
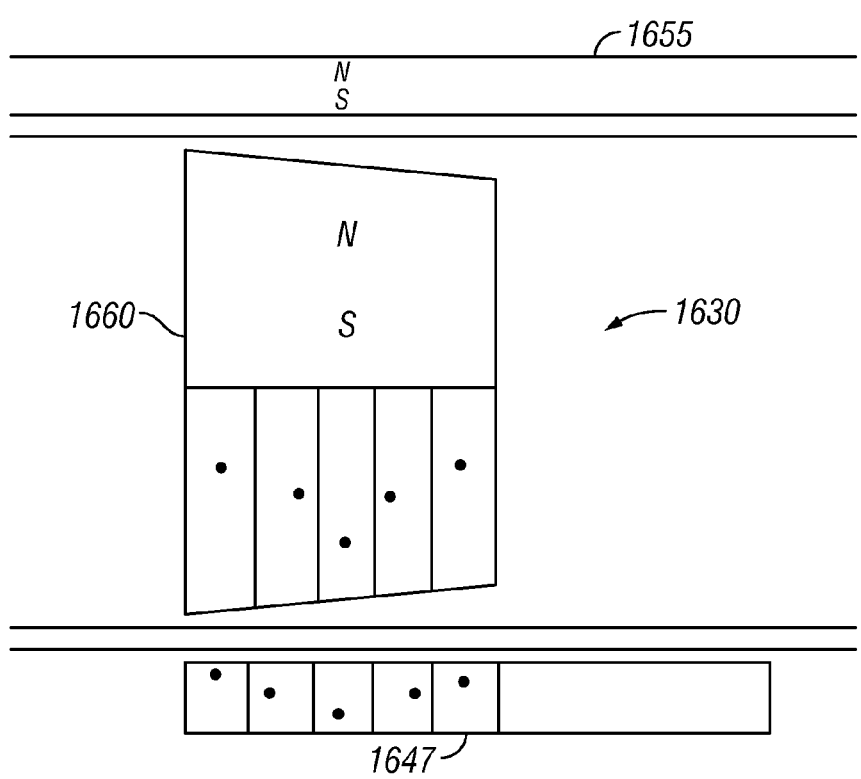

Referring now to FIGS. 57-62, various embodiments of magnetic link 1647, piston 1660, and magnetic ring 1655 are shown. In FIG. 57, magnetic link 1647 and piston 1660 are permanent magnets that are generally the same width. In FIG. 58, magnetic link 1647 is comprised of two permanent magnets, with a stronger permanent magnet located under piston 1660 and a smaller magnet extending beyond the leading face 1623 of piston 1660. As shown in FIG. 59, magnetic link 1647 comprises a permanent magnet with a constant thickness that extends beyond the leading face 1623 of piston 1660. Referring now to FIG. 60, magnetic link 1647 comprises a permanent magnet that extends beyond the leading face 1623 of piston 1660 and tapers to a thinner cross-section. In the embodiment of FIG. 61, piston 1660 and magnetic link 1647 also each comprise a Halbach array. In the embodiment shown in FIG. 62, piston 1660 and magnetic link 1647 each comprise a Halbach array. In addition, magnetic link 1647 further comprises an extension of magnetically permeable material 1646. The inclusion of an extension of magnetic link 1647 past the leading face 1623 of piston 1660 may provide for a smoother transition from piston 1660 to piston 1670.

Because magnetic link 1647 acts on only one side of pistons 1660, 1670 the forces on piston 1600 may not be balanced. Pistons 1660 and 1670 can therefore experience increased drag or friction forces against the portion of pumping chamber 1630 that is proximal to magnetic link 1647. To counteract this force, certain embodiments of pump 1600 comprise magnetic ring 1655 positioned so that pistons 1660, 1670 are located between magnetic link 1647 and magnetic ring 1655. As shown in the detail view of FIG. 51, magnetic ring 1655 can be positioned so that it is generally parallel with rotor 1625. Therefore, magnetic ring 1655 can offset the magnetic forces exerted on pistons 1660, 1670 by magnetic link 1647 and reduce the drag or friction forces created when pistons 1660, 1670 move within pumping chamber 1630. In other embodiments, other features may be used to offset the magnetic forces acting on pistons 1660, 1670, and a magnetic ring may not be used. For example, pistons 1660, 1670 may incorporate a hydrodynamic bearing surface that creates a force opposing the magnetic force provided by magnetic link 1647. Additionally, magnetic ring 1655 can be used in combination with hydrodynamic bearing surfaces to enable passive levitation of the piston as it moves within the chamber.

Figure 63:
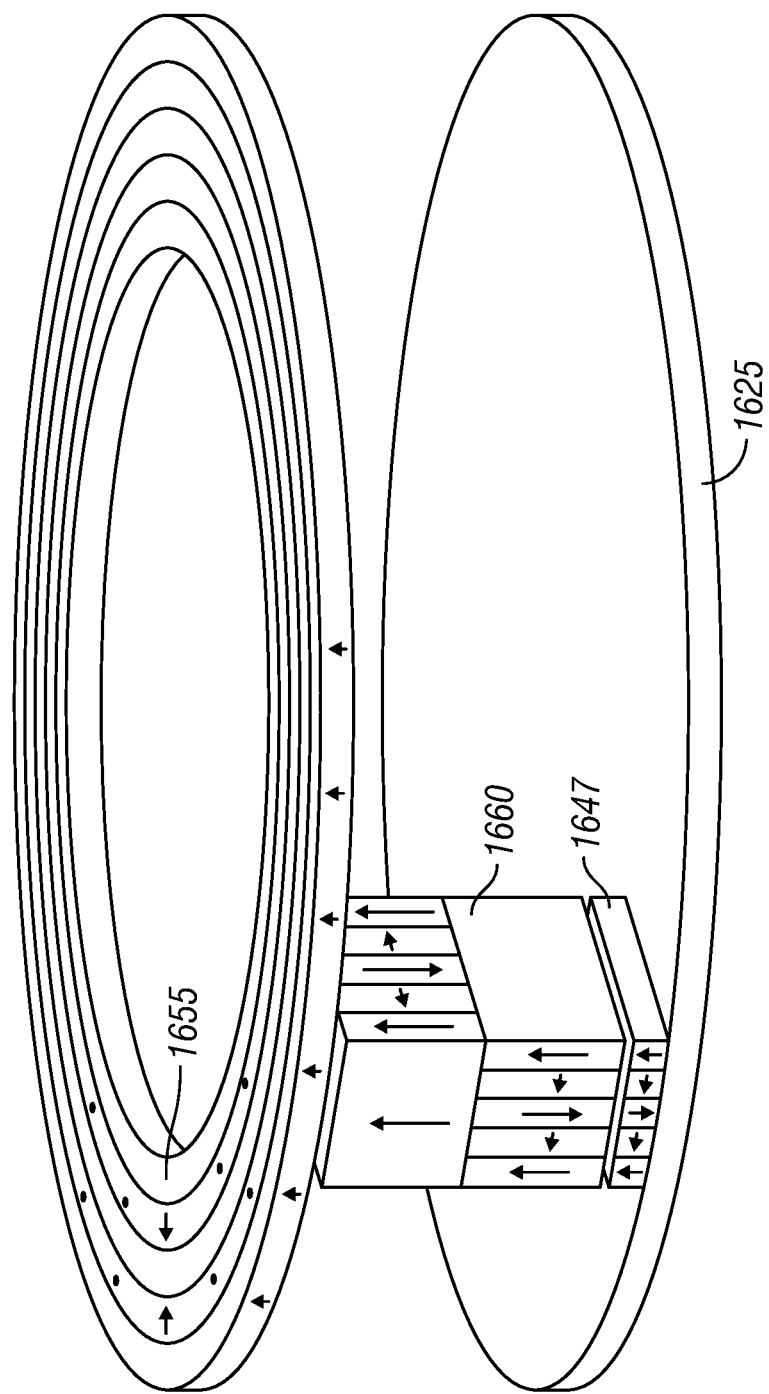
FIG. 63 is a perspective view of a portion of an embodiment of the present disclosure.

Referring now to FIG. 63, a detailed view of one embodiment of magnetic ring 1655, piston 1660, magnetic link 1647 and rotor 1625 illustrates how Halbach arrays may be incorporated to reduce the required magnet size and/or increase the magnetic forces created. As understood by those skilled in the art, a Halbach array is an arrangement of magnets which increase the magnetic field on one side of the array, and reduces the magnetic field on the opposing side. Additionally, the Halbach array can be used to prohibit excessive drifting of piston 1660 relative magnetic link 1647 when forces arise to displace piston 1660 from magnetic link 1647. In the embodiment shown in FIG. 63, magnetic ring 1655 comprises a Halbach array configured to increase the magnetic field on the side closest to piston 1660. In addition, piston 1660 comprises two Halbach arrays (which may be joined with epoxy or any other suitable means) configured to increase the magnetic field on the side closest to magnetic ring 1655. In addition, magnetic link 1647 comprises a Halbach array configured to increase the magnetic field on the side closest to piston 1660. It is understood that FIG. 63 is just one exemplary embodiment, and that other embodiments may not comprise Halbach arrays in magnetic ring 1655, piston 1660, or magnetic link 1647.

Figure 64:
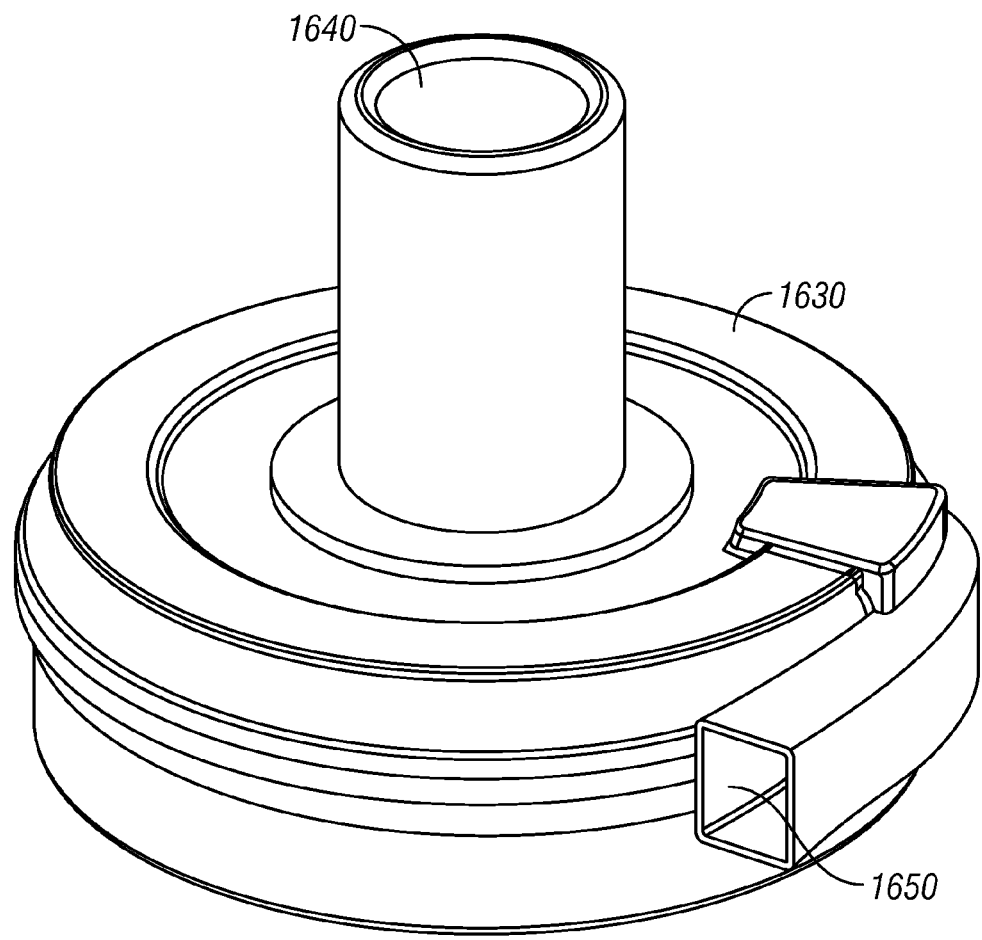
FIG. 64 is a perspective view of an embodiment of the present disclosure.
Figure 65:
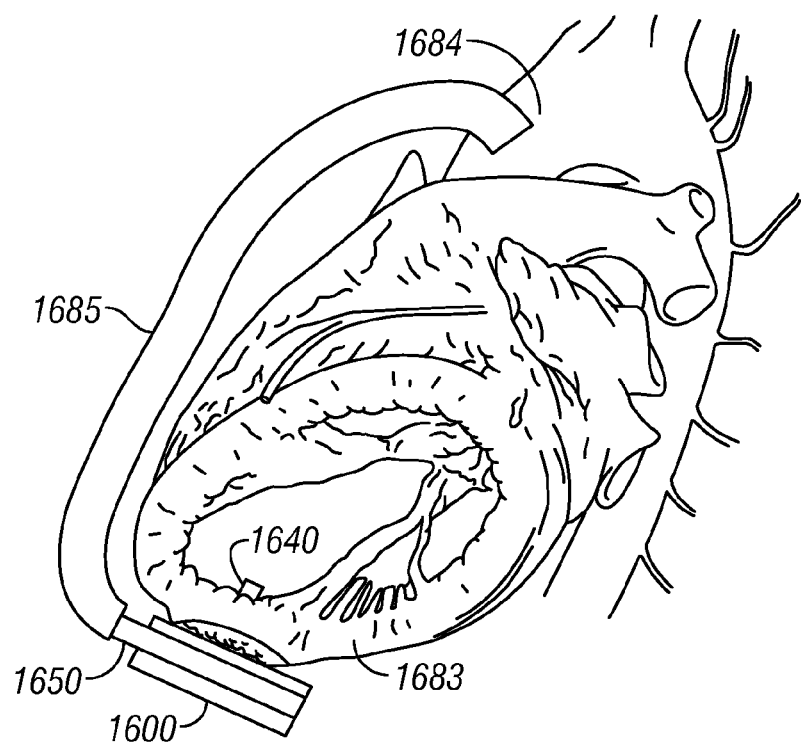
FIGS. 65-66 are views of an embodiment of the present disclosure inserted in a patient.
Figure 66:
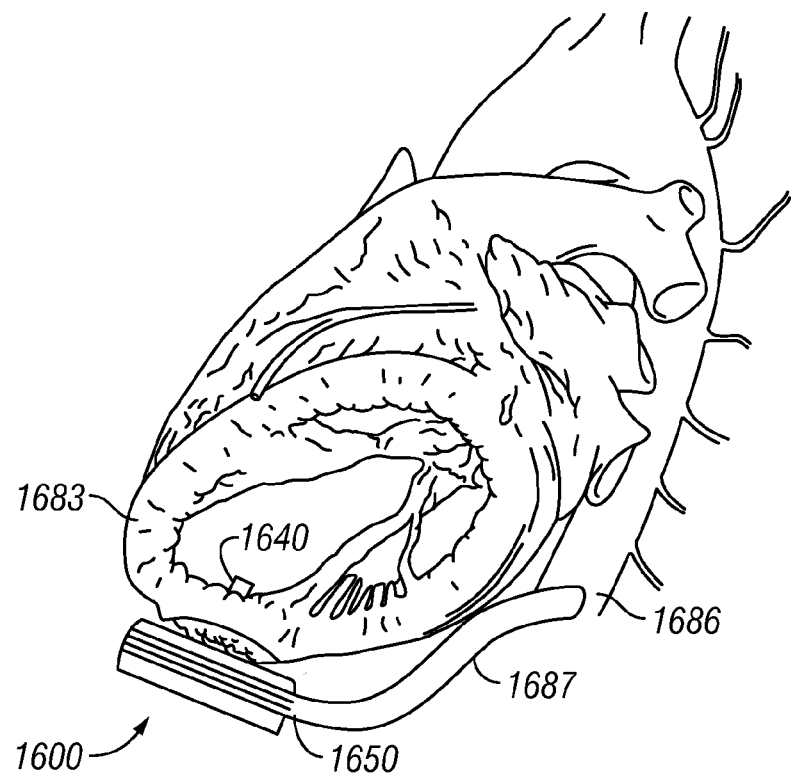

Referring back now to FIG. 50, inlet conduit 1640 is shown to extend from the central portion of pumping chamber 1630 rather than the perimeter. As shown in the perspective view of FIG. 64, inlet conduit 1640 also extends generally perpendicular to pumping chamber 1630 and outlet 1650. Referring now to FIGS. 65 and 66, such a configuration allows pump 1600 to be placed in the human body so that inlet conduit 1640 extends into a patient's left ventricle 1683. Outlet 1650 may be coupled to ascending aorta 1684 via conduit 1685 as shown in FIG. 65. Outlet 1650 may also be coupled to descending aorta 1686 via conduit 1687, as shown in FIG. 66. In certain embodiments, outlet 1650 is anastomosed to ascending aorta 1684 or descending aorta 1686.

Figure 67:
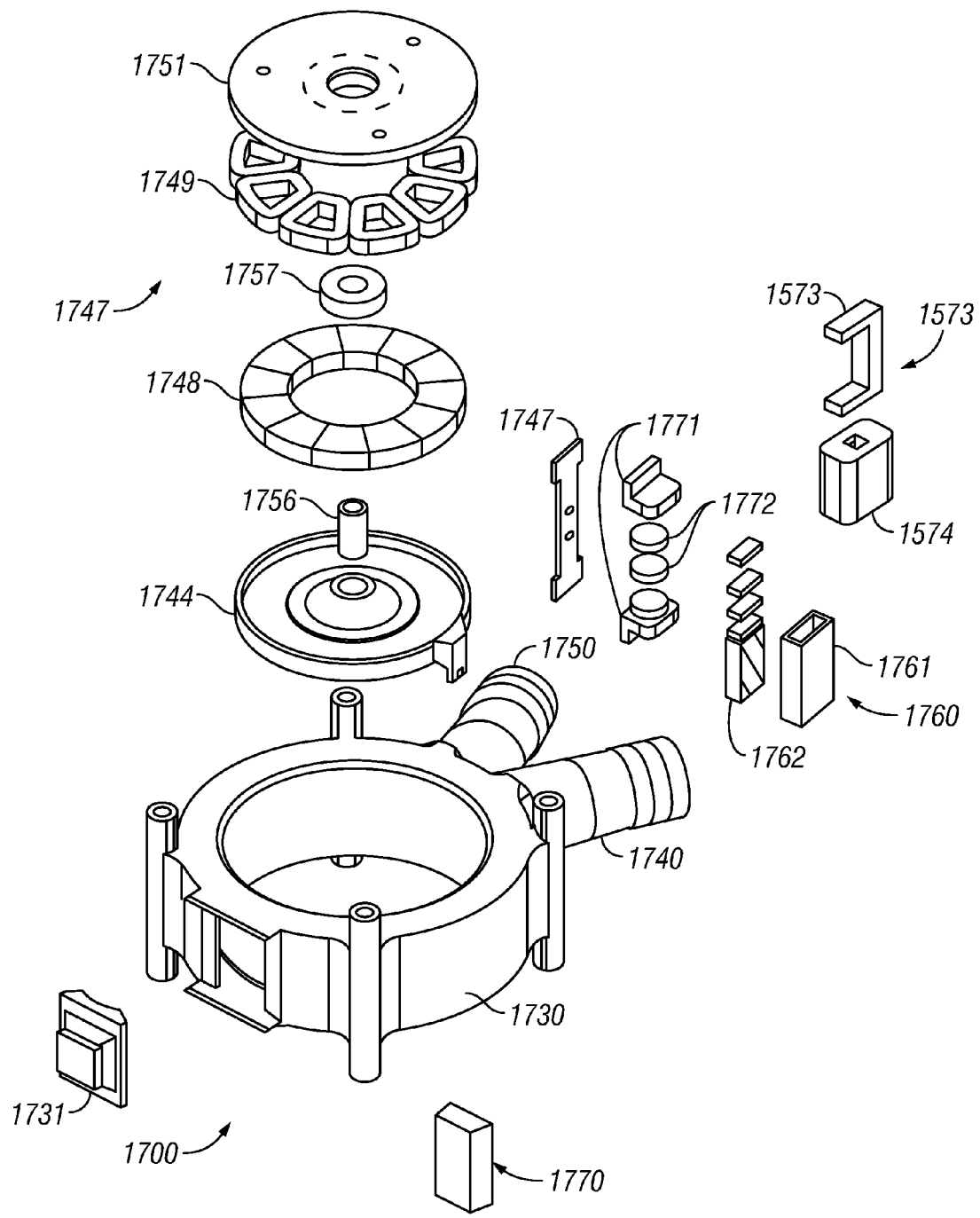
FIG. 67 is an exploded view of an embodiment of the present disclosure.
Figure 68:
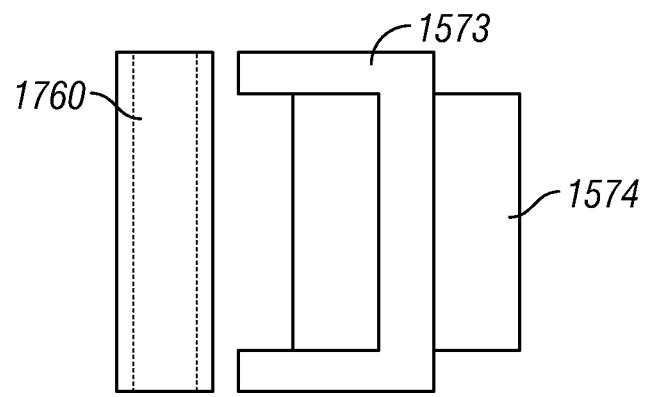
FIG. 68 is a side view of a portion of an embodiment of the present disclosure.
Figure 69:
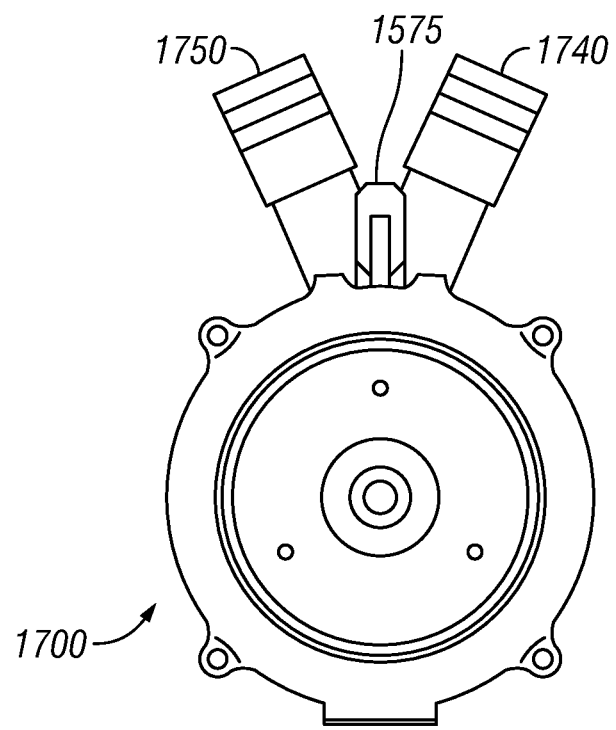
FIG. 69 is a top view of the embodiment of FIG. 67.

Referring now to FIGS. 67-69, another embodiment of a pump 1700 utilizes a single motor 1745 to drive a pair of pistons 1760, 1770. However, the basic configuration of this pump more closely resembles that of pump 1500 shown in FIG. 43, rather than pump 1600 shown in FIG. 49. More specifically, inlet 1740 and outlet 1750 do not extend perpendicular to each other and lie in the same plane as pumping chamber 1730. Components in FIG. 67 that are equivalent to components in FIG. 43 are labeled with like numbers, with the exception that FIG. 67 components begin with "17xx" and components in FIG. 43 begin with "15xx". In the interest of brevity, a full description of the components will not be repeated here.

Pump 1700 differs from pump 1500 in that pump 1700 comprises a single motor 1745 to control both pistons 1760 and 1770. In addition, pump 1700 comprises an electromagnet 1575 comprising a permeable core 1573 and a coil 1574. Pump 1700 operates with the same general principles as those described in the discussion of pump 1600. However, pump 1700 may not require a magnetic ring similar to magnetic ring 1655 because arm magnets 1772 are disposed above and below pistons 1760 and 1770. Therefore, the magnetic forces acting on pistons 1760 and 1770 can be balanced without the use of a separate magnetic ring.

It should be appreciated that the exemplary embodiments previously described can be operated in a forward direction where fluid is drawn into the pump through the inlet conduit and ejected through the outlet conduit or in a reverse direction where the fluid enters the outlet and exits through the inlet conduit. Reverse operation in achieved by simply actuating the pistons in the reverse direction.

While the above description contains many specifics, these should not be construed as limitations on the scope of the invention, but as exemplifications of the presently preferred embodiments thereof. Many other modifications and variations are possible within the teachings of the invention such as using the pump to oscillate fluid through a flow circuit or using the pump for the precise delivery of discrete and metered fluid quantities to a system. Other embodiments may comprise additional features, such as one or more sensors configured to measure properties of the pumped fluid (e.g., temperature, pH, pressure, etc.)

Thus the scope of the invention should be determined by the appended claims and their legal equivalents, and not by the examples given.

REFERENCES

The following references, to the extent that they provide exemplary procedural or other details supplementary to those set forth herein, are specifically incorporated herein by reference.

U.S. Pat. No. 6,576,010
U.S. Pat. No. 5,089,016

What is claimed is:

1. A system, comprising:
a pumping chamber forming a closed loop;
a pump inlet in fluid communication with the pumping chamber;
a pump outlet in fluid communication with the pumping chamber;
a first piston movable within the pumping chamber, wherein the first piston comprises a first piston Halbach array;
a second piston movable within the pumping chamber and structurally independent of the first piston, wherein the second piston comprises a second piston Halbach array;
the first piston and second piston each comprising a leading face, a trailing face, and one or more perimeter faces each between the leading face and the trailing face, each of the one or more perimeter faces being closely adjacent one or more similarly configured chamber inner surfaces as each piston moves within the pumping chamber, each of the one or more perimeter faces further comprising a hydrodynamic bearing surface, each hydrodynamic bearing surface spaced between the leading face and the trailing face, each hydrodynamic bearing surface adjacent the leading face spaced from a respective chamber surface by a spacing greater than a spacing between the hydrodynamic bearing surface adjacent the trailing face and the chamber surface;
an electric motor having a rotor with a magnetic link; and
an electromagnet electrically energizable from a dormant state to one or more energized states;
wherein the system is configured such that during system operation:
the electromagnet is initially energized to magnetically couple to the first piston to hold the first piston stationary within the chamber;
the rotor of the electric motor is initially magnetically coupled to the second piston and the electric motor is operated to move the second piston within the chamber relative to the first piston using the rotor and to thereby increase a volume of a portion of the chamber between a leading face of the first piston and a trailing face of the second piston while the portion of the chamber between the leading face of the first piston and the trailing face of the second piston is in fluid communication with the pump inlet while simultaneously decreasing a volume of a portion of the chamber between the trailing face of the first piston and the leading face of the second piston while the portion of the chamber between the trailing face of the first piston and the leading face of the second piston is in fluid communication with the pump outlet;
wherein the system is configured such that during system operation:
the electromagnet is subsequently one of de-energized to magnetically release the first piston and energized to repel the first piston away from the electromagnet, and the electromagnet is then re-energized to magnetically couple to the second piston to hold the second piston stationary within the chamber; and
the rotor of the electric motor is subsequently magnetically released from the second piston and then magnetically coupled to the first piston to move the first piston within the chamber relative to the second piston and to thereby increase a volume of a portion of the chamber between the leading face of the second piston and the trailing face of the first piston while simultaneously decreasing a volume of a portion of the chamber between the trailing face of the second piston and the leading face of the first piston;
wherein de-energizing the electromagnet means restoring the electromagnet to a dormant state by substantially depriving the electromagnet of current flow; and
wherein energizing the electromagnet to repel the first piston means energizing the electromagnet using a current flow that reverses the polarity of the electromagnet as compared to the current flow used to energize the electromagnet to magnetically couple to the first piston.

2. The system of claim 1, further comprising:
a magnetic ring comprising a Halbach array, wherein the magnetic ring is proximal to the pumping chamber; and
wherein the chamber in which the first piston and the second piston are movable is disposed between the magnetic ring and the rotor with the magnetic link.

3. The system of claim 1, wherein the system is configured such that during system operation, the electromagnet is energized to be one of magnetically coupled to and magnetically repelled by one of the first piston and the second piston when the electromagnet is energized, and the electromagnet is decoupled from the first piston and from the second piston when the electromagnet is de-energized.

4. The system of claim 1, wherein the magnetic link comprises a Halbach array.

5. The system of claim 1, wherein the system is configured such that, during system operation, a portion of the magnetic link extends beyond the leading face of the first piston while the first piston is magnetically coupled to the rotor and the portion of the magnetic link extends beyond the leading face of the second piston while the second piston is magnetically coupled to the rotor.

6. The system of claim 1, wherein the first piston and the second piston each comprise a second Halbach array.

7. The system of claim 1, wherein the system is configured such that, during operation, the pump inlet is insertable into a ventricle of a heart, and the pump outlet is adapted for being placed in fluid communication with an ascending aorta, a descending aorta, or a pulmonary artery.

8. The system of claim 1, further comprising:
a power supply;
a driver circuit electrically coupled to the electric motor and to the power supply;
a microprocessor electrically coupled to the driver circuit; and
a sensor to sense a position of the first piston within the pumping chamber, wherein:
the driver circuit is configured to selectively couple the power supply to the electric motor upon receiving a control signal;
the sensor is electrically connected to the microprocessor;
the microprocessor is configured to interpret the position from the sensor; and
the microprocessor is configured to output the control signal to the driver circuit.

9. The system of claim 8, wherein a position and an angular velocity of the electric motor is controlled by the microprocessor to produce a predetermined waveform in an outlet flow from the pump outlet.

10. A system comprising:
a pumping chamber forming a closed loop;
a pump inlet in fluid communication with the pumping chamber;
a pump outlet in fluid communication with the pumping chamber;
a first piston disposed within the pumping chamber and comprising a leading face, a trailing face, and one or more perimeter faces between the leading face and the trailing face, each of the one or more perimeter faces being closely adjacent one or more similarly configured chamber surfaces as the first piston moves within the pumping chamber, each of the one or more perimeter faces further comprising a hydrodynamic bearing surface, each hydrodynamic bearing surface spaced between the leading face and the trailing face, each hydrodynamic bearing surface spaced adjacent the leading face from a respective chamber surface by a spacing greater than a spacing between the hydrodynamic housing surface adjacent the trailing face and the chamber surface;
a second piston disposed within the pumping chamber and comprising a leading face, a trailing face, and one or more perimeter faces between the leading face and the trailing face, each of the one or more perimeter surfaces being closely adjacent one or more similarly configured chamber surfaces as the second piston moves within the pumping chamber, each of the one or more perimeter surfaces further comprising the hydrodynamic bearing surface, each hydrodynamic bearing surface spaced between the leading face and the trailing face, each hydrodynamic bearing surface spaced adjacent the leading face from a respective chamber surface by a spacing greater than a spacing between the hydrodynamic housing surface adjacent the trailing face and the chamber surface;
an electric motor having a rotor with a magnetic link; and
an electromagnet energizable from a dormant state to one or more energized states;
wherein the system is configured such that, during system operation:
the electromagnet is initially energized to magnetically couple to the first piston to hold the first piston stationary in the chamber;
the rotor of the electric motor is initially magnetically coupled to the second piston to enable movement of the second piston independently of the first piston by operation of the electric motor;
the electromagnet is subsequently one of de-energized to magnetically release the first piston and energized to repel the first piston away from the electromagnet, and then reenergized to magnetically couple to the second piston; and
the rotor of the electric motor is subsequently magnetically released from the second piston and then magnetically coupled to the first piston; and
wherein the system is configured such that:
the electric motor comprises a rotor coupled to a linking arm;
the linking arm is magnetically coupled to a first magnet, wherein the first magnet is located on one face of the first piston during operation;
the linking arm is coupled to a second magnet, wherein the second magnet is located on an opposing face of the first piston during operation; and
the first face is opposed to the opposing face.

* * * * *